United States Patent
Prober et al.

(10) Patent No.: US 7,122,384 B2
(45) Date of Patent: Oct. 17, 2006

(54) RESONANT LIGHT SCATTERING MICROPARTICLE METHODS

(75) Inventors: James M. Prober, Wilmington, DE (US); Xiumin Cui, Swarthmore, PA (US); Rudy J. Dam, Maple Valley, WA (US); Edwin R. Hendrickson, Hockessin, DE (US); Xueping Jiang, Wilmington, DE (US); Michael P. Perry, Landenberg, PA (US); Larry Eugene Steenhoek, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/702,320

(22) Filed: Nov. 5, 2003

(65) Prior Publication Data

US 2005/0019842 A1 Jan. 27, 2005

Related U.S. Application Data

(60) Provisional application No. 60/424,168, filed on Nov. 6, 2002.

(51) Int. Cl.
*G01N 33/531* (2006.01)

(52) U.S. Cl. ............... 436/524; 436/518; 436/525; 436/527; 436/528; 436/164; 436/523; 435/7.1; 356/436; 356/432; 356/523

(58) Field of Classification Search ........... 435/7.1, 435/4, 7.8; 436/518, 524, 525, 523, 164; 356/300, 301, 335, 436, 432
See application file for complete search history.

(56) References Cited

U.S. PATENT DOCUMENTS

| | | | | |
|---|---|---|---|---|
| 4,890,925 A | * | 1/1990 | Kitamori et al. | 356/432 |
| 5,055,265 A | * | 10/1991 | Finlan | 422/82.05 |
| 5,124,207 A | * | 6/1992 | Hayashi et al. | 428/404 |
| 5,719,060 A | | 2/1998 | Hutchens et al. | |
| 5,837,832 A | | 11/1998 | Chee et al. | |
| 5,981,180 A | | 11/1999 | Chandler et al. | |
| 6,063,573 A | | 5/2000 | Kayyem | |
| 6,180,415 B1 | | 1/2001 | Schultz et al. | |
| 6,200,820 B1 | | 3/2001 | Hansen et al. | |
| 6,210,715 B1 | * | 4/2001 | Starling et al. | 424/489 |
| 6,214,560 B1 | | 4/2001 | Yguerabide et al. | |
| 6,225,047 B1 | | 5/2001 | Hutchens et al. | |
| 6,268,222 B1 | | 7/2001 | Chandler et al. | |
| 6,309,831 B1 | | 10/2001 | Goldberg et al. | |
| 6,342,396 B1 | * | 1/2002 | Perrin et al. | 436/518 |
| 6,379,969 B1 | | 4/2002 | Mauze et al. | |
| 6,529,835 B1 | * | 3/2003 | Wada et al. | 702/21 |
| 6,530,944 B1 | * | 3/2003 | West et al. | 607/88 |
| 6,589,779 B1 | | 7/2003 | McDevitt et al. | |

(Continued)

OTHER PUBLICATIONS

Schena, M. et al., Quantitative monitoring of gene expression patterns with a complementary DNA microarray, Science 270,: 467-470, 1995.

(Continued)

*Primary Examiner*—Long V. Le
*Assistant Examiner*—Melanie J. Yu

(57) ABSTRACT

Microparticle-based analytical methods, systems and applications are provided. Specifically, the use of resonant resonant light scattering as an analytical method for determining either or both a particle's identity and the presence and optionally, the concentration of one or more particular target analytes is described. Applications of these microparticle-based methods in biological and chemical assays are also disclosed.

37 Claims, 37 Drawing Sheets

U.S. PATENT DOCUMENTS

| | | | |
|---|---|---|---|
| 6,602,702 B1 | 8/2003 | McDevitt et al. | |
| 6,618,144 B1* | 9/2003 | Reed | 356/343 |
| 6,649,403 B1 | 11/2003 | McDevitt et al. | |
| 6,680,206 B1 | 1/2004 | McDevitt et al. | |
| 6,699,724 B1* | 3/2004 | West et al. | 436/525 |
| 6,710,366 B1* | 3/2004 | Lee et al. | 257/14 |
| 6,713,298 B1 | 3/2004 | McDevitt et al. | |
| 2002/0000814 A1 | 1/2002 | Robinson et al. | |
| 2002/0097401 A1* | 7/2002 | Maleki et al. | 356/436 |
| 2002/0174923 A1 | 11/2002 | Taguchi et al. | |
| 2003/0016897 A1 | 1/2003 | Walt et al. | |
| 2003/0049866 A1* | 3/2003 | Bushway et al. | 436/518 |
| 2003/0064422 A1 | 4/2003 | McDevitt et al. | |
| 2003/0096302 A1* | 5/2003 | Yguerabide et al. | 435/7.1 |
| 2003/0112432 A1* | 6/2003 | Yguerabide et al. | 356/317 |
| 2003/0124733 A1* | 7/2003 | Bushway et al. | 436/174 |
| 2003/0174923 A1* | 9/2003 | Arnold et al. | 385/12 |
| 2003/0186228 A1 | 10/2003 | McDevitt et al. | |
| 2004/0029259 A1 | 2/2004 | McDevitt et al. | |
| 2004/0053322 A1 | 3/2004 | McDevitt et al. | |

OTHER PUBLICATIONS

Shalon et al., A DNA microarray system for analyzing complex DNA samples using two-color fluorescent probe hybridization, Genome Res. 6, pp. 639-645, 1996.

Weinberger et al., Current achievements using ProteinChip® Array technology, Curr. Opin. Chem. Biol., 6(1), pp. 86-91, 2002.

Nelson et al., Surface plasmon resonance imaging measurements of DNA and RNA hybridization adsorption onto DNA microarrays, Anal. Chem. 73, 1-7, 2001.

Xu et al., Multiplexed SNP genotyping using the Qbead™ system; a quantum dot-encoded microsphere-based assay, Nucleic Acids Research 31(8), e43 2003.

Nicewarner-Pena et al., Submicrometer metallic barcodes, Science 294, pp. 137-141, 2001.

Walton et al., Particles for multiplexed analysis in solution: detection and identification of striped metallic particles using optical microscopy, Anal. Chem. 74, pp. 2240-2247, 2002.

Bohren et al., Absorption and scattering of Light by Small Particles, John Wiley and Sons, 1983.

Kerker, M., Scattering of Light and Other Electromagnetic Radiation, Academic Press, 1969.

Chylek et al., Narrow resonance structure in the Mie scattering characteristics, Appl. Optics 17, pp. 3019-3021, 1978.

Conwell et al., Resonant spectra of dielectric spheres, J. Opt. Soc. America A 1, 62-67, 1984.

Probert-Jones, J. R. Resonance component of backscattering by large dielectric spheres, J. Opt. Soc. America A 1, pp. 822-830, 1984.

Hill et al., Morphology-dependent resonances associated with stimulated processes in microspheres, J. Opt. Soc. America B 3, 1509-1514.

Lettieri et al., Resonance light scattering from a liquid suspension of microspheres, Appl. Optics 25(23), 4325-4331, 1986.

Chylek, P. et al., Interference structure of the Mie extinction cross section, J. Opt. Soc. America A 6, pp. 1846-1851, 1989.

Hill et al., Structural resonances observed in the fluorescense emission from small spehres on substrates, Appl. Optics 23, p. 1680, 1984.

Conwell et al., Efficient automated algorithm for the sizing of dielectric microspheres using the resonance spectrum, J. Opt. Soc. America A 1, 1181-1186, 1984.

Lam et al., Explicit asymptotic formulas for the positions, widths, and strengths of resonances in Mie scattering, J. Opt. Soc. America B 9, pp. 1585-1592, 1992.

Chylek, P. Resonance structure of Mie scattering: distance between resonances, J. Opt. Soc. America A 7, pp. 1609-1613, 1990.

Guimaraes et al., Uniform approximation to Mie resonances, J. Modern Optics 41, 625-647, 1994.

Kaiser et al., Stable algorithm for the computation of Mie coefficients for scattered and transmitted fields of a coated sphere, Computers in Physics 7, pp. 682-686, 1993.

Hightower et al., Resonant Mie scattering from a layered sphere, Appl. Optics 27, 4850-4855, 1988.

Ray et al., Simultaneous determination of size and wavelength-dependent refractive indices of thin-layered droplets from optical resonances, Apl. Optics 34, pp. 7759-7770, 1995.

Huckaby et al., Determination of size, refractive index, and dispersion of single droplets from wavelength-dependent scattering spectra, Appl. Optics 33, pp. 7112-7125, 1994.

Hill et al., Sizing dielectric spheres and cylinders by aligning measured and computed resonances locations: algorithm for multiple orders, Appl. Optics 24, 2380-2390, 1985.

Chylek et al., Simultaneous determining of refractive index and size of spherical dielectric particles from light scattering date, Appl. Optics 22, pp. 2303-2307.

Whitten et al., Morphological resonances for multicomponent immunoassays, Appl. Optics 34, 3203-3207, 1995.

Vollmer et al., Protein detection by optical shift of a resonant microcavity, Appl. Phys. Lett. 80, 4057-4059, 2002.

Serpenguzel et al., Excitation of resonances of microspheres on an optical fiber, Optics Lett 20, 654-656, 1995.

Krioukov et al.,Sensor based on an integrated optical microcavity, Optic Letters, vol. 27, No. 7, pp. 512-514, Apr. 1, 2002.

Gorodetsky et al., Ultimate Q of optical microsphere resonators, Optics Letters, vol. 21, No. 7, pp. 453-455, Apr. 1, 1996.

Vollmer et al., Multiplexed DNA Quantification by Spectroscopic Shift of Two Microsphere Cavities, Biophysical Journal, vol. 85, 1974-1979, Sep. 2003.

Butkus, Silica microspheres enable sensitive DNA detection, Biophotonics in Practice, Biophotonics International, pp. 34-36, Oct. 2003.

Arnold et al., Shift of whispering-gallery modes in microspheres by protein adsorption, Optics Letters, vol. 28, No. 4, pp. 272-274, Feb. 15, 2003.

Griffel et al., Morphology-dependent resonances of a microsphere-optical fiber system, Optics Letters, vol. 21, No. 10, pp. 695-697, May 15, 1996.

Krioukov et al., Integrated optical microcavities for enhanced evanescent-wave spectroscopy, Optics Letters, vol. 27, No. 17, pp. 1504-1506, Sep. 1, 2002.

* cited by examiner

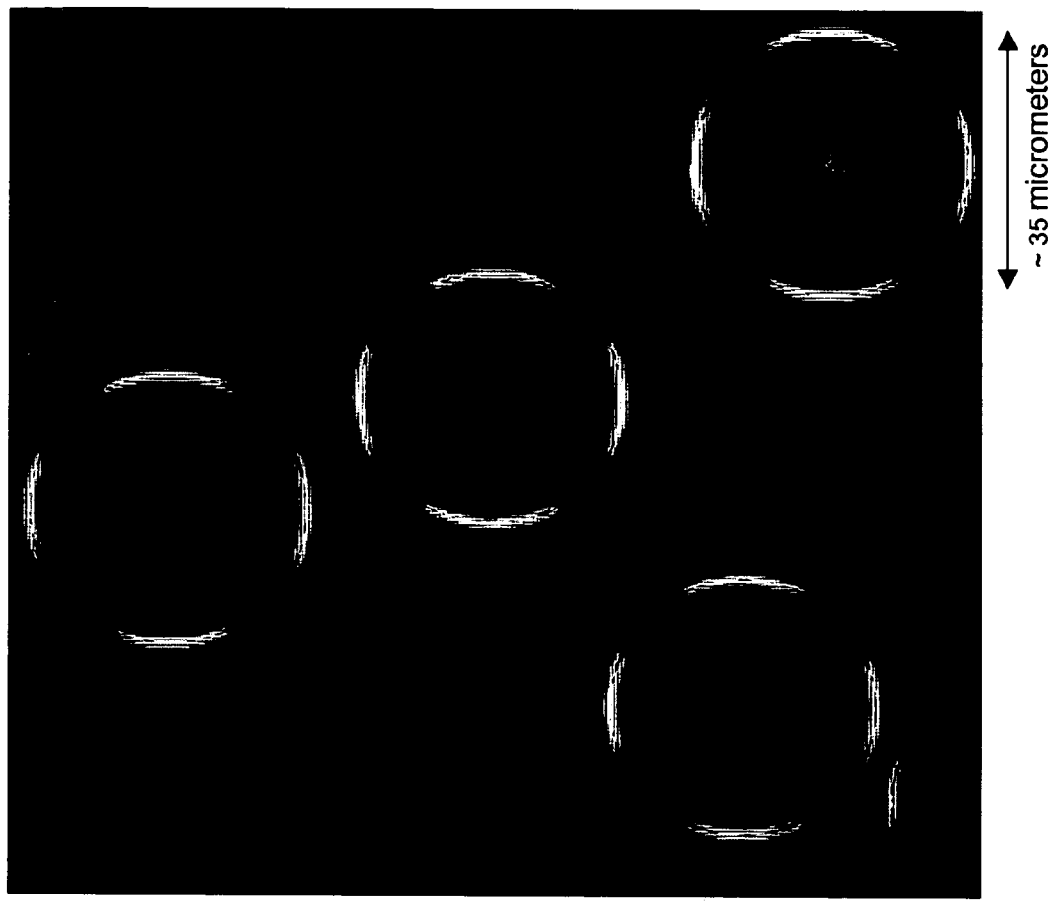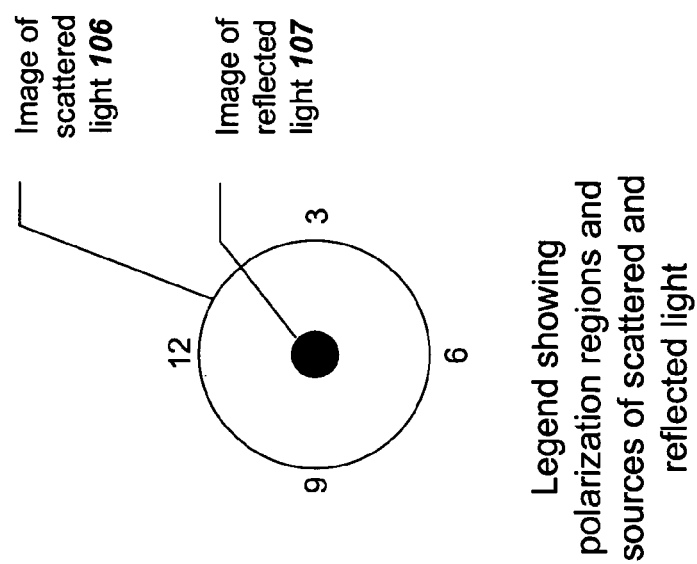
Figure 8

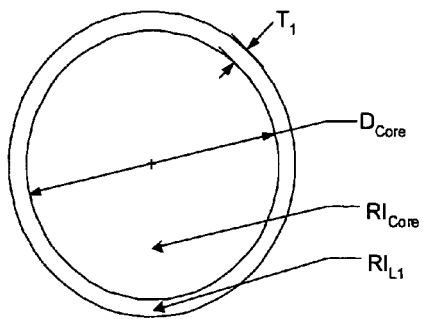
Reference particle for Example 14
High RI core plus one layer, one set of resonances
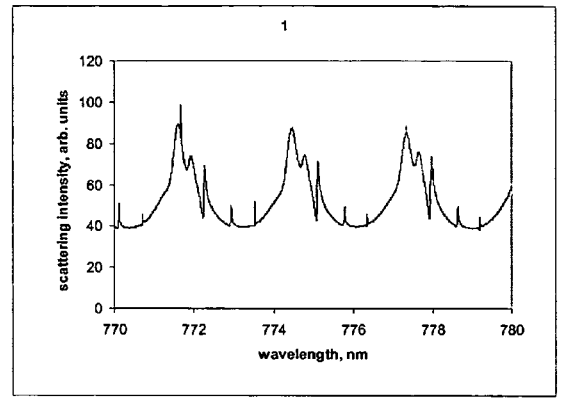
Scattering spectrum for reference particle 1
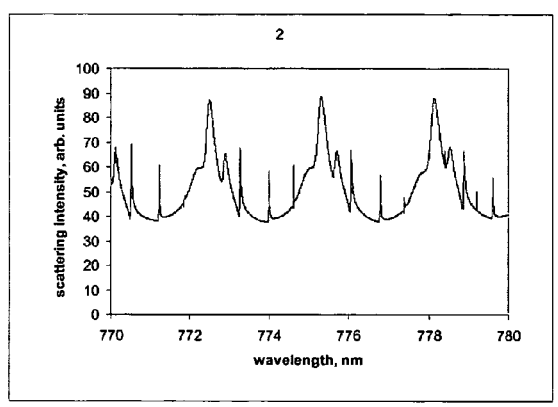
Scattering spectrum for particle 2
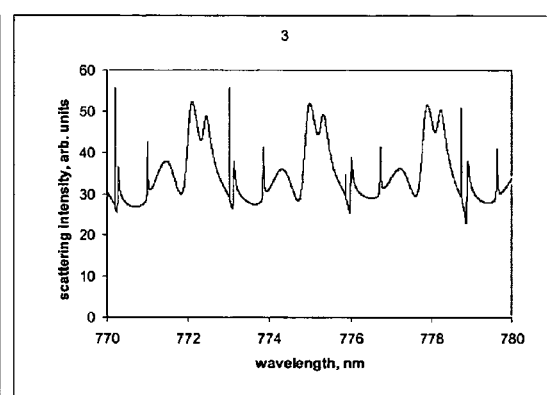
Scattering spectrum for particle 3
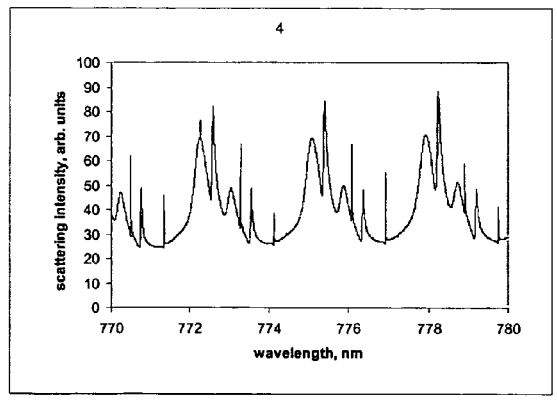
Scattering spectrum for particle 4
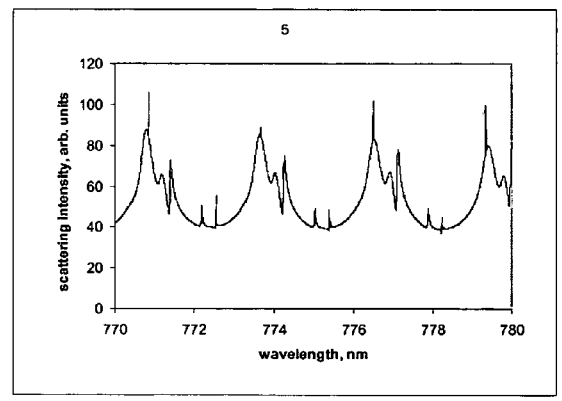
Scattering spectrum for particle 5
Figure 18

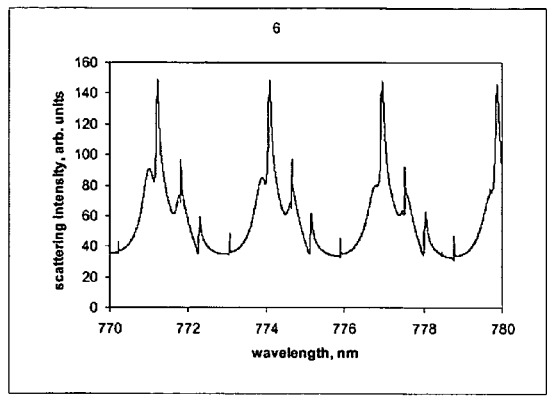
Scattering spectrum for particle 6
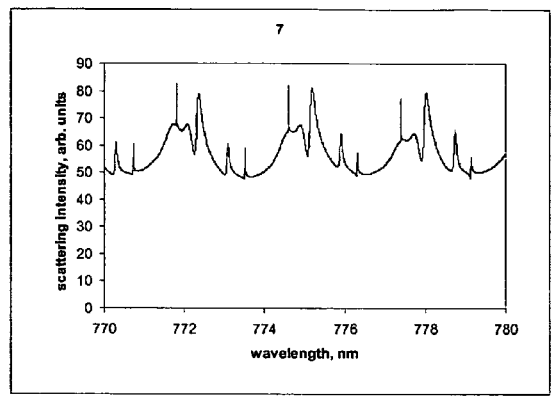
Scattering spectrum for particle 7
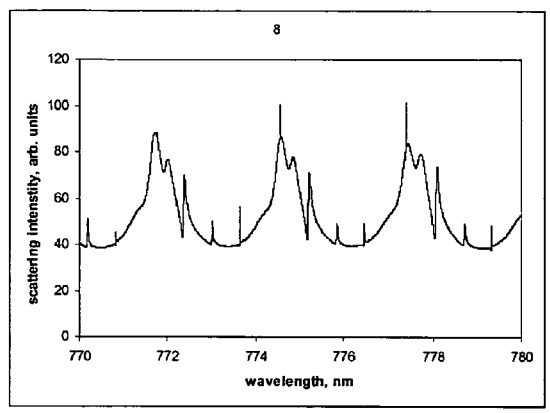
Scattering spectrum for particle 8 addition of 10 nm protein layer
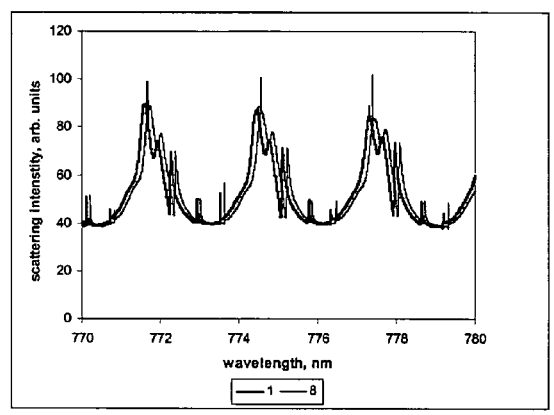
Scattering spectra for particles 1 and 8 compared
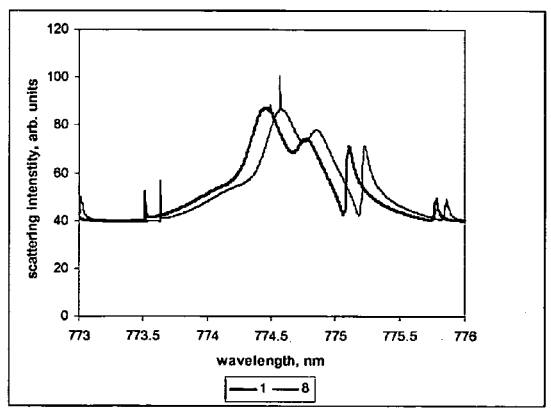
Particles 1 and 2 compared (expanded scale)
Figure 19

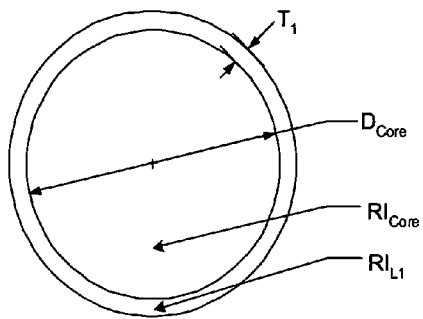
Reference particle for Example 15
Low RI core plus one layer, one set of
resonances
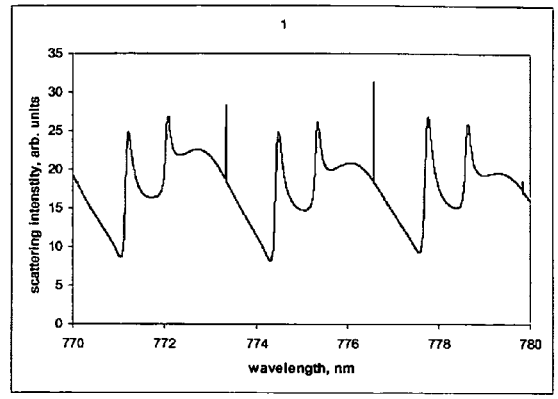
Scattering spectrum for particle 1
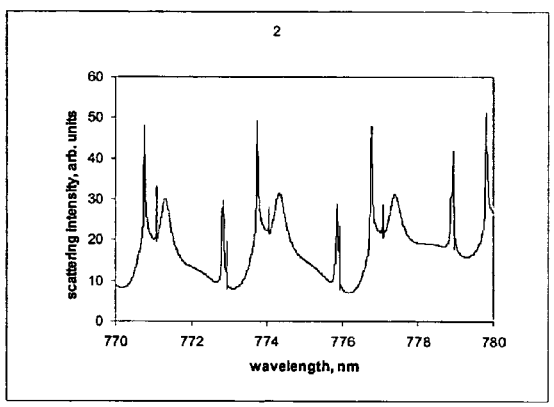
Scattering spectrum for reference particle 2
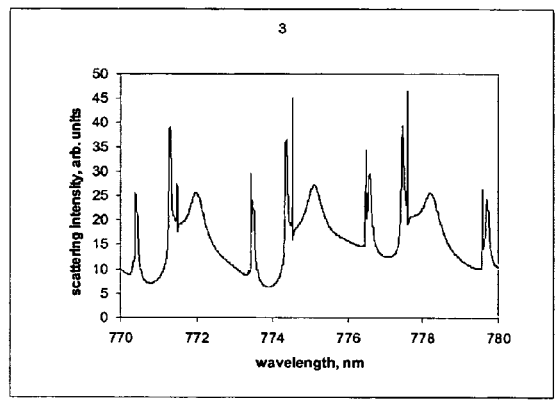
Scattering spectrum for particle 3
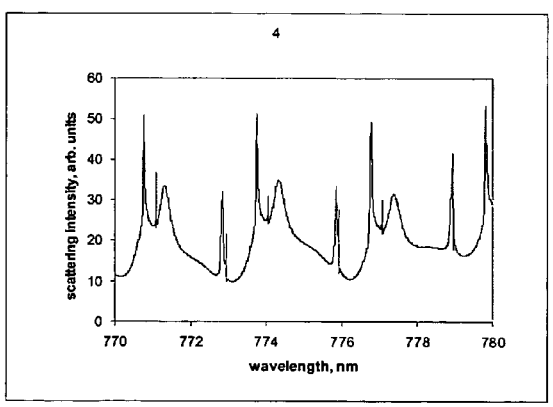
Scattering spectrum for particle 4
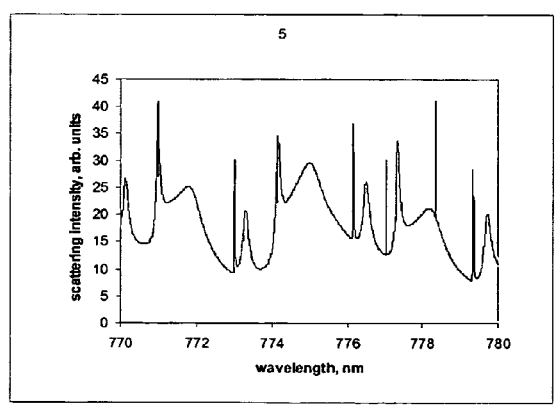
Scattering spectrum for particle 5
Figure 20

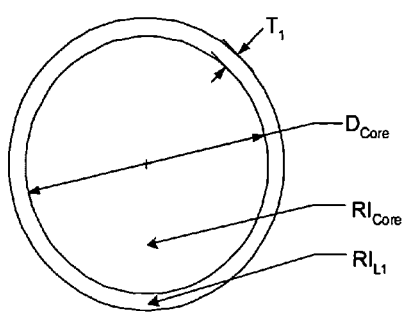
Reference particle for Example16
High RI core plus one layer, two sets of resonances
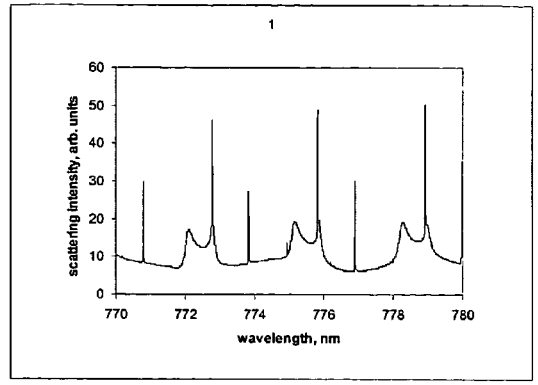
Scattering spectrum for particle 1
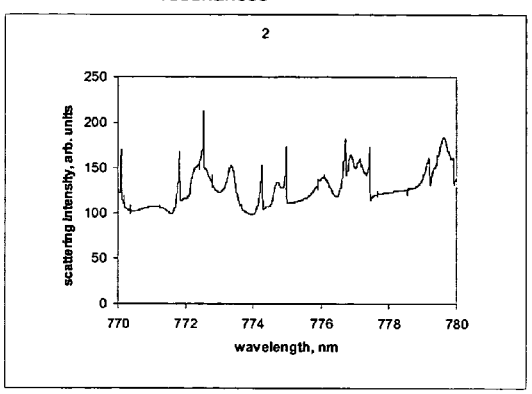
Scattering spectrum for reference particle 2
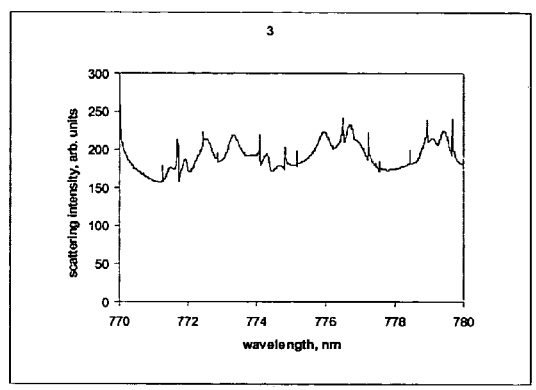
Scattering spectrum for particle 3
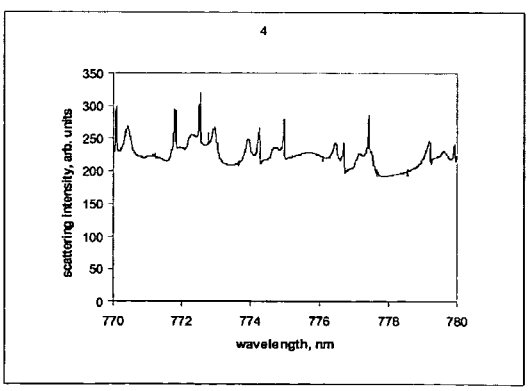
Scattering spectrum for particle 4
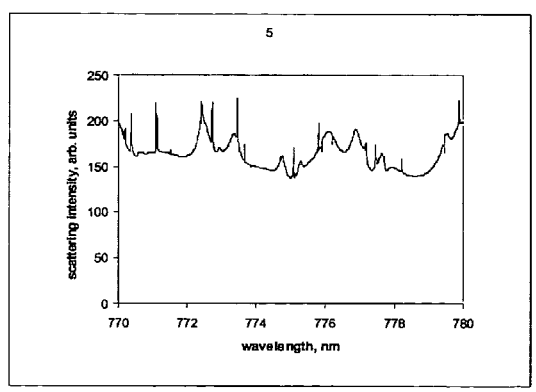
Scattering spectrum for particle 5
Figure 22

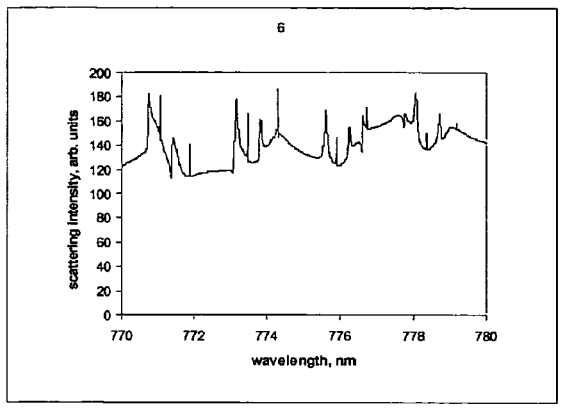
Scattering spectrum for particle 6
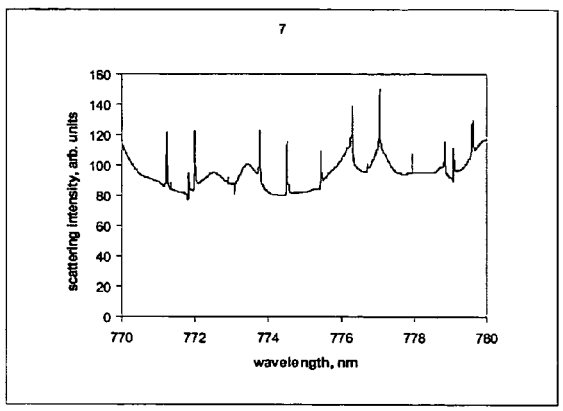
Scattering spectrum for particle 7
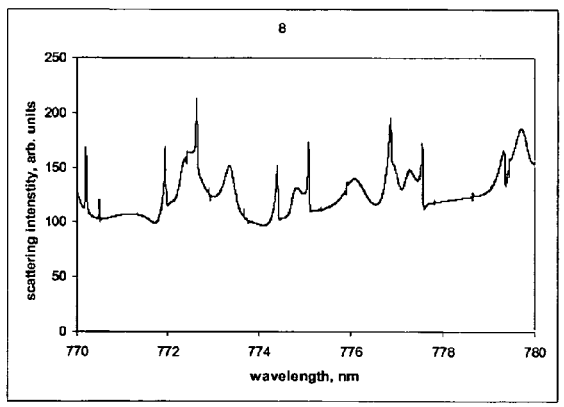
Scattering spectrum for particle 8 addition of 10 nm protein layer
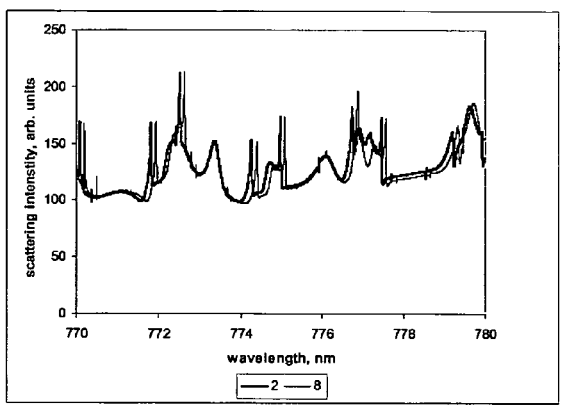
Scattering spectra for particles 2 and 8 compared
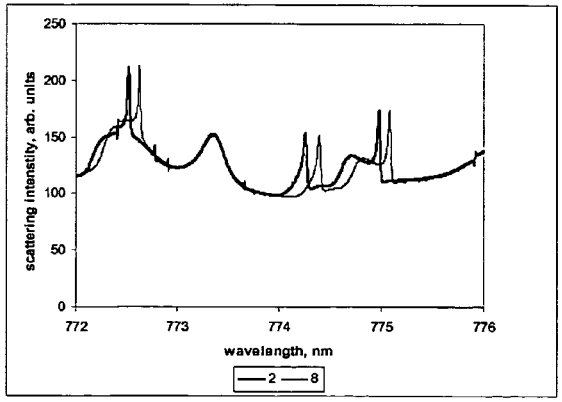
Particles 2 and 8 compared (expanded scale)
Figure 23

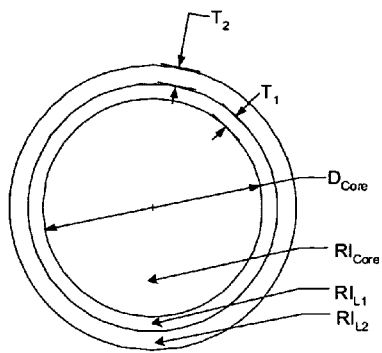
Reference particle for Example 17
Low RI Core plus 2 layer, 2 sets of resonances
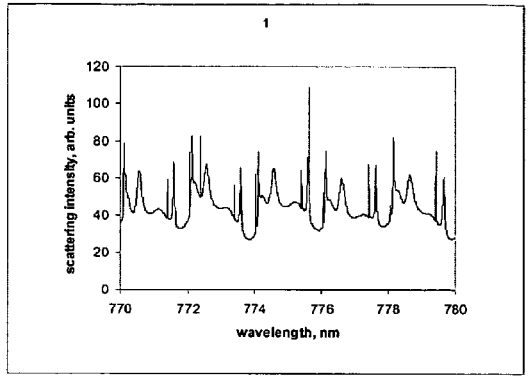
Scattering spectrum for particle 1
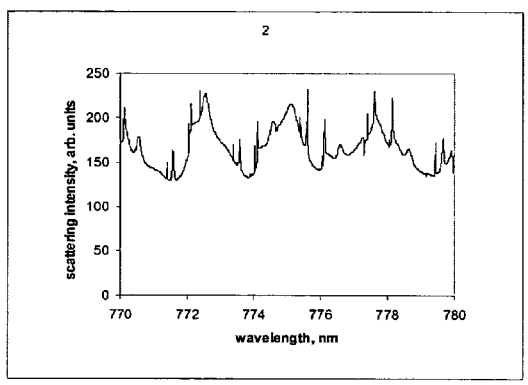
Scattering spectrum for reference particle 2
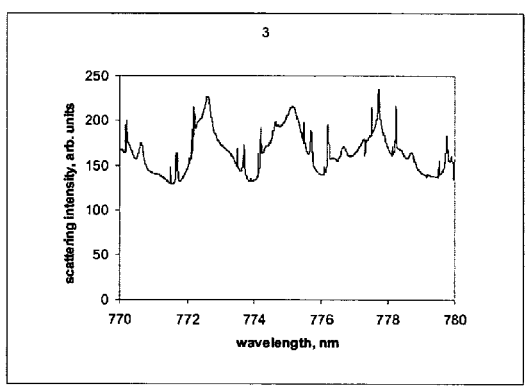
Scattering spectrum for particle 3
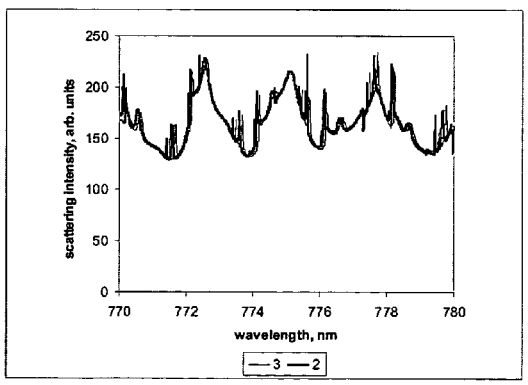
Scattering spectra for particles 2 and 3 compared
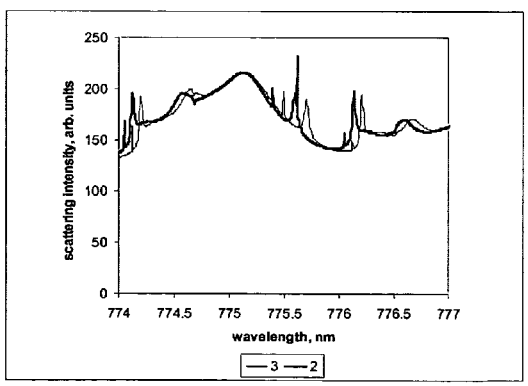
Particles 2 and 3 compared (expanded scale)
Figure 24

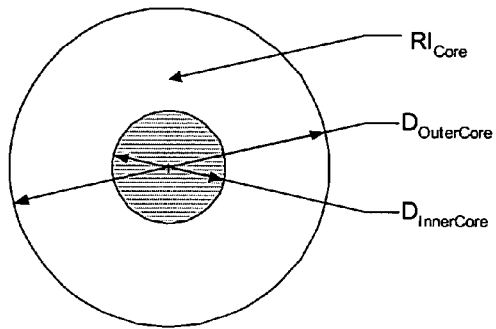
Reference particle for Example 18
Core with black center
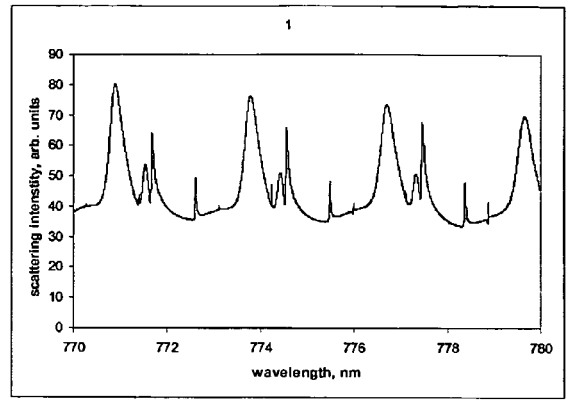
Scattering spectrum for particle 1
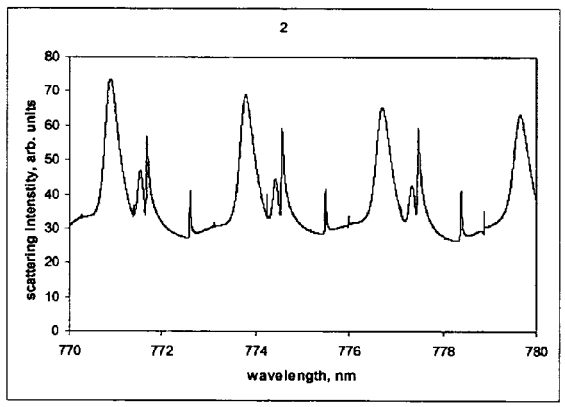
Scattering spectrum for particle 2, 5 μ core
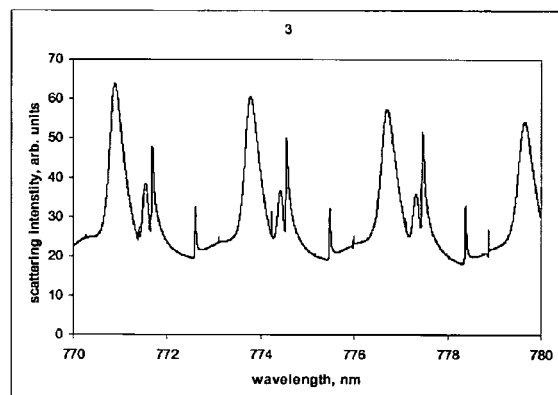
Scattering spectrum for particle 3, 10 μ core
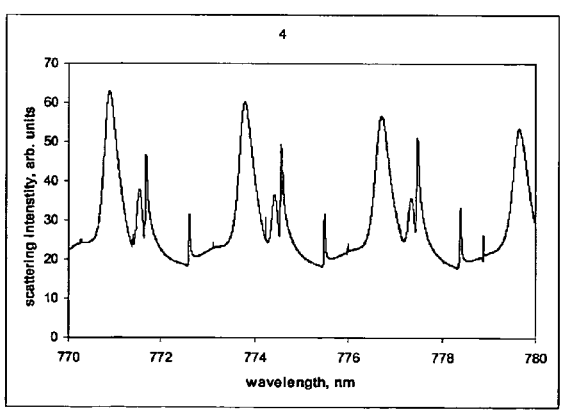
Scattering spectrum for particle 4, 15 μ core
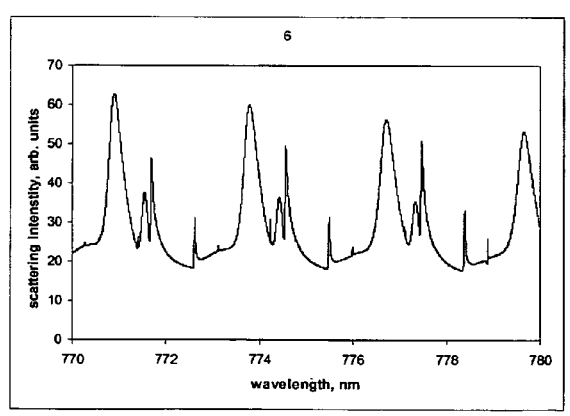
Scattering spectrum for particle 6, 25 μ core
Figure 25

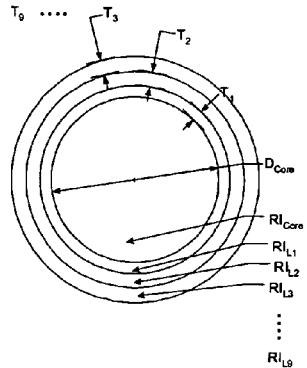
Reference particle for Example19
Radially varying refractive index in core
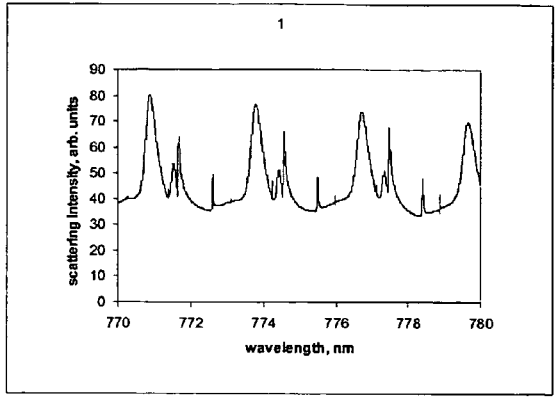
Scattering spectrum for particle 1
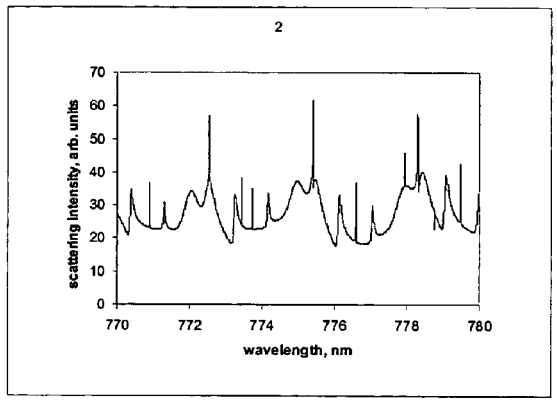
Scattering spectrum for particle 2
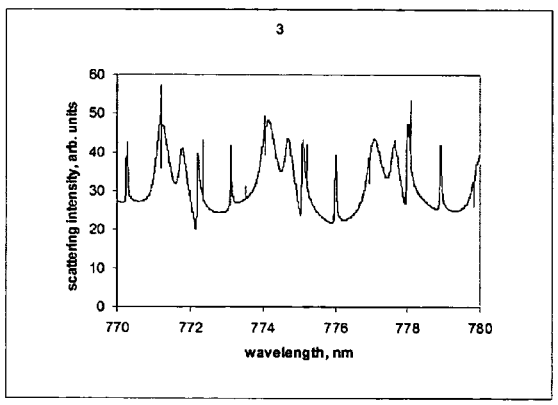
Scattering spectrum for particle 3
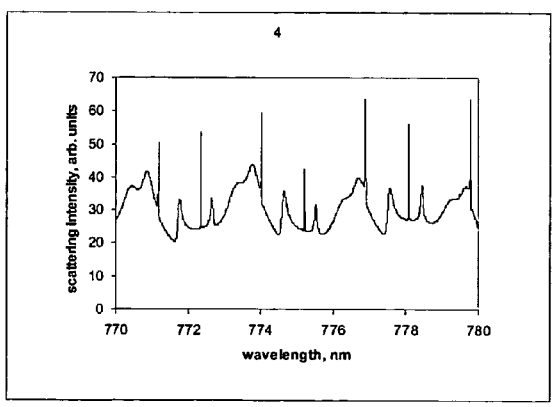
Scattering spectrum for particle 4
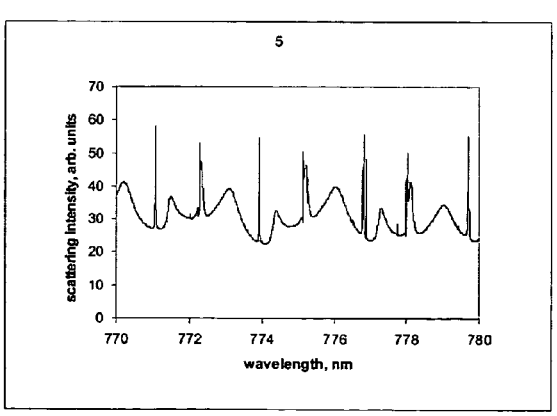
Scattering spectrum for reference particle 5
Figure 28

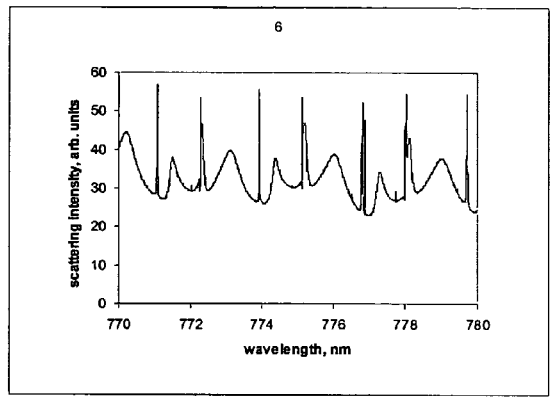
Scattering spectrum for particle 6
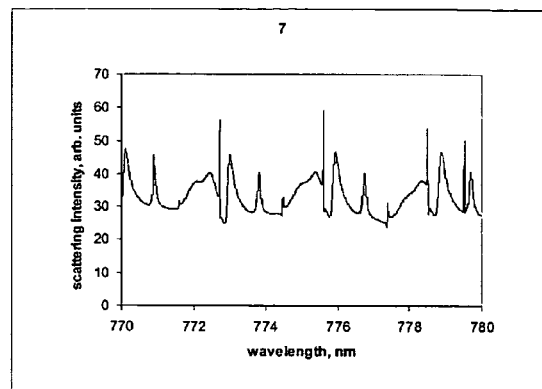
Scattering spectrum for particle 7
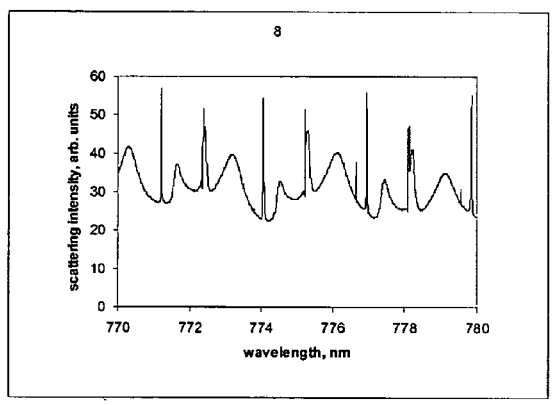
Scattering spectrum for particle 8
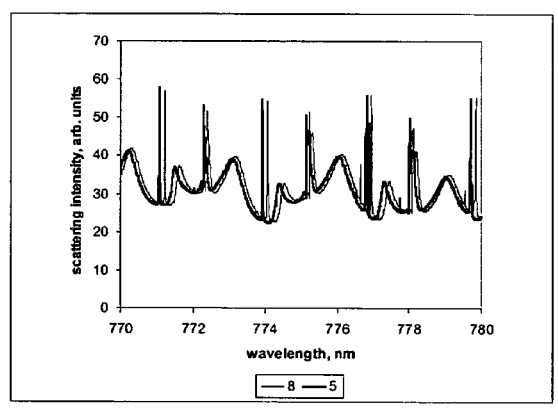
Scattering spectra for particles 5 and 8 compared
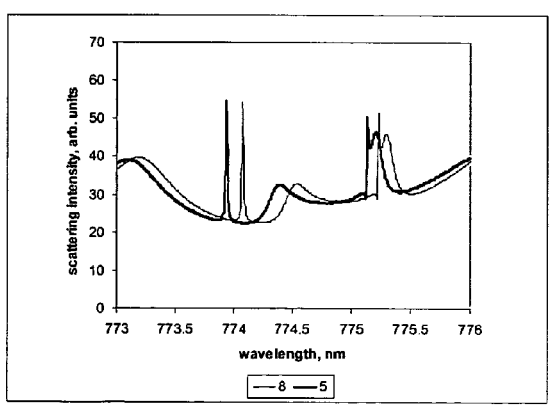
Particles 5 and 2 compared (expanded scale)
Figure 29

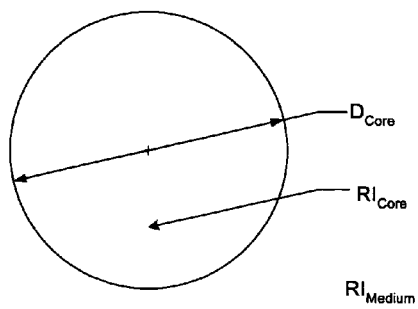
Reference particle for Example20
Effect of medium refractive index
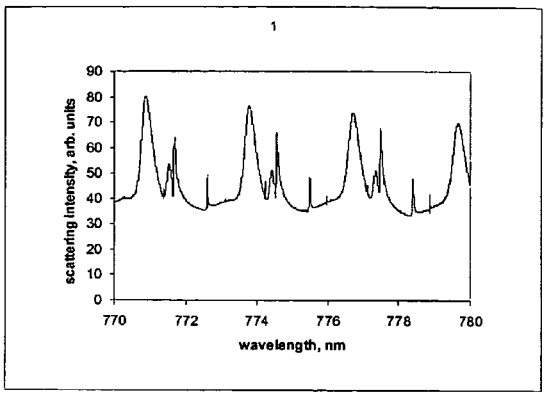
Scattering spectrum for reference particle 1
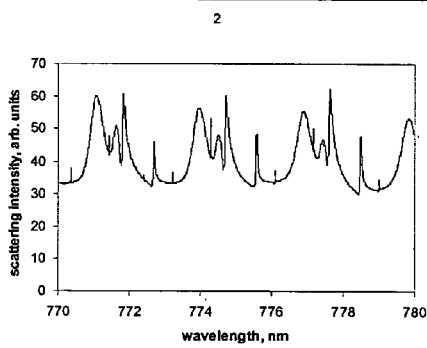
Scattering spectrum for particle 2
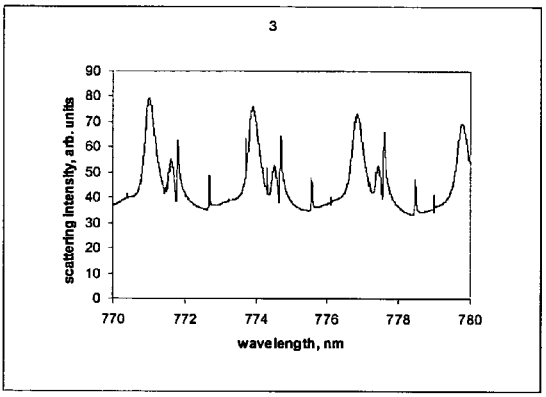
Scattering spectrum for particle 3
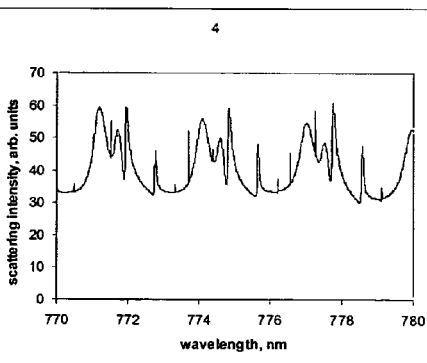
Scattering spectrum for particle 4
Figure 30

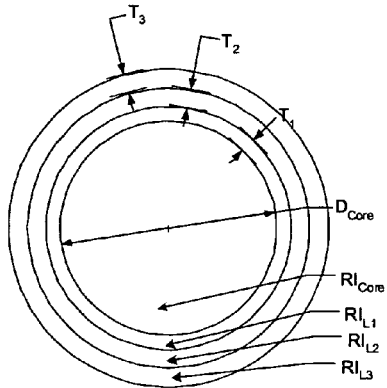
Reference particle for Example 21
Signal amplification using refractive index 2.5 material
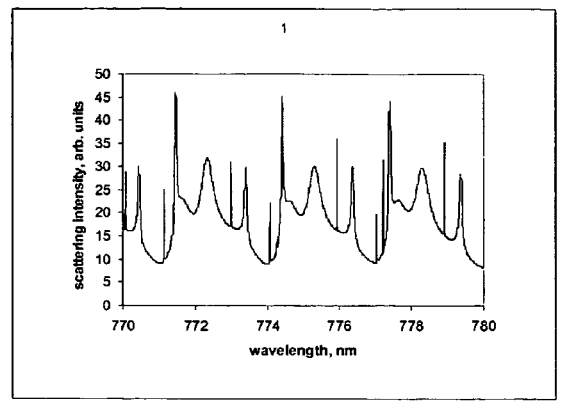
Scattering spectrum for reference particle 1
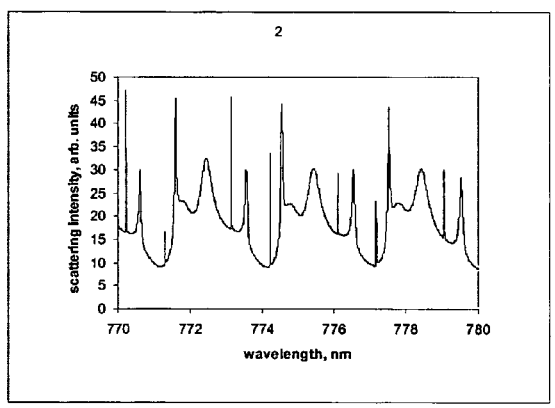
Scattering spectrum for particle 2
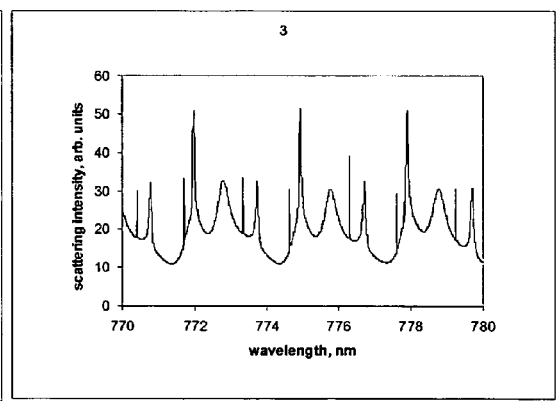
Scattering spectrum for particle 3
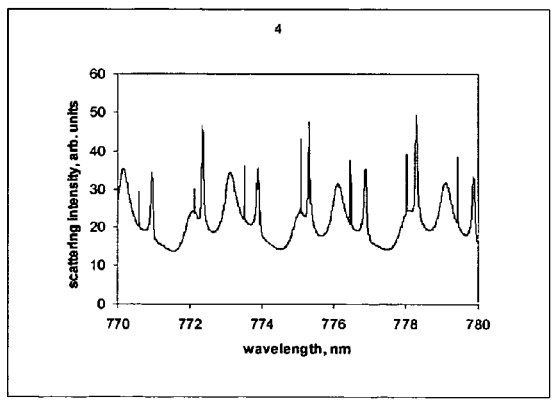
Scattering spectrum for particle 4
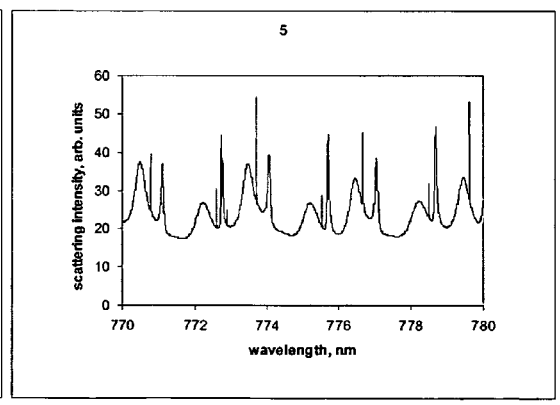
Scattering spectrum for particle 5
Figure 32

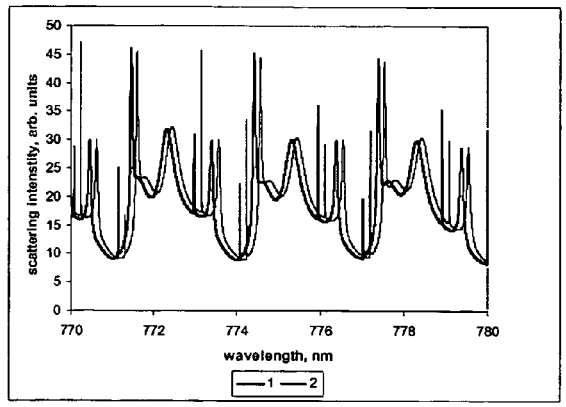
Scattering spectra for particles 1 and 2 compared (addition of protein layer)

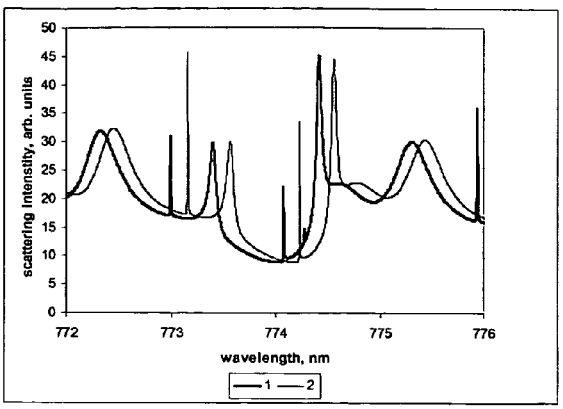
Scattering spectra for particles 1 and 2 compared (expanded scale)

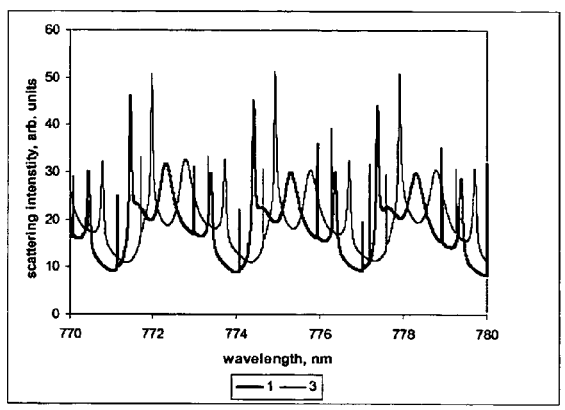
Scattering spectra for particles 1 and 3 compared (addition of protein layer with 2 nm signal amplifier)

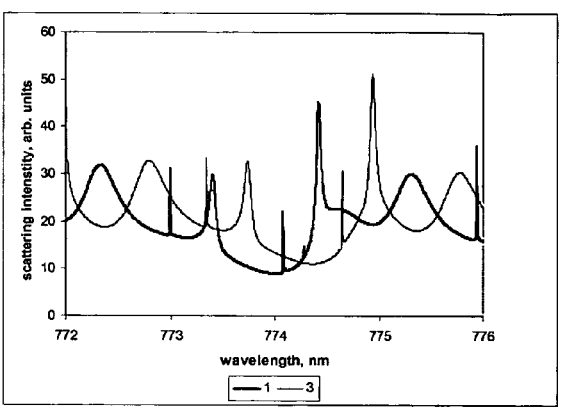
Scattering spectra for particles 1 and 3 compared (expanded scale)

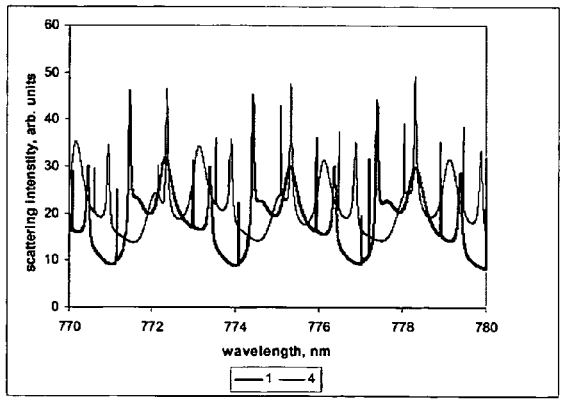
Scattering spectra for particles 1 and 4 compared (addition of protein layer with 4 nm signal amplifier)

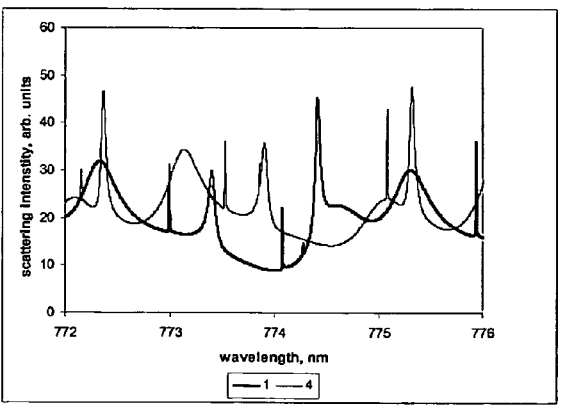
Scattering spectra for particles 1 and 4 compared (expanded scale)

Figure 33

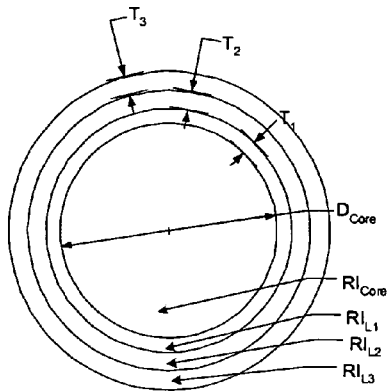
Reference particle for Example22
Signal amplification using refractive
index 2.2 material
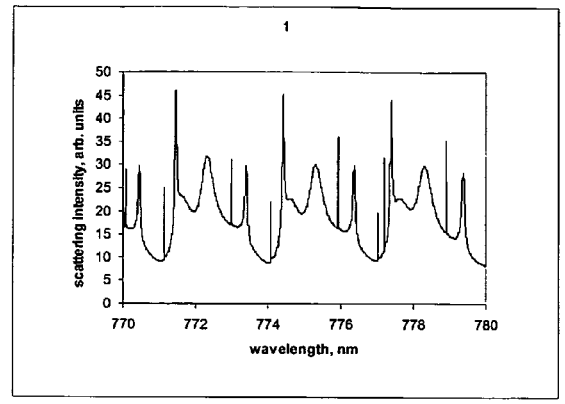
Scattering spectrum for reference particle 1
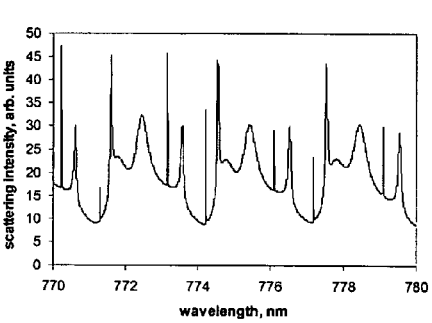
Scattering spectrum for particle 2
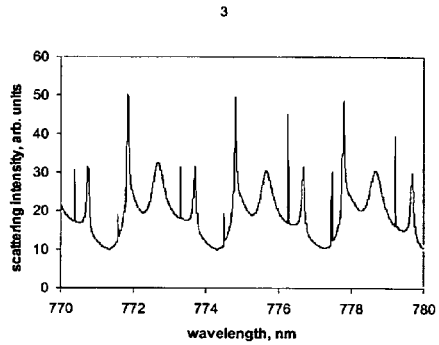
Scattering spectrum for particle 3
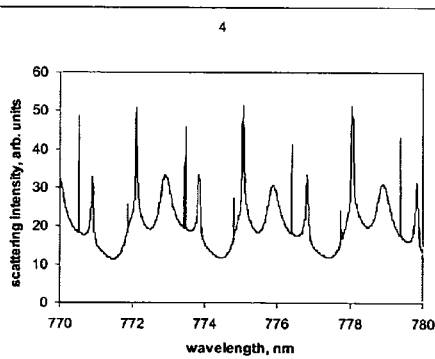
Scattering spectrum for particle 4
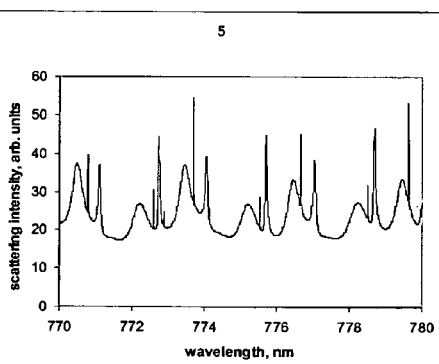
Scattering spectrum for particle 5
Figure 34

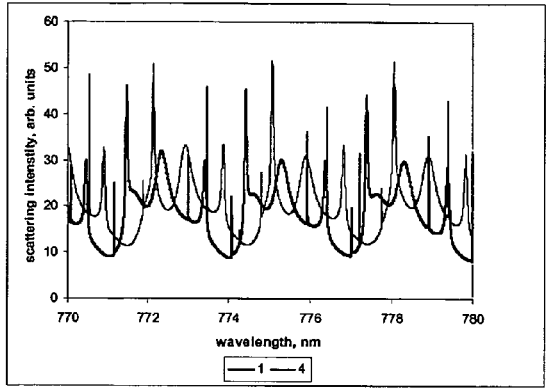

Scattering spectra for particles 1 and 4 compared
(addition of protein layer with 4 nm signal amplifier)

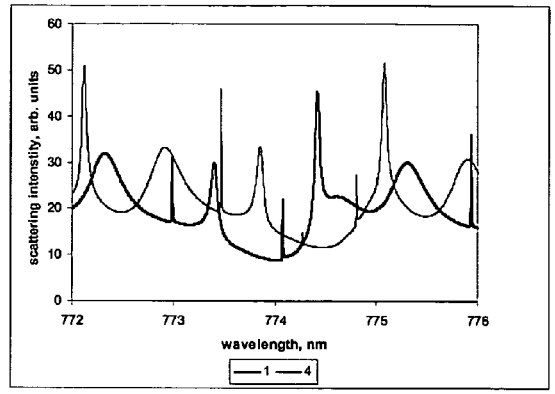

Scattering spectra for particles 1 and 4 compared
(expanded scale)

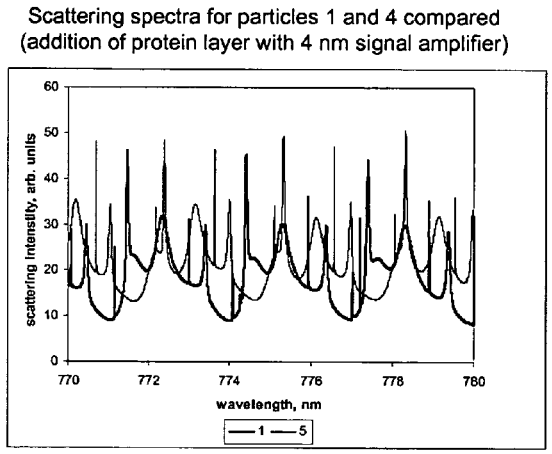

Scattering spectra for particles 1 and 5 compared
(addition of protein layer with 6 nm signal amplifier)

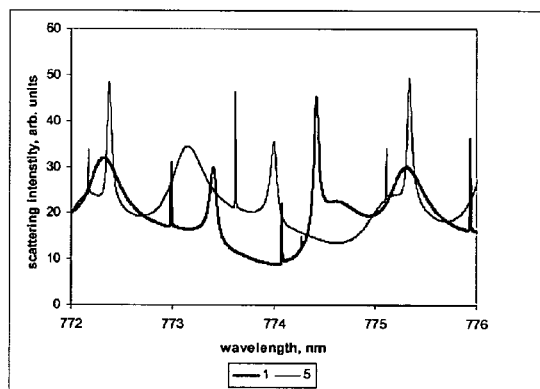

Scattering spectra for particles 1 and 5 compared
(expanded scale)

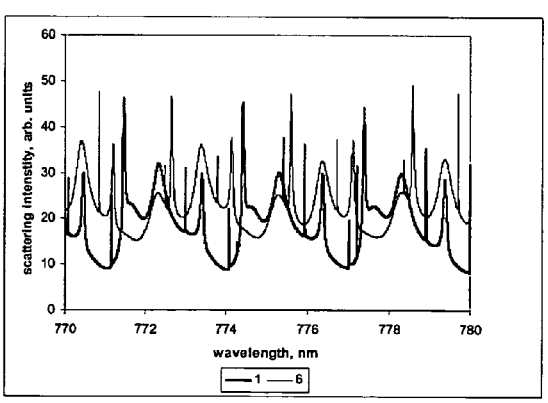

Scattering spectra for particles 1 and 6 compared
(addition of protein layer with 8 nm signal amplifier)

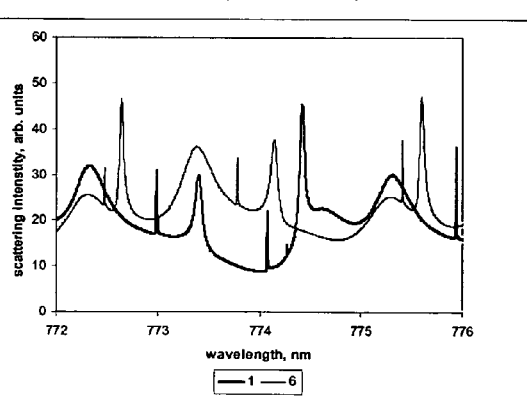

Scattering spectra for particles 1 and 6 compared
(expanded scale)

Figure 36

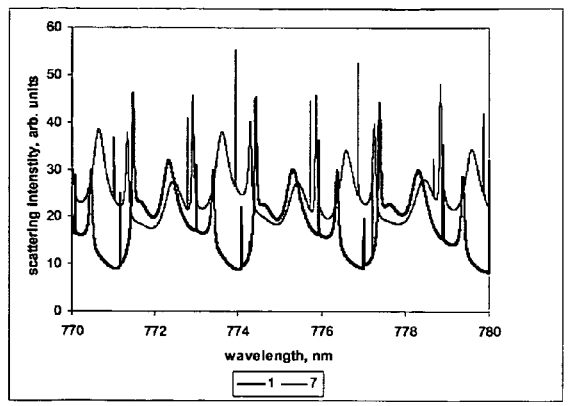 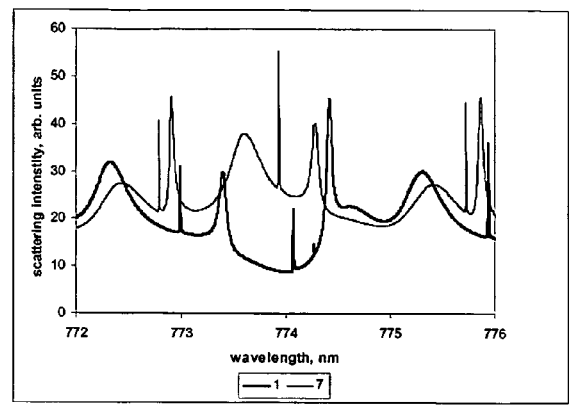
Scattering spectra for particles 1 and 7 compared (addition of protein layer with 10 nm signal amplifier)
Scattering spectra for particles 1 and 7 compared (expanded scale)
Figure 37

RESONANT LIGHT SCATTERING MICROPARTICLE METHODS

FIELD OF INVENTION

This invention generally relates to methods, systems, and applications for microparticle-based measurements using resonant light scattering, comprising one or more of the following elements: particle identification, determining the identity and degree of analyte binding, and application of these methods in multiplexed biological and chemical assays.

BACKGROUND

Advances in bioanalysis are increasingly driven by miniaturization and multiplexing, i.e. the ability to measure many samples simultaneously. The ability to measure more analytes from smaller sample volumes, dictated in many cases by limited sample size, has led to development of miniaturized microfluidics-based sample manipulation systems and novel methods for analysis in micro-scale systems. Examples include a wide variety of existing biological and chemical measurements, for example DNA sequencing, protein analysis, single-nucleotide polymorphism (SNP) analysis, high-speed and high-resolution separations and chromatography using lab-on-chip devices, and many others. Special emphasis has been given in the past decade on development of highly parallel, miniaturized assay systems for the large-scale study of genomics and proteomics and for high-throughput screening in discovery research. Examples include 2-dimensional fixed "biochip" microarrays and, more recently, identifiable micrometer-sized particles. Both approaches depend on specific binding or capture of analytes to complementary probes on the surface of the array or particle, for example by base-pair hybridization between nucleic acids, or hydrogen bonding, hydrophobic interactions, and other binding mechanisms between polypeptides.

Microarrays and associated support technologies emerged in the 1990's and now comprise an established industry. For example, Affymetrix's GeneChip® technology is a manufacturing process that uses photolithography, solid phase chemistry, and semiconductor fabrication techniques to build hundreds of thousands of DNA sequence probes on a two-dimensional array. This technology is described in, for example, Schena, M. et al., "Quantitative monitoring of gene expression patterns with a complementary DNA microarray", *Science* 270, 467–470 (1995); Shalon, D. et al., "A DNA microarray system for analyzing complex DNA samples using two-color fluorescent probe hybridization", *Genome Res.* 6, 639–645 (1996); Goldberg, M. J. and Rava, R. P., "Method of manufacturing biological chips", U.S. Pat. No. 6,309,831 (2001) and Chee, M. et al., "Arrays of nucleic acid probes on biological chips", U.S. Pat. No. 5,837,832 (1998). Other DNA microarray technologies have been developed, for example by Hyseq, Inc., Molecular Dynamics, Inc., Nanogen, Incyte Pharmaceuticals, Inc., and others known in the art.

Fixed arrays are also being developed for proteomics, defined herein as the systematic study of the proteins in a biological system. For example, Ciphergen Biosystems' ProteinChip® array technology is a process that includes chromatography and protein characterization based upon the surface-enhanced laser desorption/ionization (SELDI). These techniques combine laser-based molecular weight determination with the use of a chemically active protein chip array. This technology is described in, for example, Hutchens, T. W., "Use of retentate chromatography to generate difference maps", U.S. Pat. No. 6,225,047 (2001); Hutchens, T. W., "Methods and apparatus for desorption and ionization of analytes", U.S. Pat. No. 5,719,060 (1998); and Weinberger, S. R., et al., "Current achievements using ProteinChip® Array technology", *Curr. Opin. Chem. Biol.*, 6(1), 86–91 (2002). A number of other protein array technologies have also been developed for example by Agilent Technologies, Inc., Zyomyx, Inc., Cambridge Antibody Technology, and others known in the art.

Independent of the type of analyte being measured, microarrays base the ability to determine the identity of each probe by its fixed position within the array. Typically, each probe is synthesized or spotted at known coordinates within a grid on the surface of a substrate or chip. These "biochip" systems can carry out large numbers of analyses simultaneously, but they suffer from known disadvantages. For example, microarrays have inherently inefficient binding kinetics. Because of poor mixing at the surface and the dimensions of a typical biochip, an analyte must cover relatively large diffusion distances to bind to its complementary probe. This results in slow diffusion of analytes to and on the surface, incomplete binding reactions, and substantial lengthening of the protocol. Additionally, the application and measurement of samples on microarrays is inherently a batch process, not particularly well suited for automation. Some types of microarrays can be expensive and difficult to customize quickly as the needs of an experiment or assay might require. Variability across a microarray can lead to degraded reproducibility and precision, requiring in some cases substantial redundancy in the measurements. Sensitivity and dynamic range are frequently reported to be problematic in the analysis of microarray data. Also, with fixed microarrays it is not typically possible to recover, sort, post-process, or perform subsequent measurements on the analyte. Finally, in most microarray systems, a reporter group such as a fluorophore is required to detect binding of an analyte. Although some advances have been reported (see for example Kayyem, J. F., "Cycling probe technology using electron transfer detection", U.S. Pat. No. 6,063,573 (2000); Nelson, B. P., et al., "Surface plasmon resonance imaging measurements of DNA and RNA hybridization adsorption onto DNA microarrays", *Anal. Chem.* 73, 1–7 (2001)), the use of external reporter groups requires washing the array after exposure to the sample in order to remove interfering signals from unbound reporters. The resulting measurement in most microarray systems is thus an end-point measurement; i.e. the microarray is not capable of real-time, continuous measurement of binding between analyte and probe.

The use of microparticles circumvent many of the deficiencies of 2-dimensional microarrays, primarily because the assays can be done in a small, well-mixed volume in which binding kinetics are more favorable. When the sample is well mixed, there is no location-dependent variability as is the case with fixed arrays. Further, small particle size and small sample volumes increase the local concentration of probes and reduce the diffusion length an analyte must travel in order to bind to a probe, thus increasing the speed and degree of completion of binding reactions. Microparticles can be manipulated more readily by automated sample handling systems, thus the potential for customization and automation is favorable compared to two-dimensional biochip formats.

Flexibility is a further key advantage in particle-based assays. Since individual particles can be tracked and manipulated, it is in principle possible to isolate the analyte or carry out additional measurements on a subset of the particles. Creation of custom assays is made simpler by the ability to quickly select a subset of particles for a specific purpose out of a larger master library.

There remains, however, a need for innovation in the detection of binding. As mentioned previously, although non-labeled binding detection has been reported for fixed array systems, the continuing use of external reporter groups in particle-based assays remains a key disadvantage since the associated drawbacks are the same as for fixed arrays. As will be disclosed in detail below, a key object of the present invention is to eliminate the requirement for reporter groups in particle-based assays, thus simplifying the protocol, reducing time and cost, and enabling the measurement of binding in real time.

In a typical particle-based assay system, each microparticle carries many copies of a unique probe on its surface. Because the microparticles can be in free suspension in some applications, it is not possible in those cases to link the identity of the probe to a fixed position, as done in fixed arrays. Rather, identity of the probe must be uniquely linked to the identity of the particle, thus requiring each particle to have a unique identifying label or marker. In the literature, particle identification is typically accomplished by incorporation of colored or fluorescent molecules, barcodes, or nanoparticles with distinctive fluorescent signatures. Thus, the number of particle-based assays that can be performed in parallel is limited by the number of distinguishable combinations provided by the specific labels employed, e.g. the number of fluorophores, and possibly their relative abundance.

An example of fluorescence-based particle identification is Luminex Corporation's FlowMetrix® system and Laboratory Multi-Analyte Profiling (LabMAP®) technology. This system allows up to about 100 to 1000 analytes to be measured sequentially by flow cytometry. This technology incorporates microspheres that are internally labeled with two or more distinct fluorescent dyes. The microspheres are further coded with varying combinations of intensities of the fluorophores. The process also includes a third different fluorophore integrated to a reporter molecule for quantification of reactions on the surface of the encoded microspheres. The fabrication of the encoded microspheres and the system is described in, for example, Chandler, V. S., et al., "Multiplexed analysis of clinical specimens apparatus and methods", U.S. Pat. No. 5,981,180 (1999). Due to the relatively wide emission spectra of many fluorophores, a moderate number of patterns can be uniquely distinguished with this class of labels, typically less than 1000.

The use of nanoparticles with relatively narrow fluorescent emission spectra (described for example by Chandler, M. B., et al., "Microparticles attached to nanoparticles labeled with fluorescent dye", U.S. Pat. No. 6,268,222 (2001); Xu, H. et. al., "Multiplexed SNP genotyping using the Qbead™ system"; a quantum dot-encoded microsphere-based assay, Nucleic Acids Research 31(8), e43 (2003)). Encoding particles with other optical markers, e.g. electrochemically deposited codes (described for example by Nicewarner-Pena, S. R. et al., "Submicrometer metallic barcodes", *Science* 294, 137–141 (2001); and Walton, I. D. et al., "Particles for multiplexed analysis in solution: detection and identification of striped metallic particles using optical microscopy", *Anal. Chem.* 74, 2240–2247 (2002)) can improve the multiplicity of the assay while retaining the operational advantages of particle-based assays.

The present invention relies on the interaction between light and particles possessing defined physical and optical properties. More specifically, resonant light scattering from spherical particles (interchangeably referred to herein as resonant Mie scattering because the interaction of light with the particles used in the present invention is described by Mie theory) is used to determine either or both the particle identity and the degree of binding of target species the particle surface. Theories of interactions between light and particles are provided in many references, for example Bohren, C. F., and Huffman, D. R., *Absorption and Scattering of Light By Small Particles*, John Wiley and Sons (1983); Kerker, M., *The Scattering of Light and Other Electromagnetic Radiation*, Academic Press (1969). More specifically pertaining to the present invention are treatments of resonance structures in the resonant light scattering spectrum, see for example Chylek, P. et al., "Narrow resonance structure in the Mie scattering characteristics", *Appl. Optics* 17, 3019–3021 (1978); Conwell, P. R. et al., "Resonant spectra of dielectric spheres", *J. Opt. Soc. America A* 1, 62–67 (1984); Probert-Jones, J. R., "Resonance component of backscattering by large dielectric spheres", *J. Opt. Soc. America A* 1, 822–830 (1984); Hill, S. C. and Benner, R. E., "Morphology-dependent resonances associated with stimulated processes in microspheres", *J. Opt. Soc. America B* 3, 1509–1514; Lettieri, T. R., and Marx, E., "Resonance light scattering from a liquid suspension of microspheres", *Appl. Optics* 25(23), 4325–4331 (1986); Chylek, P. and Zhan, J., "Interference structure of the Mie extinction cross section", *J. Opt. Soc. America A* 6, 1846–1851 (1989); and Hill, S. C. et al., "Structural resonances observed in the fluorescence emission from small spheres on substrates", *Appl. Optics* 23, 1680 (1984). The development of computational methods and computer algorithms for deriving structure and property information from scattered light is described in, for example, Conwell, P. R. et al., "Efficient automated algorithm for the sizing of dielectric microspheres using the resonance spectrum", *J. Opt. Soc. America A* 1, 1181–1186 (1984); Lam, C. C. et al., "Explicit asymptotic formulas for the positions, widths, and strengths of resonances in Mie scattering", *J. Opt Soc. America B* 9, 1585–1592 (1992); Chylek, P., "Resonance structure of Mie scattering: distance between resonances", *J. Opt. Soc. America A* 7, 1609–1613 (1990); and Guimaraes, L. G., and Nussenzveig, H. M., "Uniform approximation to Mie resonances", *J. Modern Optics* 41, 625–647 (1994). Of further specific relevance to the microparticles of this invention are treatments of layered spheres, for example Kaiser, T. and Schweiger, G., "Stable algorithm for the computation of Mie coefficients for scattered and transmitted fields of a coated sphere", *Computers in Physics* 7, 682–686 (1993); and Hightower, R. L. and Richardson, C. B., "Resonant Mie scattering from a layered sphere", *Appl. Optics* 27, 4850–4855 (1988).

In practical applications, resonant light scattering has been used for particle size and refractive index measurements, studies of atmospheric aerosols, interstellar particles, and other measurements; for example see the two articles cited above for Conwell (1984) and Lettieri (1986); also see Ray, A. K. and Nandakumar, R., "Simultaneous determination of size and wavelength-dependent refractive indices of thin-layered droplets from optical resonances", *Appl. Optics* 34, 7759–7770 (1995); Huckaby, J. L., et al., "Determination of size, refractive index, and dispersion of single droplets from wavelength-dependent scattering spectra", *Appl. Optics* 33, 7112–7125 (1994); Hill, S. C., et al., "Sizing dielectric spheres and cylinders by aligning measured and computed resonance locations: algorithm for multiple orders", *Appl. Optics* 24, 2380–2390 (1985); Chylek, P. V. et al., "Simultaneous determination of refractive index and size of spherical dielectric particles from light scattering data",

*Appl. Optics* 22, 2303–2307 (1983), and the references therein. In these references it is shown that accurate detection of fine resonance features in the scattered light spectrum requires detection methods with high spectral resolution. Typical experimental relative error in measuring the wavelength position of peaks in the earlier reports, e.g. Chylek et al., (1983) is about 1 part in $10^5$. More recently, for example in Huckaby (1994), the relative precision of peak determination is between about 1 part in $2 \times 10^6$ and 1 part in $2 \times 10^7$.

Whitten et al., in "Morphological resonances for multicomponent immunoassays", *Appl. Optics* 34, 3203–3207 (1995), describe a technique for distinguishing among antibody-coated microspheres based on their sizes as measured by resonance features in their fluorescence spectrum. The technique reported in that article was capable of distinguishing among a low number of subpopulations of particles (two in the example reported), each subpopulation having a nominal mean diameter, with relatively large differences between the two subpopulations in mean diameter (6.5 and 10 micrometers). In essence, particle diameter was used as an identifying label, the diameter being measured by fitting the observed resonance pattern with theoretical calculations. As disclosed in that article, the diameter "label" could only distinguish between two subpopulations differing substantially in mean diameter. No extension of this approach to identifying large, diverse populations of very similar microparticles is taught in that disclosure. Moreover, the methods and system of the present invention also differ substantially from the method and system taught in the Whitten et. al. disclosure. That disclosure teaches a fluorescence detection method in which the incident light is fixed in wavelength and the optical resonances occur in the scanned fluorescence spectrum. In contrast, a preferred embodiment of the present invention does not rely on fluorescence, uses a scanned incident wavelength, and detects a scattered light spectrum through means differing substantially from what is disclosed by Whitten et al.

Vollmer et al. in "Protein detection by optical shift of a resonant microcavity". *Appl. Phys. Lett.* 80, 4057–4059 (2002) describe the detection of protein binding to a dielectric microparticle based upon a shift in optical resonances in the particle. The resonances were excited by evanescent coupling to an eroded optical fiber and were detected as dips in the light intensity transmitted through the fiber. The detection method described in that disclosure is not based on light scattering measurements. Moreover, the possibility of using the optical resonances for particle identification is not taught by Vollmer et al.

Hightower, R. L. and Richardson, C. B, supra, used theoretical modeling to compute the resonant response of large, layered spheres to an incident linearly polarized plane wave. Based on the results of these computations, they suggest that the sharp and unique features of the scattered light spectrum may be used in studies of immiscible fluids, adsorbed layers, coatings, and vesicles. However, use of resonant light scattering spectra for identification of microparticles or for detection in biological and chemical assays is not taught in that disclosure.

Serpenguzel et al. in "Excitation of resonances of microspheres on an optical fiber", *Optics Lett* 20, 654–656 (1995) describe the measurement of resonant light scattering of solid microspheres that are excited using evanescent coupling to an optical fiber. The authors of that disclosure postulate that the measurement of these light scattering resonances may be used for performing extremely sensitive adsorption and reaction measurements between species bonded to the microsphere surface and reagents in the surrounding solution. However, how such measurements could be made is not taught in that disclosure. Moreover, the possibility of using the optical resonances for particle identification is not taught by Serpenguzel et al.

Arnold et al. in U.S. patent application Publication No. 2003/0174923 describe a method and system for detecting a substance based on a resonance shift of photons orbiting within a microsphere of a sensor. The microsphere is coupled with at least one optical fiber such that the microsphere is excited by evanescent coupling to the fiber. The resonances are detected as dips in the light intensity transmitted through the optical fiber. The detection method described in that disclosure is not based on light scattering measurements. That disclosure also teaches that a plurality of microspheres may be used for multianalyte detection. However, in that disclosed method, the microspheres are kept in a fixed position attached to the optical fiber. The possibility of using optical resonances as signatures for particle identification for use in tracking the particles, and therefore the attached probes, is neither taught nor suggested by Arnold et al.

In contrast to the reports in the literature, the basis for identification of microparticles in the present invention is to effectively use the very rich information content inherent in the resonant light scattering pattern. As will be disclosed in more detail later in this application, a resonant light scattering pattern may be characterized by a diverse set of variables including but not limited to peak location, peak width, peak order, periods between peaks of different orders, and polarization-dependent spectral properties. Distinguishable resonant light scattering patterns may be realized among members of a large set of similar microparticles by varying, from particle to particle, one or more of the main parameters affecting the scattering pattern, namely the structure, composition, and dimensions of the particle. Thus, according to the present invention a very rich and diverse set of scattering patterns among members of a large population of similar microparticles is created, providing a means to distinguish and identify individual microparticles.

The principal drawbacks to existing labeling techniques include limited multiplicity, i.e., limited combinations of unique identifying features, difficulties in preparing the encoded particles, speed and accuracy of decoding, and, in some cases, cost. There is a need therefore, for a method for parallel, simultaneous, particle-based measurement of binding kinetics for moderate to large numbers of analytes. Specifically, a method is needed that exhibits one or more of the following attributes: (1) the ability to measure binding without need of external reporter moieties; (2) the ability to determine quantitatively the binding of a target analyte in real time; (3) the ability to optionally amplify the binding signal; and (4) the ability to identify and optionally track individual microparticles. Each of these represents a distinct improvement over the current practice, and taken together, provide not only improved speed, accuracy, and cost reduction for existing assays, but also enable new applications not previously possible.

The present invention solves the stated problem by providing reliable, easily manufacturable, and cost-effective methods of particle identification and binding detection, capable of high multiplicity and superior in performance to current practice. In the present invention, the microparticles are identified by a novel application of high-resolution light scattering, employing specific features in the scattering spectrum as unique identifying patterns or optical signatures. Specifically, the present invention employs resonant light scattering, also known as resonant Mie scattering, as the analytical method for both determining a particle's identity and also for determining the presence of, and optionally the degree of binding to the surface of the particle. These methods may be used together, or separately, to afford assays that are substantially improved over the state of the art.

SUMMARY OF THE INVENTION

The present invention provides methods of identifying analytes bound to particles on the basis of unique light scattering resonance patterns that identify the particle and differences between the those patterns pre and post binding. Accordingly the invention provides a method for the identification of an analyte comprising:
- (a) providing a light scanning source which produces light over an analytical wavelength range;
- (b) providing at least two substantially spherical identifiable particles;
- (c) applying at least one capture probe to the particles of (b) which binds to the surface of the particle, the at least one capture probe having affinity for at least one analyte;
- (d) scanning each particle of (c) one or more times over a first analytical wavelength range to produce at least one first reference resonant light scattering signature for each particle of (c), said first resonant light scattering signature uniquely identifying each particle;
- (e) correlating the at least one capture probe with each identified particle of (d);
- (f) contacting the particle of (e) with a sample suspected of containing at least one analyte where, if the analyte is present in said sample, binding occurs between the at least one capture probe and the at least one analyte;
- (g) scanning the particles of (f), one or more times over a second analytical wavelength range to produce at least one second binding resonant light scattering signature for each particle of (f), wherein:
  1) the at least one first reference and at least one second binding resonant light scattering signatures may be the same or different; and
  2) the at least first and second analytical wavelength ranges may be the same or different;
- (h) detecting binding of the at least one analyte to the at least one capture probe by comparing the differences between the resonant light scattering signatures selected from the group consisting of: any of the at least one first reference light scattering signature and any of the at least one second light scattering signature; and
- (i) identifying one or more bound analytes on the basis of the correlation made in step (e) and the at least one second binding resonant light scattering signature.

In an alternate embodiment the invention provides a method for the identification of an analyte comprising:
- (a) providing a light scanning source which produces light over an analytical wavelength range;
- (b) providing at least two substantially spherical identifiable particles;
- (c) applying at least one capture probe to the particles of (b) which binds to the surface of the particle, the at least one capture probe having affinity for at least one analyte;
- (d) affixing the particles of (c) in a defined spatial array wherein each particle has a defined locus;
- (e) optionally scanning the particles of (d) one or more times over the analytical wavelength range to produce at least one first reference resonant light scattering signature for each particle of (d);
- (f) contacting the particle of (e) with a sample suspected of containing at least one analyte where, if the analyte is present, binding occurs between the at least one capture probe and the at least one analyte;
- (g) scanning the particles of (f) one or more times over the analytical wavelength range to produce at least one second binding resonant light scattering signature for each particle of (f);
- (h) detecting binding of the at least one analyte to the at least one capture probe by comparing the differences between the resonant light scattering signatures selected from the group consisting of: any of the at least one first reference light scattering signature and any of the at least one second light scattering signature; and
- (i) identifying one or more bound analytes on the basis of the affixed particle locus.

In similar fashion the invention provides a method for the identification of an analyte comprising:
- (a) providing light scanning source which produces light over an analytical wavelength range;
- (b) providing at least two substantially spherical identifiable particles;
- (c) applying at least one capture probe to the particles of (b) which binds to the surface of the particle, the at least one capture probe having affinity for at least one analyte;
- (d) scanning each particle of (c) one or more times over the analytical wavelength range to produce at least one first reference resonant light scattering signature for each particle of (c), said first resonant light scattering signature uniquely identifying each particle;
- (e) correlating the at least one capture probe with each identified particle of (d);
- (f) contacting the particle of (e) with a sample suspected of containing at least one analyte where, if the analyte is present, binding occurs between the at least one capture probe and the at least one analyte, the analyte comprising a detectable label; and
- (g) identifying one or more analytes on the basis of the correlation of step (e) and the detectable label of the analyte.

In another embodiment the invention provides a method for the detection of analyte binding to a capture probe comprising:
- (a) providing a light scanning source which produces light over an analytical wavelength range;
- (b) providing at least one substantially spherical identifiable particle;
- (c) applying at least one capture probe to the particles of (b) which binds to the surface of the particle, the at least one capture probe having affinity for at least one analyte;
- (d) optionally scanning the particles of (c) one or more times over the analytical wavelength range to produce at least one first reference resonant light scattering signature for each particle of (c);
- (e) contacting the particle of (d) with a sample suspected of containing at least one analyte where, if the analyte is present, binding occurs between the at least one capture probe and the at least one analyte;
- (f) scanning the particles of (e) one or more times over the analytical wavelength range to produce at least one second binding resonant light scattering signature for each particle of (e); and
- (g) detecting binding of the at least one analyte to the at least one capture probe by comparing the differences between the resonant light scattering signatures selected from the group consisting of: any of the at least one first reference light scattering signature and any of the at least one second light scattering signature.

In an alternate embodiment the invention provides method for the detection of analyte dissociation from a capture probe comprising:
(a) providing a light scanning source which produces light over an analytical wavelength range;
(b) providing at least one substantially spherical identifiable particle comprising:
1) at least one capture probe affixed to the particle and;
2) at least one analyte bound to the at least one capture probe;
(c) scanning the particle of (b) one or more times over the analytical wavelength range to produce at least one first reference resonant light scattering signature for said particle;
(d) dissociating the at least one analyte from the at least one capture probe of the particle of step (c);
(e) scanning the particle of (d) one or more times over the analytical wavelength range to produce at least one second dissociation resonant light scattering signature for each particle; and
(f) detecting dissociation of the at least one analyte from the at least one capture probe by comparing the differences between the resonant light scattering signatures selected from the group consisting of: any of the at least one first reference light scattering signature and any of the at least one second light scattering signature.

Additionally the invention provides an identifiable particle comprising:
(a) a substantially spherical core;
(b) a capture probe affixed to the outer surface of the particle;
wherein:
1) the particle is characterized by a unique resonant light scattering signature when scanned over an analytical wavelength range of about 1 to about 20 nanometers over a range of optical wavelengths of about 275 nanometers to about 1900 nanometers;
2) the particle is about 100 micrometers in diameter or less;
3) the particle has a refractive index between about 1.6 and about 2.1 over the analytical wavelength range; and
4) the particle is substantially non-fluorescing over the analytical wavelength range.

In a specific embodiment the invention provides An identifiable particle comprising:
(a) a substantially spherical core;
(b) a capture probe affixed to the outer surface of the particle;
wherein:
1) the particle is characterized by a unique resonant light scattering signature when scanned over an analytical wavelength range of about 1 to about 20 nanometers over a range of optical wavelengths of about 275 nanometers to about 1900 nanometers;
2) the particle is about 100 micrometers in diameter or less;
3) the particle has a refractive index between about 1.6 and about 2.1 over the analytical wavelength range; and
4) the particle is substantially non-fluorescing over the analytical wavelength range;
wherein the particle comprises:
i) one or more optically active layers having a thickness between about 50 nanometers and about 20 micrometers; and
ii) one or more biologically active or chemically active substantially transparent outer layers of thickness between about 1 nanometer to 10 micrometers, said layers overlaying the layer of (i).

Additionally the invention provides microparticle based measuring systems comprising:
(a) at least one substantially spherical identifiable particle in solution, each particle comprising a capture probe affixed to the outer surface of the particle;
wherein:
1) the particle is characterized by a unique resonant light scattering signature when scanned over an analytical wavelength range having a window spanning about 1 to about 20 nanometers, over a range of optical wavelengths from about 275 to about 1900 nanometers;
2) the particle is about 75 micrometers in diameter or less; and
3) the particle has a refractive index between about 1.45 and about 2.1 over the analytical wavelength range.
(b) a light scanning source for scanning the particle over the analytical wavelength range;
(c) an optical cell for presenting the particle in a suitable position and in a suitable environment for detecting scattered light;
(d) a particle handling means for placing particles into the optical cell; and
(e) a detection means for detecting light from the scanned particle and converting said light to an electrical signal.

BRIEF DESCRIPTION OF THE FIGURES AND SEQUENCE DESCRIPTIONS

The invention can be more fully understood from the following detailed description, figures and the accompanying sequence descriptions, which form a part of this application.

FIG. 1 is a schematic representation of a particle-based specific binding assay according to the invention, showing the capture of selected targets from a multi-analyte sample and the non-binding of targets not complementary to one of the probes.

FIG. 2 is a drawing of a layered microparticle showing a core coated with an arbitrary number of m layers. The core and each layer are characterized by a radius R and a refractive index n. Particle-to-particle variations in R and n give rise to unique scattered light patterns that can be used to identify each particle according to the invention.

Figure 7:
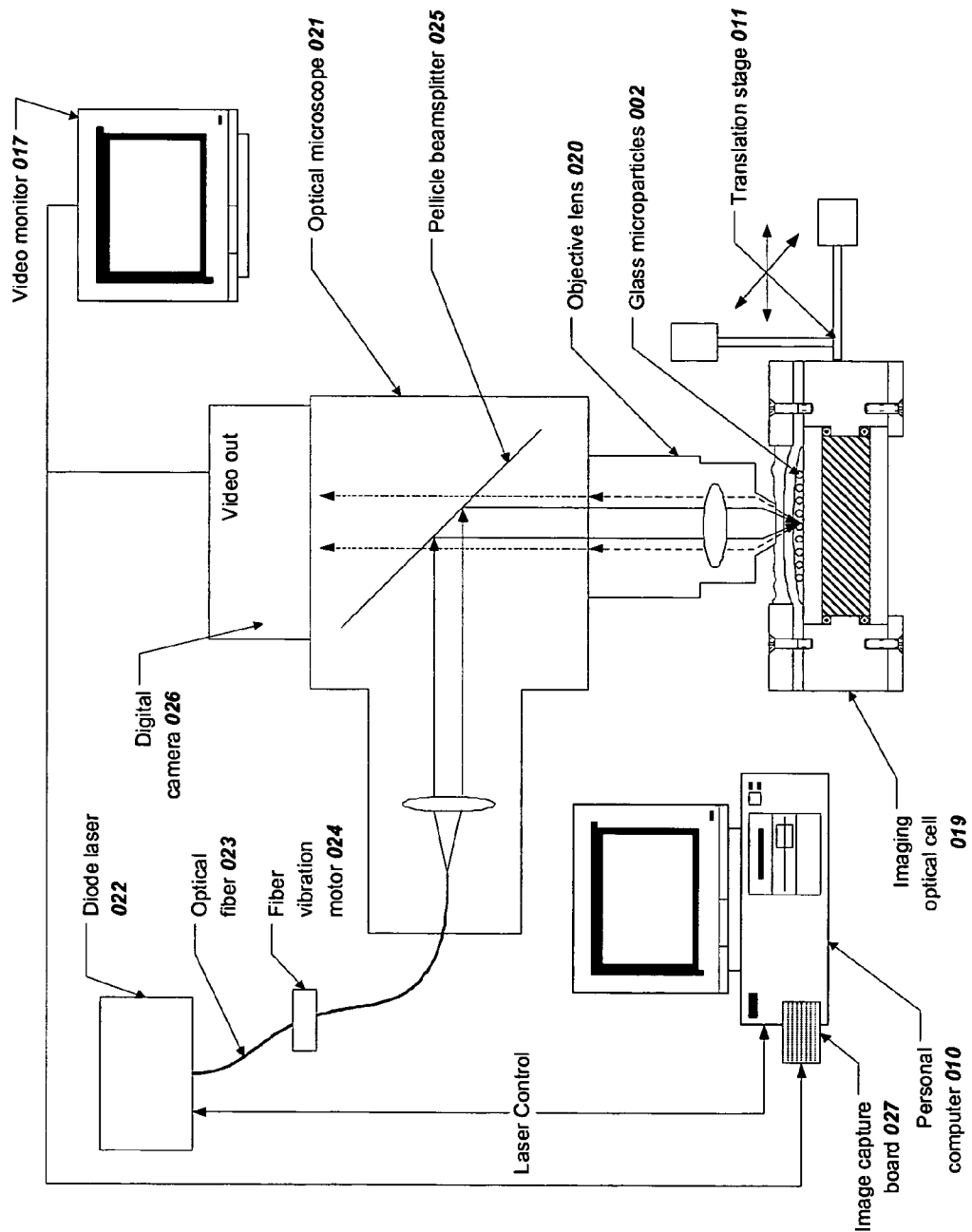
FIG. 7 is a schematic diagram of the imaging detection systems used to measure scattered light from a multiplicity of microparticles according to the invention. The components are not drawn to scale.

FIG. 8 is a digital image of scattered light from a group of microparticles, acquired by the imaging detection system of FIG. 7 at a single wavelength of incident light. Both the incident and scattered light were polarized; the directions of the polarization were parallel. The numbers 12, 3, 6, and 9 refer to regions of the scattered light image for each particle as explained in the text.

Figure 9:
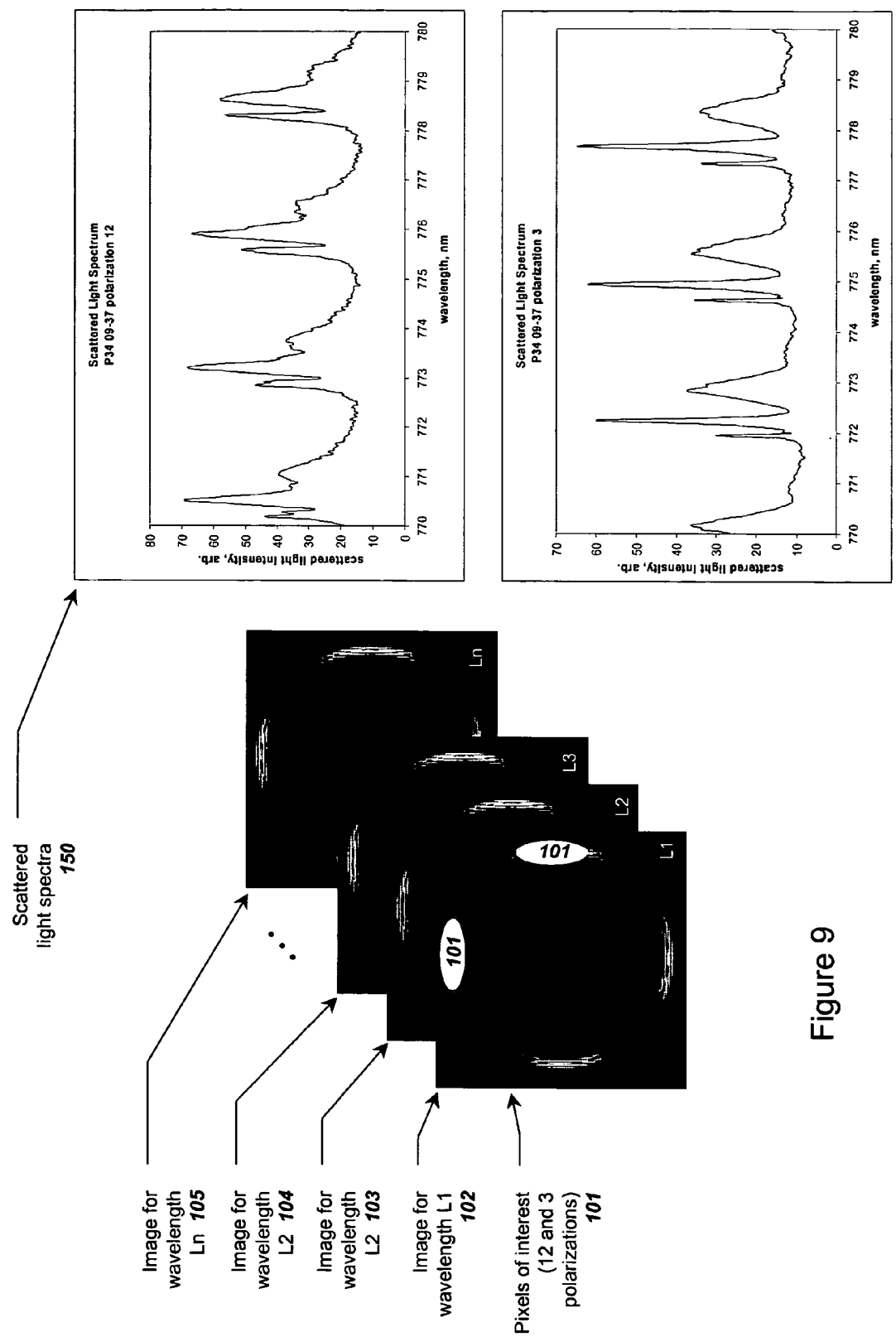

FIG. 9 is a set of wavelength-linked scattered light images from a single particle and the extracted scattered light spectra from two regions of interest (polarization 12 and polarization 3).

Figure 10C:
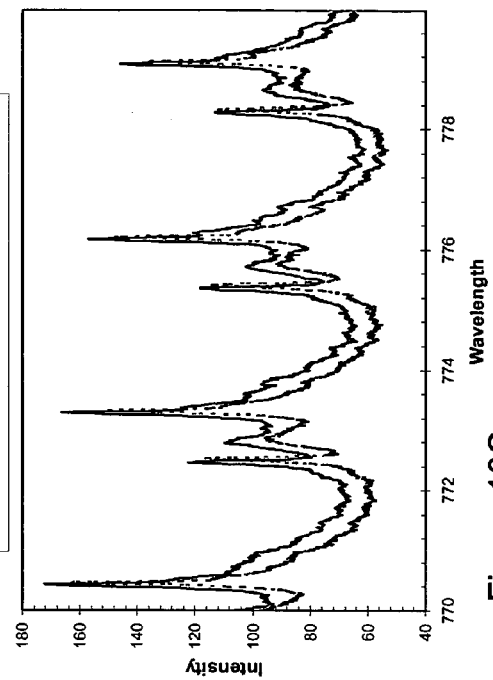
Figure 10B:
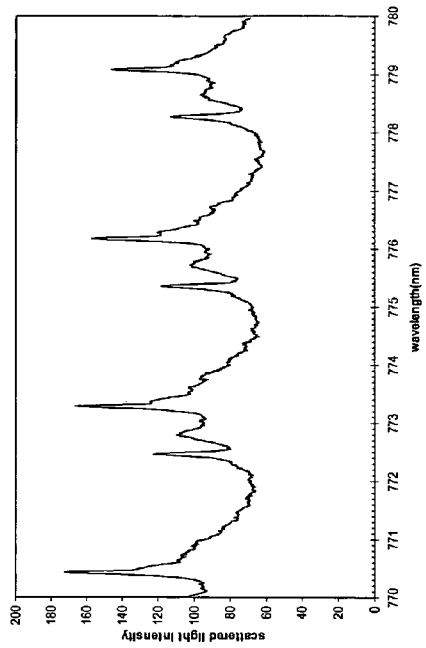
Figure 10A:
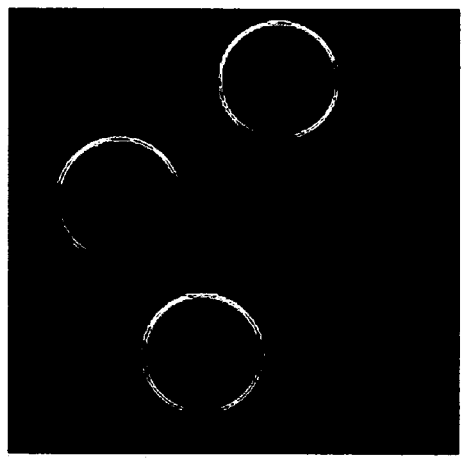

FIG. 10A is a digital image of scattered light from biotinylated glass microparticles according to Example 3.

FIG. 10B is a scattered light spectrum of a biotinylated microparticles according to Example 3.

FIG. 10C shows a comparison of scattered light spectra before and after binding of avidin on a biotinylated microparticle according to Example 3.

Figure 11:
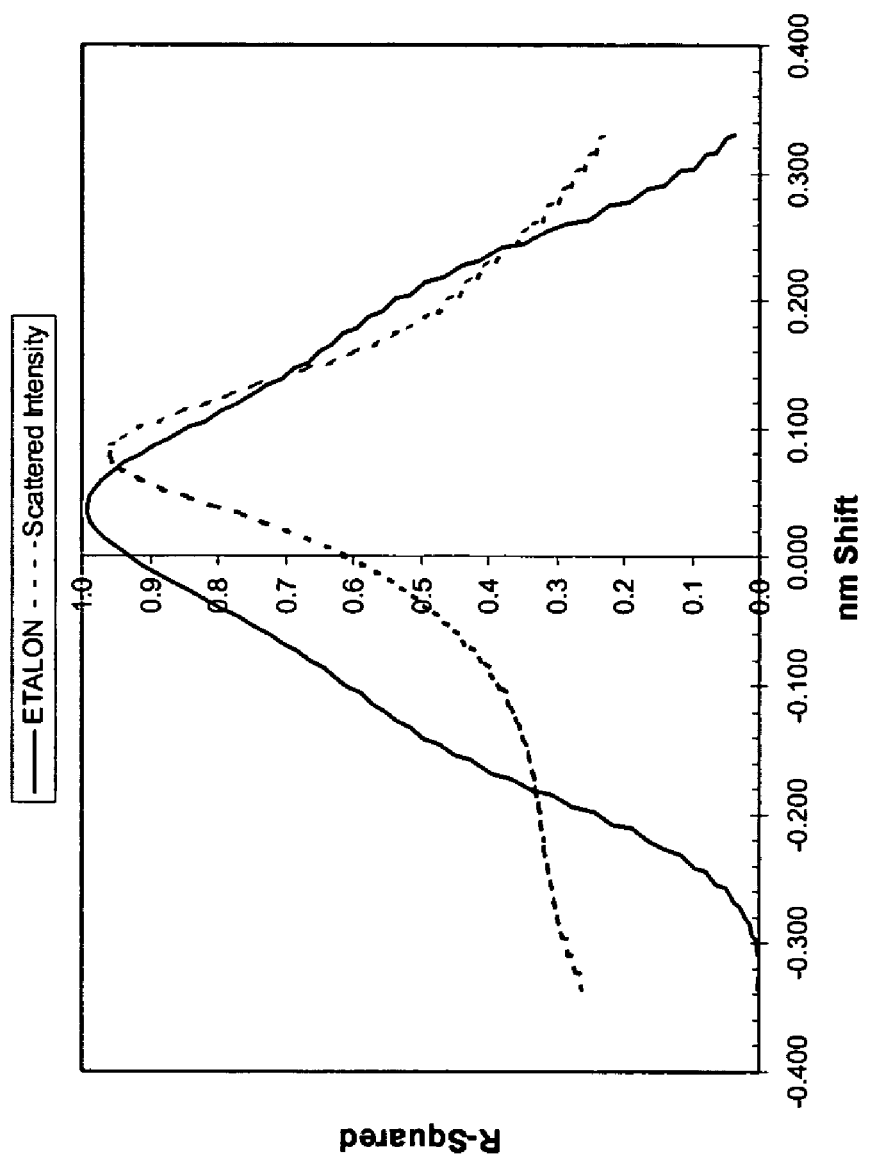

FIG. 11 shows the autocorrelation function for the etalon data and the scattering spectra shown in FIG. 10C, as described in Example 3.

Figure 12:
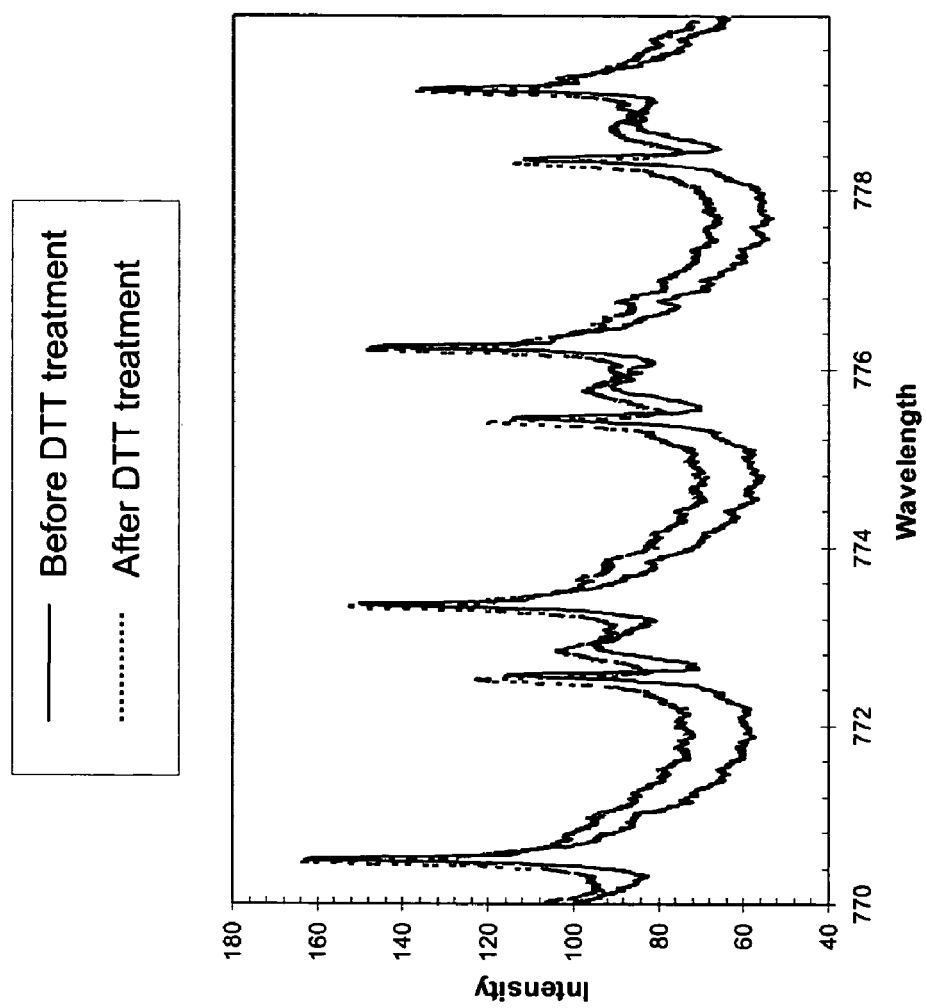

FIG. 12 shows the spectrum shift obtained after DTT treatment on the same microparticle shown in FIG. 10C, as described in Example 3.

Figure 13:
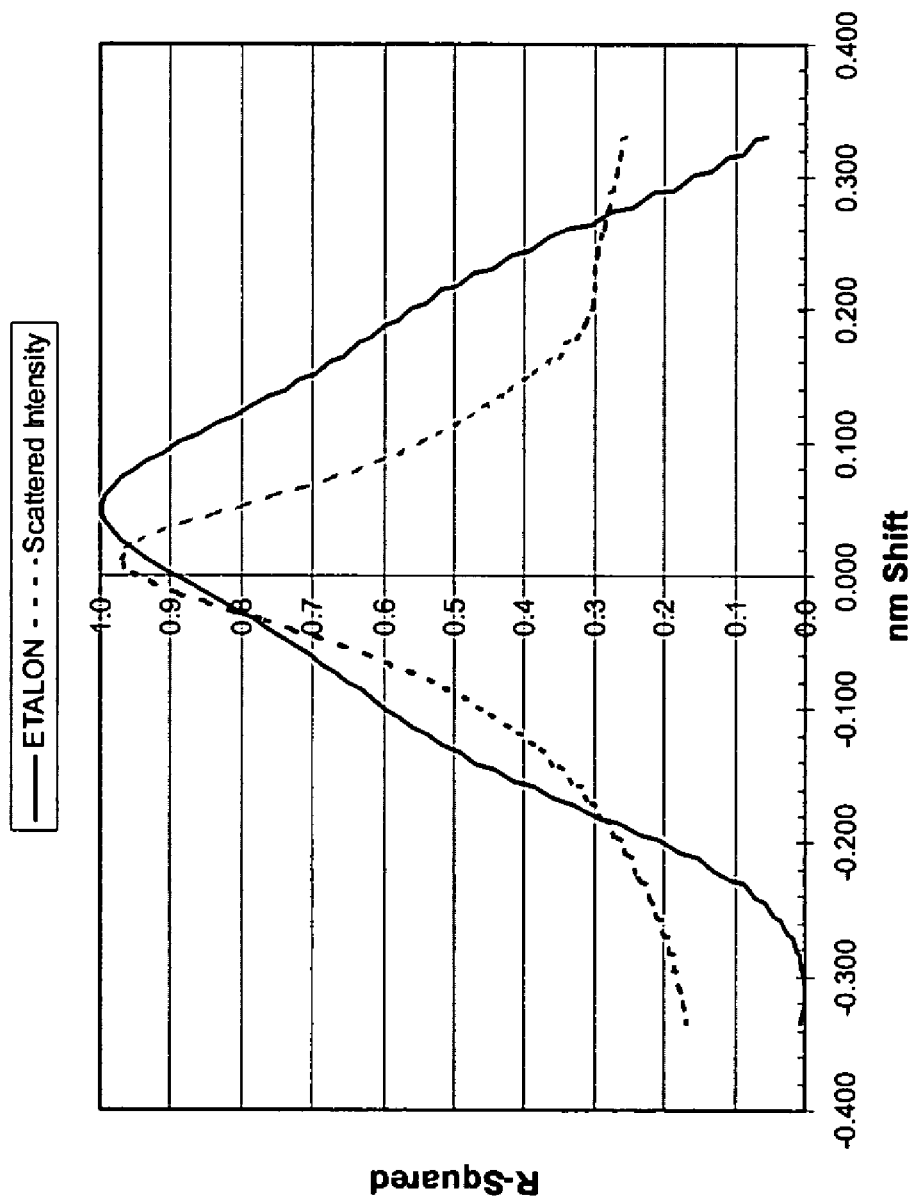

FIG. 13 shows the autocorrelation functions for the etalon data and the scattering spectra shown in FIG. 12, as described in Example 3.

Figure 14A:
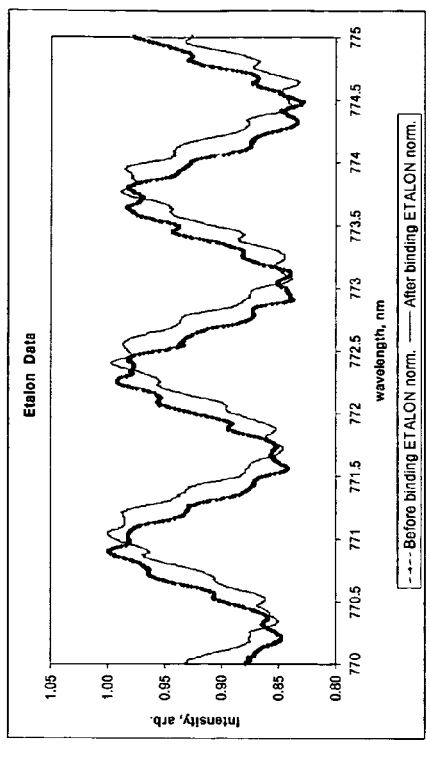

FIG. 14A shows examples of two scattered light spectra taken before and after binding of an analyte. The wavelength scales have not yet been accurately aligned.

Figure 14B:
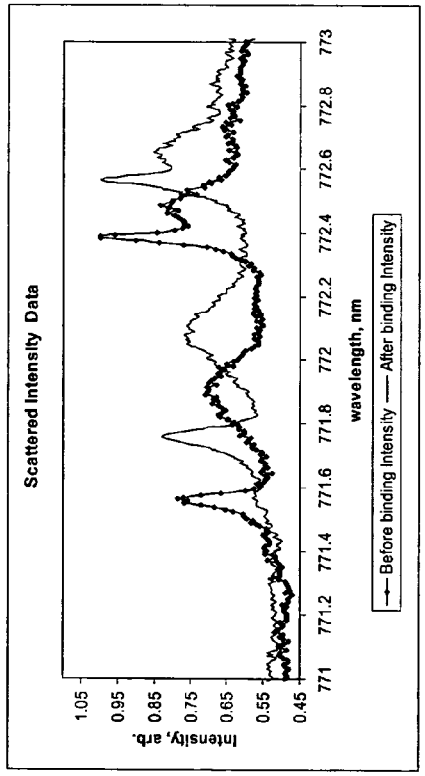

FIG. 14B shows the interference patterns from two stacked etalons obtained during the spectral scans of FIG. 14A.

Figure 14C:
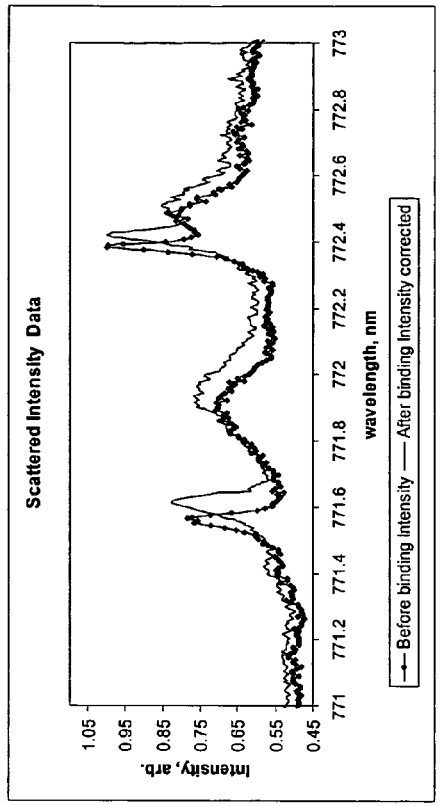

FIG. 14C shows the correlation analysis of the scattered light spectra (intensity) and of the etalon patterns (ETALON).

Figure 14D:
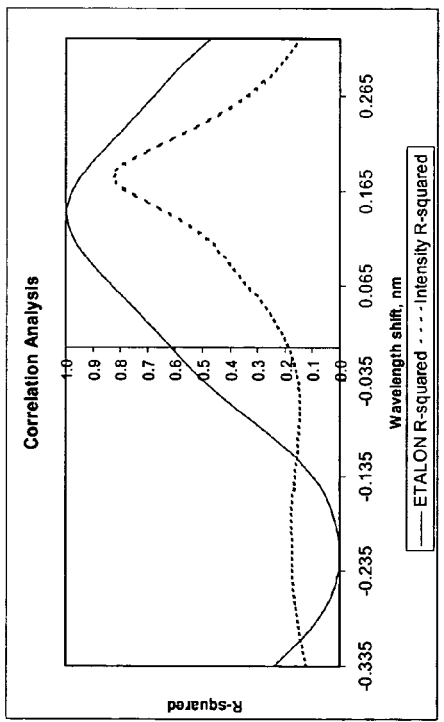

FIG. 14D shows the wavelength-corrected scattered light spectra before and after binding of an analyte with etalon alignment, as described in Example 3.

Figure 15:
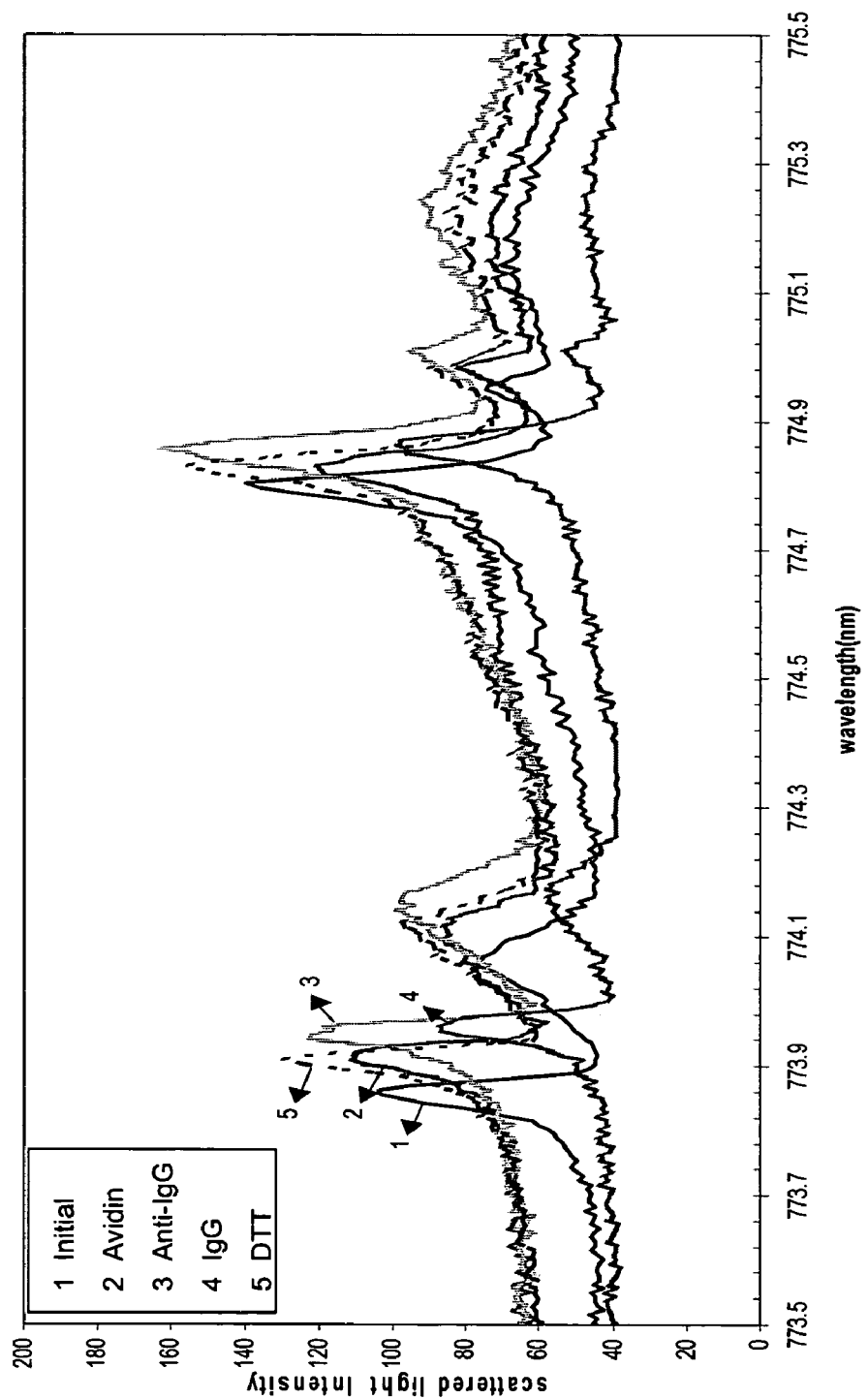

FIG. 15 shows the scattering spectra of a single microparticle for the sequential binding steps of the sandwich assay and the subsequent cleavage with DTT, as described in Example 4.

Figure 16:
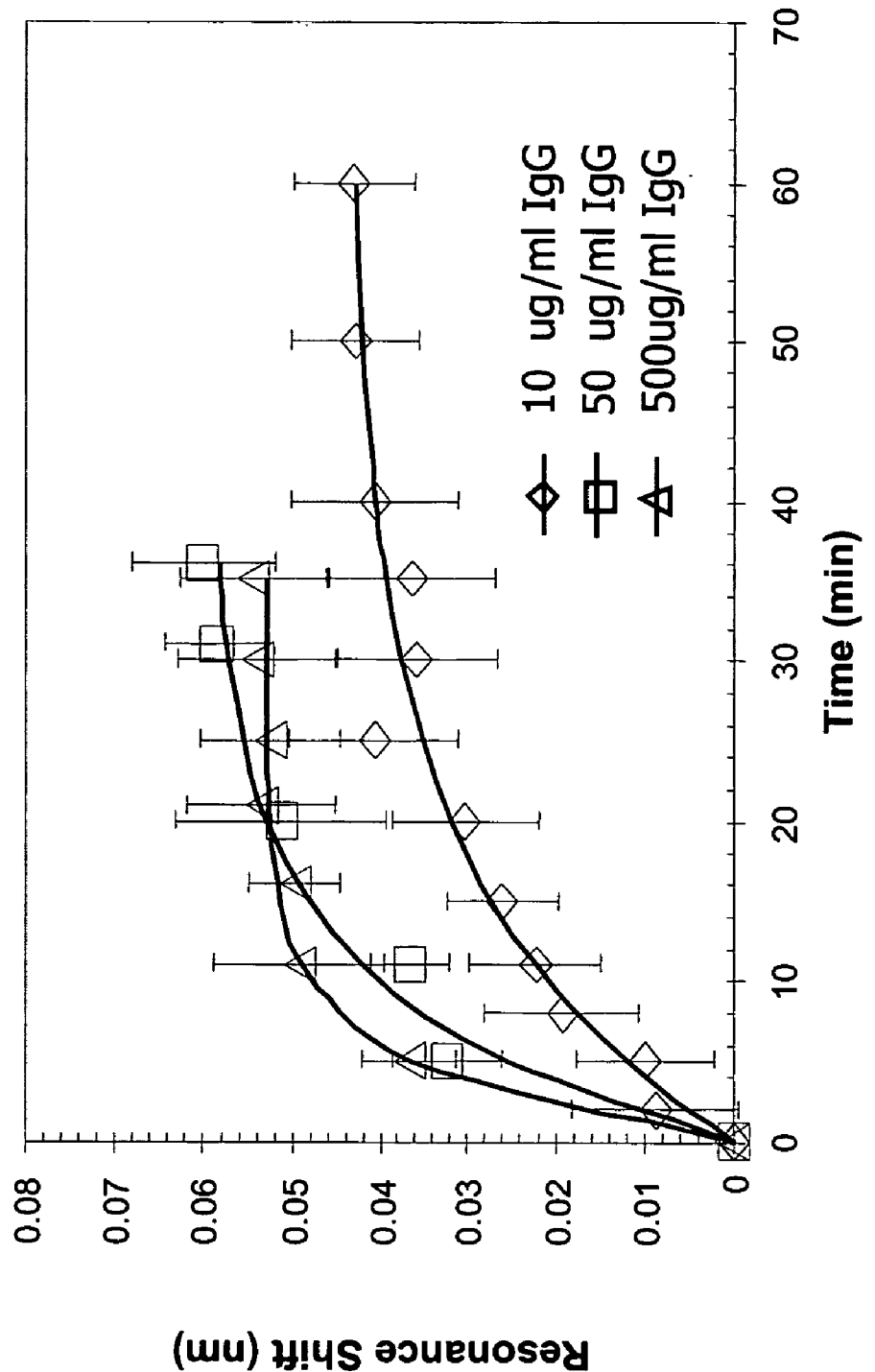

FIG. 16 shows the change in resonance wavelength with time upon IgG binding to Protein G' microparticles, as described in Example 6.

Figure 17:
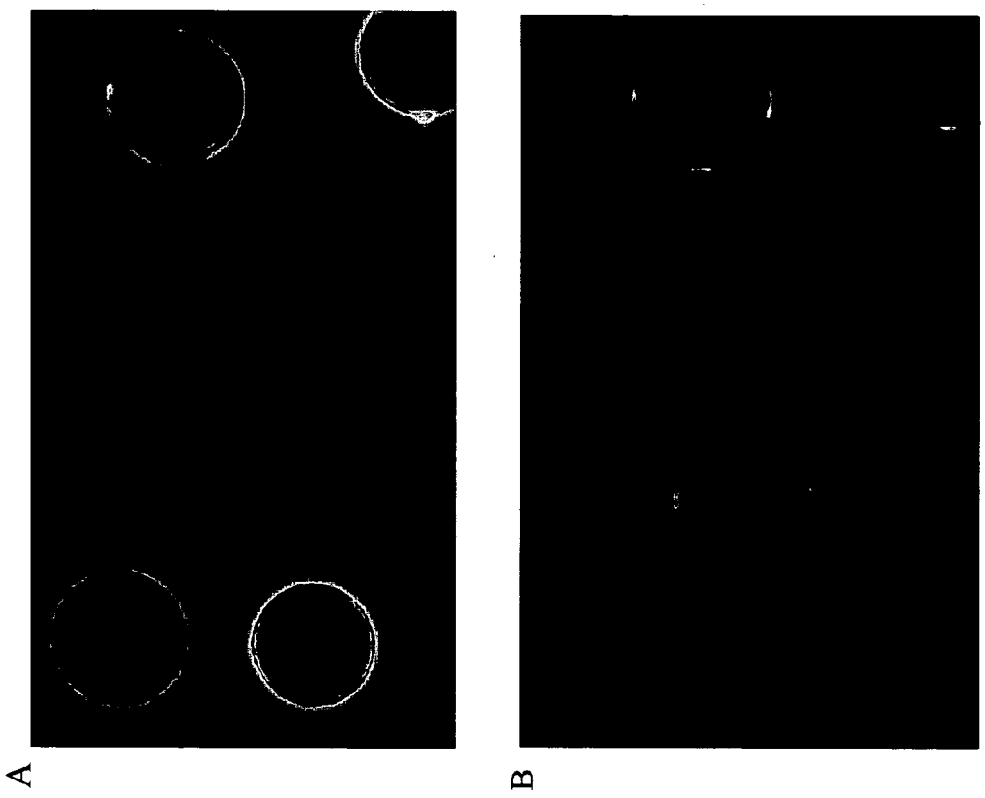

FIG. 17 shows the image of a group of microparticles under Argon ion laser illumination to show the fluorescent microparticles (A) and under diode laser illumination to show the plain view of the same area (B), as described in Example 8.

FIGS. 18 and 19 show the predicted resonant light scattering spectra of the microparticles described in Example 14.

Figure 21:
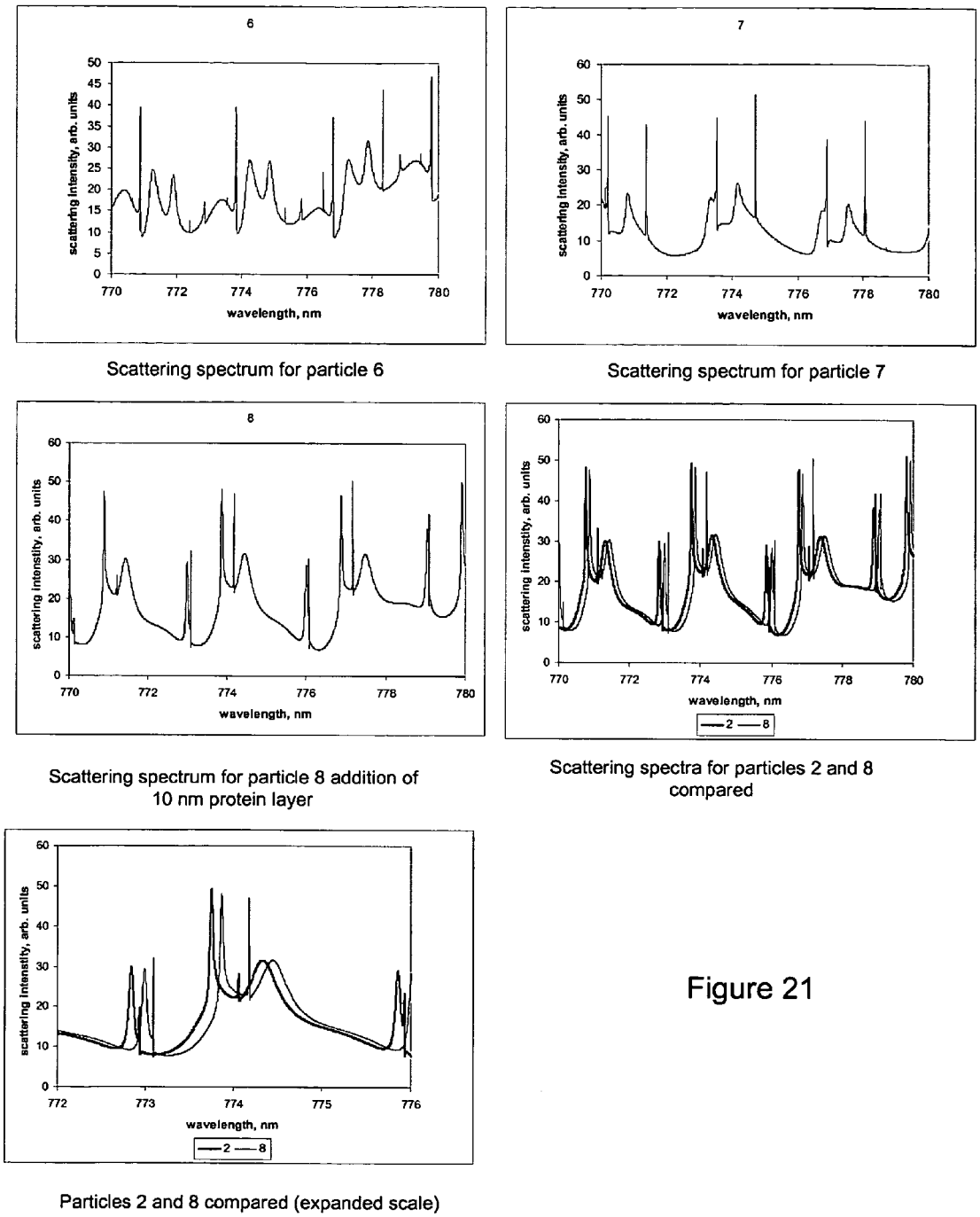

FIGS. 20 and 21 show the predicted resonant light scattering spectra of the microparticles described in Example 15.

FIGS. 22 and 23 show the predicted resonant light scattering spectra of the microparticles described in Example 16

FIG. 24 shows the predicted resonant light scattering spectra of the microparticles described in Example 17.

Figure 26:
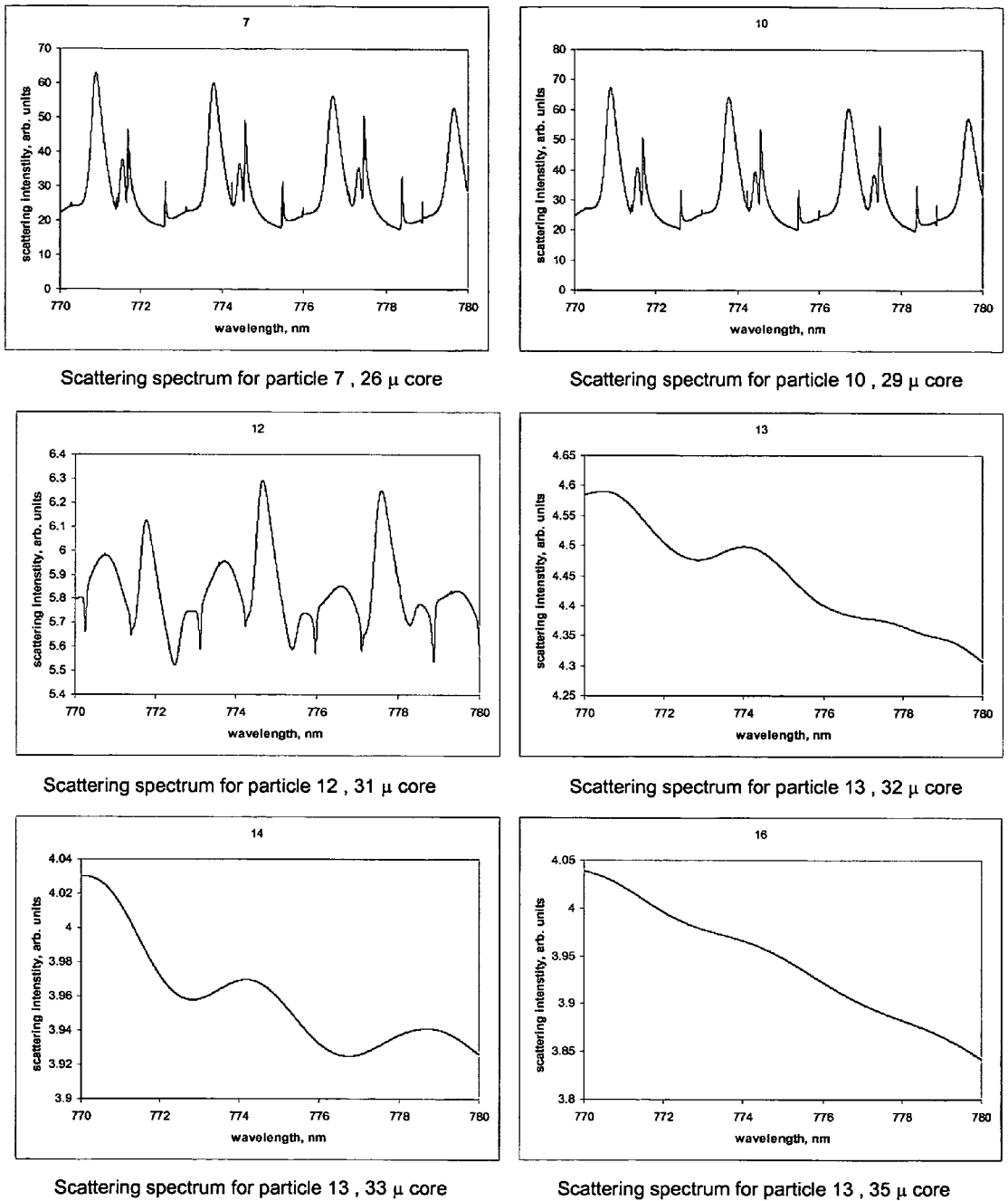
Figure 27:
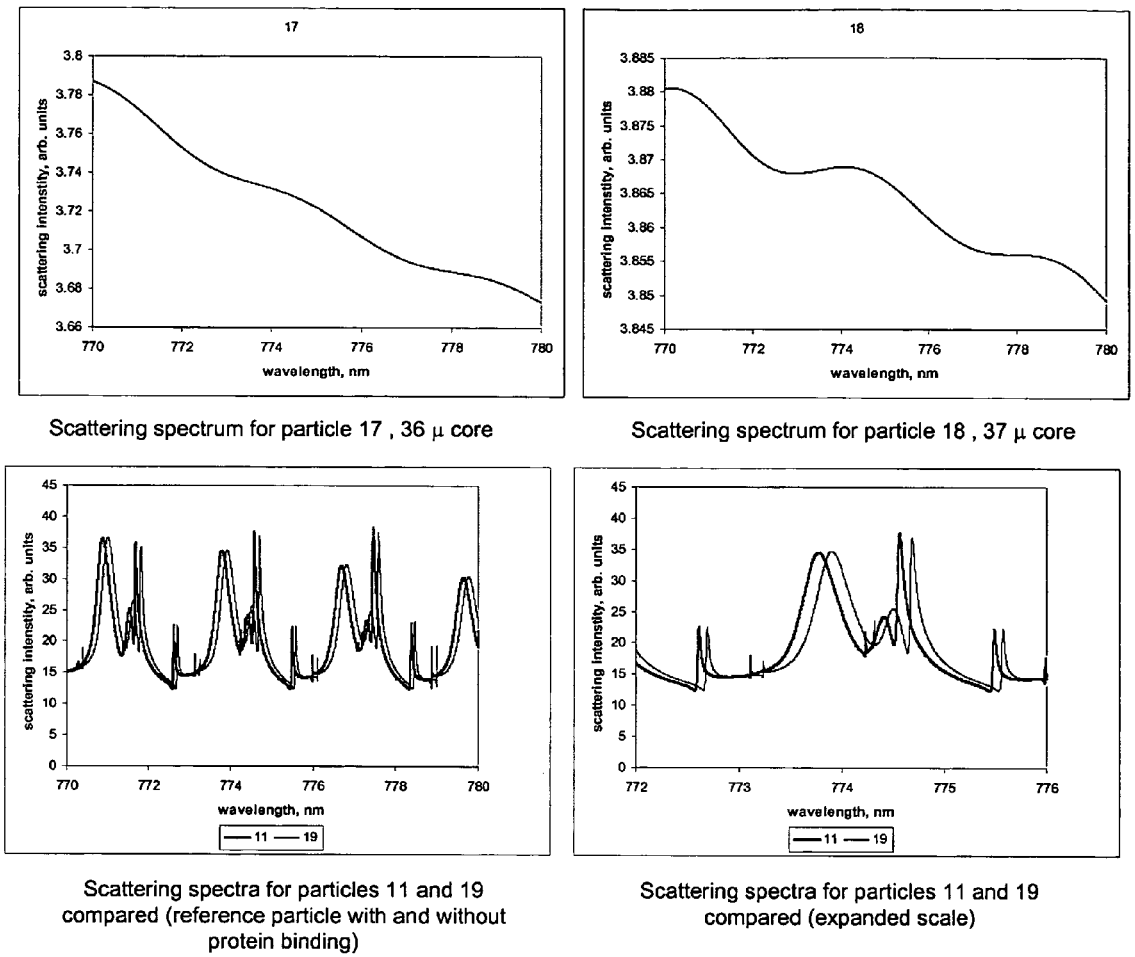

FIGS. 25–27 show the predicted resonant light scattering spectra of the microparticles described in Example 18.

FIGS. 28 and 29 show the predicted resonant light scattering spectra of the microparticles described in Example 19.

Figure 31:
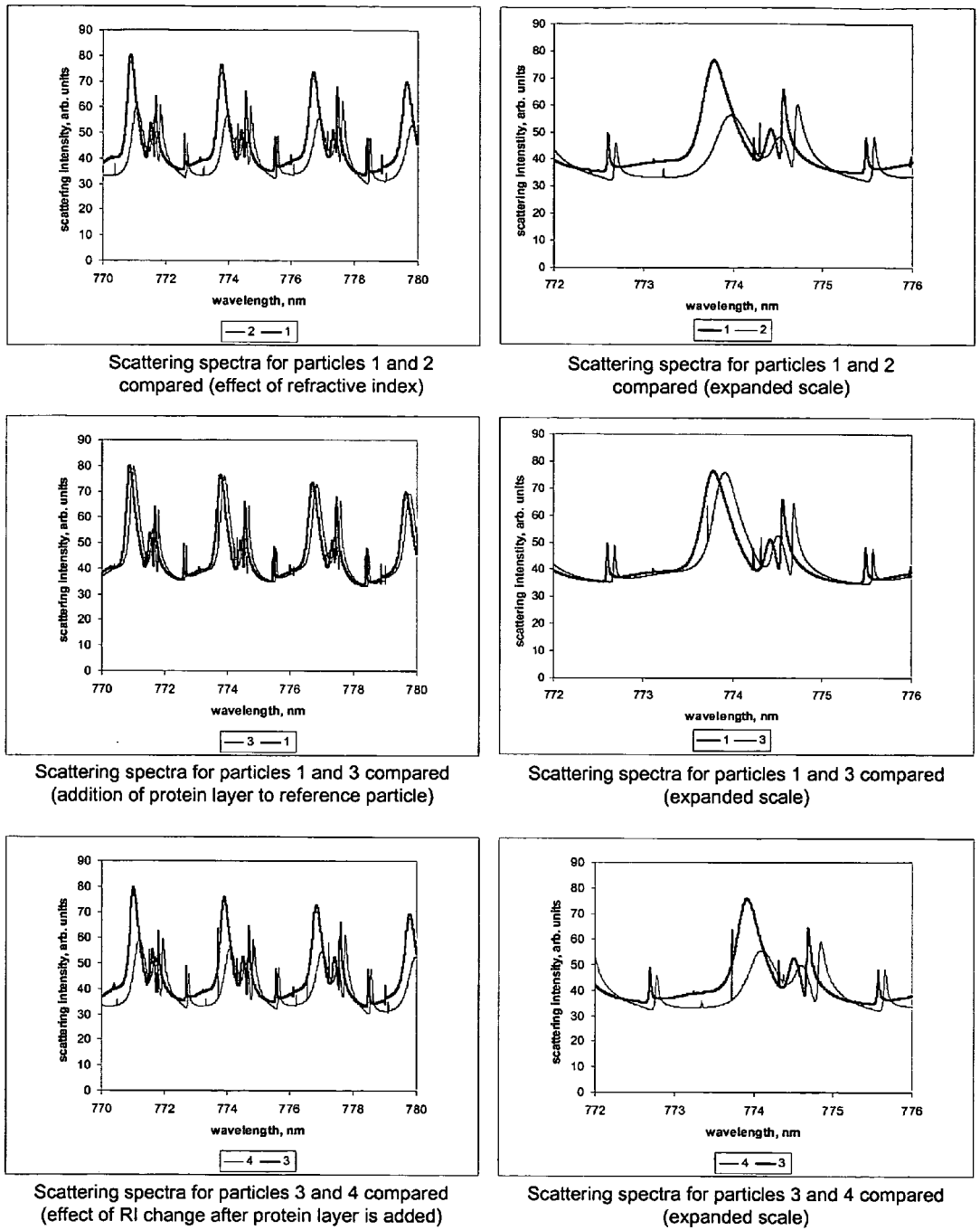
Figure 35:
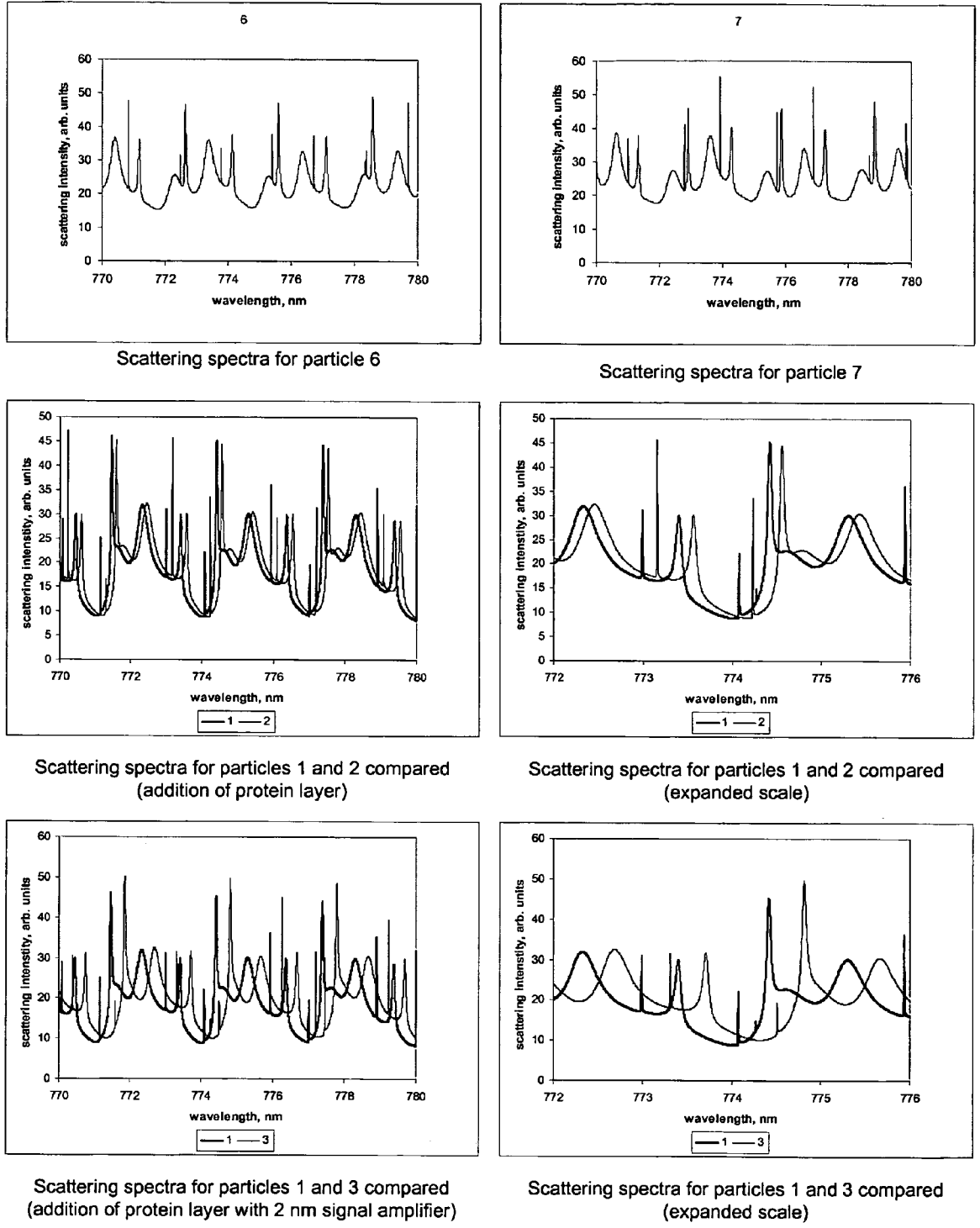

FIGS. 30 and 31 show the predicted resonant light scattering spectra of the microparticles described in Example 20.

FIGS. 32 and 33 show the predicted resonant light scattering spectra of the microparticles described in Example 21.

FIGS. 34–37 show the predicted resonant light scattering spectra of the microparticles described in Example 22.

The following sequences conform with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the synthetic foot and mouth disease target described in Example 9.

SEQ ID NO:2 is the nucleotide sequence of the JBP oligonucleotide probe described in Example 9.

SEQ ID NO:3 is the nucleotide sequence of the modified JBP S2SP3B oligonucleotide probe described in Example 9.

SEQ ID NO:4 is the nucleotide sequence of the N-JBC oligonucleotide probe described in Example 9.

SEQ ID NO:5 is the nucleotide sequence of the fluorescein-labeled oligonucleotide target JBC-F described in Example 9.

SEQ ID NO:6 is the nucleotide sequence of the fluorescein-labeled oligonucleotide target control Lac2-F described in Example 9.

SEQ ID NO:7 is the nucleotide sequence of the fluorescein-labeled oligonucleotide target JBP-F described in Examples 9 and 11.

SEQ ID NO:8 is the nucleotide sequence of the foot and mouth disease PCR fragment JB described in Example 10.

SEQ ID NO:9 is the nucleotide sequence of the Lac2-511 PCR nonspecific target fragment described in Example 10.

SEQ ID NOs:10–13 are the nucleotide sequences of oligonucleotide primers used to amplify the PCR target fragments as described in Example 10.

SEQ ID NO:14 is the nucleotide sequence of the peptide nucleic acid probe JBP2C described in Example 11.

SEQ ID NO:15 is the nucleotide sequence of the modified peptide nucleic acid probe JBP2BC described in Example 11.

SEQ ID NO:16 is the nucleotide sequence of the compliment of the JB PCR product described in Example 12.

SEQ ID NO:17 is the nucleotide sequence of the fluorescein-labeled oligonucleotide probe JBP-S2SP3F described in Example 13.

DETAILED DESCRIPTION OF THE INVENTION

The invention provides reliable, easily manufacturable, and cost-effective methods of specific analyte detection and particle identification, which is capable of parallel analysis with high multiplicity, and is superior in performance to current methods. In the present invention, the microparticles are identified by a novel application of high-resolution light scattering, employing specific features in the scattering spectrum as unique identifying patterns or optical signatures. Specifically, the present invention employs resonant light scattering as the analytical method for both determining a particle's identity and also for determining the presence of and optionally the degree of binding to the surface of the particle. According to the present invention, when an analyte binds to a specific microparticle, the optical properties of the microparticle are changed in a way that enables the determination of the degree of binding while retaining the ability to identify the microparticle and thus the analyte of interest.

The present invention advances the art by providing a system that is unique in: (1) the structure, physical properties, and functionality of the particles; (2) the ability to measure binding without need of external reporter moieties; (3) the means of identifying the particles; (4) the ability to determine quantitatively the binding of a target analyte in real time; and (5) the ability to optionally amplify the signal.

The following definitions are used herein and should be referred to for interpretation of the claims and the specification.

As used in this disclosure, the singular forms "a", "an", and "the" may refer to plural articles unless specifically stated otherwise. Thus, for example, references to a method of manufacturing, derivatizing, or treating "a particle" may include a mixture of one or more particles. Furthermore, the use of grammatical equivalents of articles such as "beads", "particles", "microparticles" and "microspheres" are not meant to imply differences among these terms unless specifically indicated in the context.

The terms "particle", "microparticle", "bead", "microsphere", and grammatical equivalents refer to small discrete particles, preferably, substantially spherical in shape, having a diameter less than about 100 micrometers, preferably less than about 75 micrometers, more preferably less than about 50 micrometers.

The term "identifiable microparticle" refers to a microparticle that may be identified and optionally tracked.

The terms "spectral features", "optical resonance structures", "identification features", "scattering resonances", and "resonant light scattering signatures" are used interchangeably herein to refer to features in the resonant light scattering spectrum that may be used for particle identification, including, but not limited to peak location, peak width, peak order, periods between peaks of different orders, and polarization-dependent spectral properties.

The terms "protein", "peptide", "polypeptide" and "oligopeptide" are herein used interchangeably to refer to two or more covalently linked, naturally occurring or synthetically manufactured amino acids.

The term "analyte" refers to a substance to be detected or assayed by the method of the present invention. Typical analytes may include, but are not limited to proteins, peptides, nucleic acids, peptide nucleic acids, antibodies, receptors, molecules, biological cells, microorganisms, cellular organelles, cell membrane fragments, bacteriophage, bacteriophage fragments, whole viruses, viral fragments, and one member of a binding pair.

The terms "target" and "target analyte" will refer to the analyte targeted by the assay. Sources of targets will typically be isolated from organisms and pathogens such as viruses and bacteria or from an individual or individuals, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components). Additionally, targets may be from synthetic sources.

The term "binding-pair" includes any of the class of immune-type binding-pairs, such as, antigen/antibody, antigen/antibody fragment, or hapten/anti-hapten systems; and also any of the class of nonimmune-type binding-pairs, such as biotin/avidin, biotin/streptavidin, folic acid/folate binding protein, hormone/hormone receptor, lectin/specific carbohydrate, enzyme/enzyme enzyme/substrate, enzyme/inhibitor, or, vitamin B12/intrinsic factor. They also include complementary nucleic acid fragments (including DNA sequences, RNA sequences, and peptide nucleic acid sequences), as well as Protein A/antibody or Protein G/antibody, and polynucleotide/polynucleotide binding protein. Binding pairs may also include members that form covalent bonds, such as, sulfhydryl reactive groups including maleimides and haloacetyl derivatives, and amine reactive groups such as isothiocyanates, succinimidyl esters, carbodiimides, and sulfonyl halides.

The terms "capture probe", "probe", "binding agent", "bioactive agent", "binding ligand", or grammatical equivalents, refer to any chemical or biological structure or moiety, for example protein, polypeptide, polynucleotide, antibody or antibody fragment, biological cells, microorganisms, cellular organelles, cell membrane fragments, bacteriophage, bacteriophage fragments, whole viruses, viral fragments, organic ligand, organometallic ligand, and the like that may be used to bind either non-specifically to multiple analytes, or preferentially, to a specific analyte or group of analytes in a sample.

The term "probe-coupled microparticle" refers to a microparticle which has a capture probe attached to the surface.

The term "ligand" or "reactive ligand" refers to a chemical moiety or "label" that can act as one member of a binding pair, including but not limited to antibodies, lectins, receptors, binding proteins, nucleic acids, or chemical agents.

The term "label" refers to any atom or molecule that can be attached to a nucleic acid, protein or a member of a binding-pair. A label may be coupled to binding-pair or nucleic acid through a chemically reactive group. A label may be attached to an oligonucleotide during chemical synthesis or incorporated on a labeled nucleotide during nucleic acid replication. Labels will include but are not limited to fluorescent moieties, chemiluminescent moieties, particles, enzymes, radioactive tags, quantum dots, light emitting moieties, light absorbing moieties, and intercalating dyes including propidium iodide (PI) and ethidium bromide (EB) and the cyanine dyes (see for example, U.S. Pat. No. 5,563,037).

The term "reporter" refers to any atom or molecule that is used as a "label" to provide a detectable (preferably quantifiable) signal, and which can be attached to a nucleic acid, protein or a member of a binding-pair. Reporters may provide signals detectable by fluorescence, chemiluminescence, radioactivity, colorimetry, X-ray diffraction or absorption, magnetism, enzymatic activity, and the like.

The term "reporter conjugate" refers to a conjugate comprising a "reporter-label" coupled to one member of a binding-pair such as an antibody, lectin, receptor or binding protein or other moiety which can bind to an analyte.

The term "oligonucleotide", refers to polydeoxyribonucleotides (containing 2-deoxy-D-ribose), to polyribonucleotides (containing D-ribose) and to any polynucleotide, which is a ribo sugar-phosphate backbone consisting of an N-glycoside of a purine or pyrimidine base, or modified purine or pyrimidine base. There is no intended distinction between the length of a "nucleic acid", "polynucleotide" or an "oligonucleotide".

The term "peptide nucleic acid" or "PNA" refers to an analogue of DNA that has a pseudo-peptide backbone, rather than the sugar-phosphate backbone of nucleic acids (DNA and RNA). PNA mimics the behavior of DNA and binds complementary nucleic acid strands.

The term "oligomer" refers to any probe or target made up of two or more monomers and is used herein to describe the structure of a nucleic acid, peptide, peptide nucleic acid, or any polymer used in the context of the present invention. The preferred use of the term is in reference to the structure of peptide nucleic acids (PNA), similar to "oligonucleotide," which contains a sequence of "nucleobase" moieties on the pseudopeptide backbone that mimics the ribo sugar-phosphate backbone of nucleic acids.

The term "nucleobase" refers to the purine or pyrimidine moiety of DNA, RNA or PNA.

The term "primer" is used generally to mean any sequence-binding oligonucleotide which functions to initiate the nucleic acid "replication" process or "amplification" process.

The term "replication" refers to the process in which a complementary strand of a nucleic acid strand of the nucleic acid molecule is synthesized by a polymerase enzyme. In a "primer-directed" replication, this process requires a hydroxyl group (OH) at 3' position of (deoxy)ribose moiety of the terminal nucleotide of a duplexed "primer" to initiate replication.

The term "amplification" refers to the process in which "replication" is repeated in cyclic process such that the number of copies of the nucleic acid sequence is increased in either a linear or logarithmic fashion. Such replication processes may include but are not limited to, for example, Polymerase Chain Reaction (PCR), Ligase Chain Reaction (LCR) Strand Displacement Amplification (SDA) or other such enzymatic reactions.

The term "primer directed nucleic acid amplification" or "primer-directed amplification" refers to any method known in the art wherein primers are used to sponsor replication of nucleic acid sequences in the linear or logarithmic amplification of nucleic acid molecules. Applicants contemplate that primer-directed amplification may be accomplished by any of several schemes known in this art, including but not limited to the polymerase chain reaction (PCR), ligase chain reaction (LCR) or strand-displacement amplification (SDA).

The term "complementary strand" refers to a nucleic acid sequence-strand or a peptide nucleic acid sequence strand which when aligned with the nucleic acid sequence of one strand of the target nucleic acid, such that the 5' end of the sequence is paired with the 3' end of the other sequence in antiparallel association, a stable duplex is formed. Complementarity need not be perfect. Stable duplexes may be formed with mismatched nucleotides.

A "fragment" constitutes a fraction of the DNA or RNA sequence of a particular region. A "nucleic acid fragment of interest" refers to a fragment that is incorporated within or is part of a target nucleic acid sequence and is useful as a diagnostic element.

The term "specific binding" or "specific-analyte binding" refers to affinity of a binding-pair reagent(s) for an analyte, which is a member of the binding pair.

The term "non-specific binding" refers to the non-specific affinity of the probe-microparticles for sample matrix components. In the context of the present invention, "non-specific binding" can be determined as a resonance shift that results from the non-specific affinity of the probe-microparticles for the sample matrix components when the target analyte is not present.

The term "sample matrix components" refers to any components of the sample matrix other than the target analyte. Sample matrix components include, but are not limited to proteins, lipids, salts, nucleic acids, and carbohydrates, and are typically natural components of biological samples which contain analytes.

The term "stringency" refers to the strict control of the parameters that affect the stability or the formation of a nucleic acid duplex. This can be temperature (Tm), cation concentrations ($[Na^+]$, $[K^+]$, $[Mg^{2+}]$, $[Mn^{2+}]$), the composition and number of nucleotides in the duplex or the concentration of a duplex destabilizing agents, e.g., formamide.

The term "identification of an analyte" refers to the process of determining the identity of an analyte based on its binding to a capture probe whose identity is known.

The term "analytical wavelength range" refers to a wavelength window over which the microparticles of the present invention are scanned to produce resonant light scattering signatures. The window typically has a span of about 1 to about 20 nanometers over the optical wavelengths from about 275 to about 1900 nanometers, preferably from about 600 to about 1650 nanometers. More preferably, the analytical wavelength range is a window of 10 nanometers from about 770 to about 780 nanometers. It is contemplated that a number of scans of the particles of the invention may be made during the process of identifying an analyte or analyte binding, however each of these scans will be over an "analytical wavelength range" although that range may differ from scan to scan depending on the specific object of the assay.

The term "light scanning source" refers to a source of light whose wavelength may be varied over the analytical wavelength range. Light scanning sources include sources that produce light that may be varied over the analytical wavelength range, such as scanning diode lasers and tunable dye lasers, and polychromatic sources which produce light having a range of wavelengths, such as light-emitting diodes, lamps and the like, used in conjunction with a wavelength-selecting means.

The term "reference resonant light scattering signature" refers to the resonant light scattering signature that is produced by scanning the particles of the present invention over the analytical wavelength range after the capture probe has been applied to the particles or in the case of detection of analyte dissociation from the capture probe, after the analyte has bound to the capture probe. The reference resonant light scattering signature may be used to identify the particles and the probes attached thereto and may serve as a baseline for the detection of analyte binding. A number of reference resonant signatures may be obtained by scanning the particles at different times.

The term "binding resonant light scattering signature" refers to the resonant light scattering signature that is produced by scanning the particles of the present invention over the analytical wavelength range after the particles are contacted with the analyte. A series of binding resonant light scattering signatures may be obtained to follow the binding in real time. The determination of binding is done by comparing either any one of the binding resonant light scattering signatures to any one of the reference resonant light scattering signatures or anyone of the plurality of binding resonant light scattering signatures with a previous binding resonant light scattering signature in the series.

The term "identifying resonant light scattering signature" refers to the resonant light scattering signature that is produced by scanning the particles of the present invention over the analytical wavelength range before the capture probe is applied to the particles. The identifying resonant light scattering signature serves to identify the particles so that a known capture probe may be attached and its identity correlated with the identified particle.

The term "dissociation resonant light scattering signature" refers to the resonant light scattering signature that is produced by scanning the particles of the present invention over the analytical wavelength range after the analyte is dissociated from the capture probe. A series of dissociation resonant light scattering signatures may be obtained to follow the dissociation in real time. The determination of dissociation is done by comparing either any one of the dissociation resonant light scattering signatures to any one of the reference resonant light scattering signatures or anyone of the dissociation resonant light scattering signatures with a previous second dissociation resonant light scattering signature in the series.

The term "optically active" as applied to layers on a particle means that the layers support the production of additional or altered light scattering resonances which are associated with the particle The term "biologically active" as applied to layers on a particle means that the layers has the ability to participate in interactions among biological moieties.

The term "chemically active" as applied to layers on a particle means that the layers has the ability to participate in interactions among chemical moieties, including but not limited to binding interactions between chemical moieties. It is contemplated that such layers will have specific linker chemistry for attaching capture probes, and or may be derivatized for direct synthesis of capture probes on surface of the particles.

The present invention provides microparticle-based analytical methods, systems, and applications. A primary object of this invention is to provide improved methods for detecting the presence, and optionally the concentration, of one or more particular target analytes (for example specific nucleotide sequences or particular proteins such as antibodies or antigens), and performing the measurements without employing external reporter groups or labels. Specifically, we describe improvements in the art relating to detection of binding, particle identification, assay multiplicity, particle preparation, and end uses of the invention.

A fundamental element of the present invention is the preparation and use of microparticles having specific physical and chemical properties optimized for the measurements required in biological or chemical assays. For example, chemical functionalities that serve as specific capture probes for analytes of interest may be applied to the outer surfaces of members of a group of microparticles. By "capture probe", "binding agent", "bioactive agent", "binding ligand", or grammatical equivalents, is meant any chemical structure or moiety, for example protein, polypeptide, polynucleotide, antibody or antibody fragment, organic ligand, organometallic ligand, etc. that may be used to bind either non-specifically to multiple analytes, or preferentially, to a specific analyte or group of analytes in a sample. In a typical application of the present invention, analytes of interest are exposed to an appropriately constructed set of microparticles, one or more of which having complementary capture probes exposed on their surface. Binding of the analyte occurs and is detected by a novel and sensitive technique described more fully later in this disclosure.

A key advance in the art provided by the present invention is a method for both measuring target binding and determining particle identity by novel applications of resonant light scattering. This unified measurement approach, in which resonant light scattering is used for both particle identity and binding measurement, is unique to the present invention. However, practical applications of the invention are not limited to the combination of determining identification and binding by resonant light scattering. The invention enables diverse applications, for example: using particle identification by resonant light scattering only; particle identification by resonant light scattering with binding detection by other means; and particle identification by other means with binding detection by resonant light scattering.

In one embodiment of the present invention where these novel elements are combined, each particle is assigned an identification code or label based on its unique resonant light scattering spectrum. During preparation of the microparticles, a correlation is made between the identity of each microparticle and the specific capture probe coupled to the microparticle. This correlation enables identifying the presence of one or more analytes in a mixed sample. Binding of a specific target moiety to its complementary probe is measured by changes in the resonant light scattering spectrum of the pre-identified particle or particles known to carry the complementary probe on its surface.

In another embodiment of the present invention, the detection of binding and determination of particle identity may be done independently. For example, microparticles may be derivatized with known capture probes and placed in specific fixed locations that do not change during the experiment. The identity of a given particle, and thus the probe that is exposed on its surface, is thus determined by its location. Binding measurements may be carried out by resonant light scattering techniques as described more fully later in this disclosure.

In still another embodiment, microparticles may be derivatized by combinatorial methods in which the particle identity is neither determined nor tracked. Resonant light scattering can then be used to find assay "hits" in a screening method, and the identity of the probe can be determined independently, for example by mass spectroscopy, fluorescence, optical absorbance, radioactivity, surface plasmon resonance, or other methods known in the art that use detectable labels, such as fluorescent moieties, chemiluminescent moieties, particles, enzymes, radioactive tags, quantum dots, light emitting moieties, light absorbing moieties, intercalating dyes, and members of binding pairs. A variation of this method would include tracking the particle identities throughout the combinatorial process, by either resonant light scattering as described more fully below, or by other methods known in the art.

In yet another embodiment of the present invention, microparticles may be identified and/or tracked by resonant light scattering methods, and binding measurements made using detectable labels, such as fluorescent moieties, chemiluminescent moieties, particles, enzymes, radioactive tags, quantum dots, light emitting moieties, light absorbing moieties, intercalating dyes, and members of binding pairs.

Particle Structure, Properties, and Manufacture

By "particle", "microparticle", "bead", "microsphere", and grammatical equivalents herein is meant small discrete particles. Preferably, the particles are substantially spherical in shape. The term "substantially spherical", as used herein, means that the shape of the particles does not deviate from a perfect sphere by more than about 10%. Typically, measurement of the resonant light scattering pattern is carried out by scanning the particles, i.e., irradiating the particles with light of varying wavelength, over an analytical wavelength range within an optical wavelength range, resulting in an identifying resonant light scattering signature which is used to identify the particles. Various known probes may then be applied to the particles, as described in the Capture probes and particle libraries section infra, and the identity of the probes may be correlated with the identifying resonant light scattering signature of the particles. In principle, any optical wavelength range is applicable for the measurements of this invention. Preferably, the optical wavelength range is from about 275 to about 1900 nanometers, more preferably from about 600 to about 1650 nanometers. Preferably, the analytical wavelength range has a span of about 1 nanometers to about 20 nanometers, more preferably about 10 nanometers in width. More preferably the analytical wavelength range has a span of 10 nanometers from about 770 to about 780 nanometers.

In one preferred embodiment, the particles are substantially non-fluorescing over the analytical wavelength range. The term "substantially non-fluorescing", as used herein, means that the average fluorescence signal of the particle is less than about 10% of the average elastically scattered light signal, i.e., scattered light of the same wavelength as the incident light, over the analytical wavelength range.

The particles typically consist of a substantially spherical core and optionally one or more layers. The core may vary in size and composition depending on the application, as will be described in more detail below. In addition to the core, the particle may have one or more layers to provide functionalities appropriate for the applications of interest. The thicknesses and refractive indices of layers, if present, may vary depending on the needs of the specific application and on the wavelengths of light used to make the required measurements. For example, layers may impart useful optical properties, such as giving rise to additional scattered light resonance features or changing the relative wavelength locations of features. These layers used for optical properties, herein referred to as "optically active" layers, may typically range in thickness from about 0.05 micrometers (50 nanometers) to about 20 micrometers or more, depending on the desired overall particle diameter.

Layers may also impart chemical or biological functionalities, referred to herein as chemically active or biologically active layers, and for these functionalities the layer or layers may typically range in thickness from about 0.001 micrometers (1 nanometer) to about 10 micrometers or more (depending on the desired particle diameter), these layers typically being applied on the outer surface of the particle. These layers may also include a biologically active porous structure. In the Examples of this disclosure, the particle size is appropriate for typical bioanalytical assays, using wavelengths of light in the visible to near infrared range, but the conditions of these examples are not meant to limit the invention. Using an incident wavelength of about 775 nanometers, the diameter of the particle is preferably about 100 micrometers or less.

The compositions and therefore the indices of refraction of the core and layers may vary. In a preferred embodiment, the compositions are such that the region of the particle outside of the so-called "caustic surface" (see for example Roll, G. and Schweiger, G., "Geometrical optics model of Mie resonances, *J. Opt. Soc. Am. A* 17, 1301–1311 (2000)) is substantially transparent to light at the wavelengths of interest. As used herein, "substantially transparent" means that the absorption of light within the regions of the particle in which structural resonances are produced is sufficiently small so that when the particle is illuminated with light in the analytical wavelength range, the resonances remain observable. Theoretical calculations predict that the absorption of light within the particle is sufficiently small to enable observation of resonances when the imaginary component of the refractive index of the particle or the optically active layers, given as "k", is about 0.1 or less over the analytical wavelength range. A k value of 0.1 or less over the analytical wavelength range of 770 to 780 nanometers corresponds to an absorption coefficient of about 1.6 $\mu m^{-1}$ or less.

In a more preferred embodiment, in addition to transparency at the wavelengths of interest, the index or indices of refraction of the particle are such that resonant light scattering (discussed more fully below) is manifested at the wavelengths of interest when the particle is in a substantially aqueous medium. Preferably, the particle is rugged enough to withstand the conditions required for its intended application, such as attaching binding moieties or for undergoing bioassay reactions without significant chemical or physical degradation. It is also preferable, for optical reasons, for the core to be substantially rigid, thus maintaining shape during particle handling and assay conditions.

Suitable materials for the core include substantially transparent (at the wavelengths of interest) plastics and other polymers, ceramics, glasses, minerals, and the like. Examples include, but are not limited to, standard and specialty glasses, silica, polystyrene, polyester, polycarbonate, acrylic polymers, polyacrylamide, polyacrylonitrile, polyamide, fluoropolymers, silicone, celluloses, semiconducting materials such as silicon, optically absorbing materials, metals such as gold and silver, minerals such as ruby, nanoparticles such as gold nanoparticles and quantum dots, colloidal particles, metal oxides, metal sulfides, metal selenides, and magnetic materials such as iron oxide, and composites thereof, and others, subject to the preferred physical and optical properties previously disclosed. The core could be of homogeneous composition, or a composite of two or more classes of material depending on the physical and optical properties desired.

The core may serve a number of functions that provide utility to the invention. For example, the core may be composed of a light-absorbing material, which can serve to absorb specific light rays that do not contribute to resonant light scattering, and would otherwise be refracted out of the microparticle, thus contributing to stray light and undesired background signals. Another example of utility provided by the core is the use of magnetic materials, which would impart magnetic properties to the particles such that they may be collected, screened, moved, or otherwise manipulated by external magnetic forces. A potentially useful embodiment would be to use particles with hollow cores, for example when it is desired to have particles suspended or easily moved in aqueous media, but when the layer materials are substantially denser than water. In this instance, a hollow core could impart a decreased density to the overall particle.

In a preferred embodiment, the microparticle is composed of a core comprising a uniform glass microsphere. In a more preferred embodiment, the microparticle is composed of an optical quality glass microsphere with index of refraction between about 1.45 and 2.1, more preferably between about 1.6 and 2.1 at the wavelengths of interest previously disclosed. Suitable particles are commercially available, for example from Mo-Sci Inc. (Rolla, Mo.).

As disclosed more fully below and in the Examples, variations in the index of refraction of the core may impart desirable optical or physical properties. Accordingly, in another preferred embodiment, the core may have indices of refraction or other properties that vary with location, for example with radial distance from the center.

As previously stated in this disclosure, the microparticle may, in addition to the core, include one or more layers. The purposes for including layers in the microparticle may vary. A layer may provide suitable surfaces for attaching chemical functionalities including bioactive agents or chemical binding sites, for reducing nonspecific binding, and for protecting the physical and chemical integrity of the core. Details regarding the preparation of outer bioactive or chemically active layers are given in the section "Capture probes and particle libraries", of this disclosure. As will be disclosed more fully below, layers may also provide additional optical interfaces to increase the multiplicity of identification patterns for a population of particles.

The dimensions, compositions, and indices of refraction of the layers, if present, may vary according to the functions desired as described in the previous paragraph. In a preferred embodiment, the compositions and indices of refraction of the layers are such that all the layers are substantially transparent to light at the wavelengths of interest. The thicknesses of the layers, if present, are preferably between about 1 nanometer and 20 micrometers.

Accordingly, in another preferred embodiment, the microparticle consists of a core plus one or more layers, the combined function of the layers being to provide a suitable surface for the attachment of chemical functionalities including, for example, bioactive agents as described in the section "Capture probes and particle libraries" of this disclosure.

In another preferred embodiment, at least one layer is configured such that additional optical resonance structures are manifested, or the relative positions of the optical resonance structures are changed, when the particle is scanned over the analytical wavelength range, as will be described in more detail below.

In another preferred embodiment, the microparticle consists of a core plus a layer whose function is to provide additional or changed identification features, plus one or more additional layers, the combined function of the additional layers being to provide a suitable surface for the attachment of chemical functionalities including, for example, bioactive agents as described in the section "Capture probes and particle libraries" of this disclosure.

In still another preferred embodiment, the microparticle consists of a core plus a layer comprising a zone of varying refractive index at or near the surface of the core, said layer providing additional identification or changed features; plus one or more additional outer layers, the combined function of the additional layers being to provide a suitable surface for the attachment of chemical functionalities including, for example, bioactive agents as described in the section "Capture probes and particle libraries" of this disclosure.

Suitable materials for the layers, if present, include all the classes listed for the core, subject to constraints imposed by the desired function or functions of the layers, for example transparency at the wavelengths of interest and polyelectrolytes such as sodium poly(styrene sulfonate) and poly(diallyldimethylammonium chloride). Furthermore, the layers may be uniform in composition or they may vary in composition.

Layers can be produced on the microparticles in a variety of ways known to those skilled in the art. Examples include sol-gel chemistry techniques such as described in Iler, R. K., "Chemistry of Silica", John Wiley & Sons (1979); Brinker, C. J., and Scherer, G. W., "Sol-gel Science", Academic Press (1990). Additional approaches to producing layers on particles include surface chemistry and encapsulation techniques such as described in Partch, R. and Brown, S., "Aerosol and solution modification of particle-polymer interfaces", *J. Adhesion* 67, 259–276 (1998); Pekarek, K. et al., "Double-walled polymer microspheres for controlled drug release", *Nature* 367, 258 (1994); Hanprasopwattana, A., "Titania coatings on monodisperse silica spheres", *Langmuir* 12, 3173–3179 (1996); Davies, R., "Engineered particle surfaces", *Advanced Materials* 10, 1264–1270 (1998); and references therein. Vapor deposition techniques may also be used; see for example Golman, B. and Shinohara, K., "Fine particle coating by chemical vapor deposition for functional materials", *Trends in Chem. Engineering* 6, 1–6 (2000); and Coulter, K. E. et al., "Bright metal flake based pigments", U.S. Pat. No. 6,387,498 (2002). Still other approaches include layer-by-layer self-assembly techniques such as described in Sukhorukov, G. B. et al., "Stepwise polyelectrolyte assembly on particle surfaces: a novel approach to colloid design", *Polymers for Advanced Technologies* 9(10–11), 759–767 (1998); Caruso, F. et al., "Electrostatic self-assembly of silica nanoparticle-polyelectrolyte multilayers on polystyrene latex particles, *Journal of the American Chemical Society* 120(33), 8523–8524 (1998); Caruso, F. et al., "Investigation of electrostatic interactions in polyelectrolyte multilayer films: binding of anionic fluorescent probes to layers assembled onto colloids, *Macromolecules* 32(7), 2317–2328 (1999); Caruso, F., "Protein multilayer formation on colloids through a stepwise self-assembly technique, *Journal of the American Chemical Society* 121(25), 6039–6046 (1999); Margel, S., and Bamnolker, H., U.S. Pat. No. 6,103,379 and references cited therein.

Utility of the present invention is enhanced by using a multiplicity of microparticles. In one embodiment, the microparticles could be distributed in a two-dimensional format, for example organized in a series of tubes, grooves, channels, or other structures in a substrate, or they may be self-assembled on a surface with no specific structure. In such formats, if the particles maintain their relative positions throughout an assay, identifying the individual particles according to a pattern or label may be optional since the identities are established by position. More generally, however, the particles may be used in applications where their relative positions will vary. In this case, the particle identities may be established by resonant light scattering methods as explained more fully below, or by other techniques known in the art, such as fluorescence, optical absorbance, radioactivity and surface plasmon resonance.

It is an object of this invention to provide means for easily and cost-effectively producing a population of identifiable microparticles, suitable for use in biological and chemical assays. In any production process for the particles, there will be natural variations among the particles in the dimensions and optical properties of the core and of the layers. It is thus an object of this invention to use these natural variations, and optionally, induced variations, to provide a novel basis for particle identification. In order for the microparticles to provide utility, the variations must be controlled, or the particles appropriately screened according to their physical and optical properties. Thus, in a preferred embodiment, variations in the dimensions and optical properties of the core and/or of the layers, if present, lie within the previously disclosed preferences for a single particle. This could be accomplished in several ways, for example by adequately controlling the processes of particle production or by including a quality control screen that selects only those particles suited for use as disclosed in this invention.

Capture Probes and Particle Libraries

Capture probes may comprise various chemical classifications depending on the specific measurement of interest. Typically, they are organic or biological molecules, or molecular fragments thereof, that provide functional groups necessary for interaction with target molecules in a sample. As known in the art, the probes may have varying degrees of specificity, ranging for example from a perfect base-pair complement between a DNA probe and its target, to less stringent matching of base pairs. Similarly, probes for protein or peptide targets, for example antibodies or synthetic peptides, may be very specific, or less so depending on the structure of the probe and the assay conditions. In the discussion that follows, when "probe" or "capture probe" is used, it may refer to a chemical or physical entity with high specificity, or one or more entities with varying degrees of specificity. The probe-coupled microparticles of the present invention may be prepared by applying the capture probe of interest to the surface of the microparticles. The probe may be applied to the particles by either directly synthesizing the probe on the surface or by attaching a probe that is naturally occurring or has been synthesized, produced, or isolated separately to the surface using methods know in the art, as will be described in more detail below.

As discussed above, the utility of the invention is enhanced by using a set of microparticles, each of which has one or more unique capture probes exposed on its surface. Such a set may be generally referred to as a "library" of microparticles or probes. As known in the art, in particle-based biological assays it is generally necessary to associate a specific capture probe with a specific particle. This is typically accomplished in current practice by attaching or incorporating labels (fluorophores, chromophores, nanoparticles, etched "bar codes", etc.) to each particle. These conventional approaches may be combined with binding detection by resonant light scattering according to the present invention. However, the present invention provides for a novel and effective alternative particle identification approach that departs substantially from methods described in the literature by also using resonant light scattering to identify each particle.

One class of capture probes comprises proteins. By "protein" is meant two or more covalently linked amino acids; thus the terms "peptide", "polypeptide", "oligopeptide", and terms of similar usage in art are all to be interpreted synonymously in this disclosure. The amino acids may be either naturally occurring and/or synthetically manufactured, in any relative order and abundance. In this embodiment, hydrogen bonding, electrostatic bonding, hydrophilic interactions, and similar non-covalent binding mechanisms may be employed to provide increased binding affinity for selected targets. To increase the specificity of the binding, particular 3-dimensional structures would be preferred, as is well known in the art.

In one preferred embodiment, the capture probes are proteins or fragments thereof. Preparation of the outer bioactive layer of the microparticles for use in the present invention may include derivatizing the microparticle such that the appropriate probes may be attached to the surface, for example using linker chemistries. Methods of preparation of protein capture probe libraries and attaching probes to a surface are well known in the art, see for example Johnsson, K. and Ge, L., "Phage display of combinatorial peptide and protein libraries and their applications in biology and chemistry", *Current Topics in Microbiology and Immunology* 243, 87–105 (1999); Ruvo, M. and Fassina, G., "Synthesis and characterization of peptide libraries", in *Combinatorial Chemistry Technology*, Dekker, N.Y., pp. 7–21 (1999); Wagner, P. et al., "Arrays of protein-capture agents and methods of use thereof", U.S. Pat. No. 6,365,418 (2002); Wagner, P. et al., "Protein arrays for high-throughput screening", U.S. Pat. No. 6,406,921 (2002); McHugh, T. M., "Flow Microsphere Immunoassay for the Quantitative and Simultaneous Detection of Multiple Soluble Analytes", *Methods in Cell Biology* 42, Academic Press, 1994; Colvin, et al., in *Microspheres: Medical and Biological Applications*, 1–13, CRC Press; Illum, L. et al., "Attachment of Monoclonal Antibodies to Microspheres", *Methods in Enzymology* 112, Academic Press, 1985, and the references cited therein. Libraries of protein capture probes can be prepared, for example from plant or animal cellular extracts. Particularly useful and thus preferred are libraries of human proteins, for example human antibodies.

Protein capture probes can comprise naturally occurring polypeptides, synthetic polypeptides, or a combination of these two types. In one preferred embodiment, the capture probes are synthesized such that the amino acid sequence is partially or fully randomized using techniques known in the art, for example combinatorial biology and directed evolution methods, for example as shown in Brackmannn, S. and Johnsson, K., eds., *Directed Molecular Evolution of Proteins*, John Wiley & Sons (2002); Short, J. M. and Frey, J. F. "End selection in directed evolution", U.S. Pat. No. 6,358,709 (2002); Stuart, W. D., "Methods and compositions for combinatorial-based discovery of new multimeric molecules", U.S. Pat. No. 5,683,899 (1997), and the references cited therein.

In another preferred embodiment, the capture probes are proteins comprising partially naturally occurring amino acid sequences and partially randomized amino acid sequences.

In a another preferred embodiment, the preparation of protein capture probes, including any randomization, is carried out on the microparticle of the invention. This provides a particularly efficient approach to creating an indexed library of probes.

The optimum size or diversity of a binding library for proteins may vary depending on the particular application. The library is most useful when for a given sample, a statistically significant number of binding events occur so that the sample may be uniquely characterized. For example, a diversity of $10^7$ to $10^8$ different antibodies is considered sufficient to provide at least one combination with sufficient affinity to interact with most known antigens (see e.g. Walt, D. R. and Michael, K. L., "Target analyte sensors utilizing microspheres", U.S. Pat. No. 6,327,410 (2001)). Protein and peptide libraries used for antibody screening typically have $10^6$ to $10^8$ members or more depending on the methods used for their production (see e.g. Gavilondo, J. V. and Larrick, J. W., "Antibody Engineering at Millennium", *Bio Techniques* 29, 128–145 (2000); Hanes, J. and Pluckthun, A., "In vitro selection methods for screening of peptide and protein libraries", *Curr. Topics Microbiol. Immunol.* 243, 107–122 (1999)). Thus in one preferred embodiment, at least $10^6$, more preferably $10^7$, and most preferably $10^8$ or more different capture probes are used to screen for the presence of antigens. On the other hand, the diversity of a binding library may be reduced if the object of the measurement is to determine the presence of a smaller number of specific analytes. Assays for a limited number of specific biomarkers present in disease states such as HIV, hepatitis, cancer, and the like, are known in the art (see for example Petricoin, E. F., et al., "Use of proteomic patterns in serum to identify ovarian cancer", *Lancet* 359, 572–577 (2002)). Generally, screens for such states would therefore require fewer probes than for other applications such as large-scale genomic or proteomic mapping.

Another class of capture probes comprise nucleic acids or nucleic acid mimics (such as peptide nucleic acids described below), which may also be known as "DNA fragments", "RNA fragments", "polynucleotides", "oligonucleotides", "gene probes", "DNA probes" and similar terms used in the art, which are all to be considered synonymous in the present disclosure. Nucleic acid probes may contain nucleotide sequences from naturally occurring gene fragments, cloned gene fragments, synthetically made polynucleotides, or any combination thereof. The base sequences of synthetically made polynucleotides may be designed for a specific nucleic acid target using commercially available software, such as Oligo™ 4.0 or 6.0 (National Biosciences Inc., Plymouth, Minn.), Vector NTI (Informax™, Frederick, Md.) or other computer programs that assist in designing oligonucleotide sequence and structure. As is known in the art, the nucleotides may have the naturally occurring sugar-phosphodiester backbone, or chemical modifications thereof, these modifications allowing the use of novel chemical moieties not seen in naturally occurring genes or gene fragments.

Additionally, the capture probe may be a peptide nucleic acid (PNA) probe. PNA is an analogue of DNA that has a pseudo-peptide backbone, rather than the sugar-phosphate backbone of nucleic acids (DNA and RNA). PNA mimics the behavior of DNA and binds complementary nucleic acid strands. PNA oligomer probes may be based on the aminoethylglycin backbone with acetyl linkers to the nucleobases. They are produced with either Boc or Fmoc chemistry or solid phase synthesis using Boc/Cbz monomers (Dueholm, K. L. et al., *J. Org. Chem.* 59,5767–5773 (1994); Christensen, L. et al. *J. Peptide Sci.* 3, 175–183 (1995); Thomson, S. A. *Tetrahedron Lett.* 22, 6179–6194 (1995); Ganesh, K. N. *Curr. Org. Chem.* 4, 931–943 (2000)). PNA probes may be purchased from Applied Biosystems (Foster City, Calif.). PNA oligomers may also be designed with terminal modifiers that give functionality to the nucleic acid probe. The modifiers may also be internal to the analyte specific variable capture sequence of the PNA.

Methods for the preparation of nucleic acid probes or pseudo-nucleic acid probes, such as PNA, on particle surfaces are known. Typical references include for example Fulton, R. J., "Methods and compositions for flow cytometric determination of DNA sequences", U.S. Pat. No. 6,057,107 (2000); Chandler, M. B., et al., "Microparticles attached to nanoparticles labeled with fluorescent dye", U.S. Pat. No. 6,268,222 (2001); Chandler, V. S. et al., "Multiplexed analysis of clinical specimens apparatus and methods", U.S. Pat. No. 5,981,180 (1999); Mandecki, W., "Multiplex assay for nucleic acids employing transponders", U.S. Pat. No. 6,361,950 (2002); Mandecki, W. "Three-dimensional arrays of microtransponders derivatized with oligonucleotides. *Proceedings from the IBC Biochip Technologies Conference*, San Francisco, June 1998 D&MD Library Series publication #1941, Drug & Market Development Publications, Southborough, Mass. 01772, pp. 179–187 (1999); Brenner, S. et al., "Gene expression analysis by massively parallel signature sequencing (MPSS) on microbead arrays", *Nature Biotechnology* 18, 630–634 (2000); Brenner, S. et al., "In vitro cloning of complex mixtures of DNA on microbeads: Physical separation of differentially expressed cDNAs" *Proc. Nat. Acad. Sciences USA* 97, 1665–1670 (2000), and references therein. Alternatively, the nucleic acid probes may be prepared using standard β-cyanoethyl phosphoramidite coupling chemistry on controlled pore glass supports (Beaucage et al., *Tetrahedron Lett.* 22, 1859 (1981)) using commercially available DNA oligonucleotide synthesizers, such as that available from Applied Biosystems (Foster City, Calif.). The synthesized nucleic acid probes may then be coupled to the microparticles using covalent or non-covalent coupling, as is well known in the art. The 5' terminus, 3' terminus or both of the oligonucleotide probes may be derivatized using β-cyanoethyl phosphoramidite modifiers that give functionality to the termini of the nucleic acid probe. These modifiers include but are not limited to amino-modifiers, thio-modifiers, dithio-modifiers, carboxylic acid N-hydroxysuccinimide ester, molecular spacer modifiers, affinity reactive ligands or immuno reactive ligands. The purpose of the modifiers is to give functionality to the nucleic acid probe to allow for molecular spacing, covalent crosslinking or affinity capture of the identifiable microparticle to the probe. The cross-linking or binding functionality allows for the conjugation of the nucleic acid probe to the microparticle surfaces. Many different chemical methods known in the art may be used. These methods typically use reactive electrophilic intermediates that are capable of easily coupling to nucleophilic residues such as amine or sulfhydryl groups. These groups includes: (a) members that form covalent bonds with sulfhydryl-reactive groups including, but not limited to maleimides and haloacetyl derivatives; (b) amine-reactive groups, including but not limited to isothiocyanates, succinimidyl esters and sulfonyl halides; (c) carbodiimide-reactive groups, which include amino and carboxyl groups; (d) any of the class of immune-type binding-pairs, such as antigen/antibody or hapten/anti-hapten systems; (e) any of the class of nonimmune-type binding-pairs such as biotin/avidin, biotin/streptavidin, folic acid/folate binding protein or vitamin B12/intrinsic factor; (f) any group of complementary nucleic acid segments (including DNA sequences, RNA sequences and peptide nucleic acid sequences), and (g) any group of immunoglobulin binding proteins such as Proteins A or G. In addition to coupling properties and attributes of the functional moieties, the molecular modifiers can also contribute to the generation or amplification of the assay signature signal.

Surface preparation of microparticles useful for this invention may include for example linker chemistry, affinity capture by hybridization or by biotin/avidin affinity, combinatorial chemistry, and others known in the art. Generally, nucleic acid probes are designed to provide a nucleotide sequence complementary to a target sequence such that the binding of target is a measurable event and contributes to the characterization or screening of a sample. In this case, binding is by complementary base pairing, and need not be perfect. As is known in the art, the stringency of such binding is controllable by varying assay conditions. As disclosed previously for proteins, nucleic acid probes may consist of any combination of naturally occurring and synthetic nucleotide sequences, with the possibility of randomizing all or part of the sequence according to the needs of the specific assay.

In one preferred embodiment, the capture probes are polynucleotides or peptide nucleic acids comprising naturally occurring nucleotide sequences, for example cloned genes or gene fragments.

In another preferred embodiment, the capture probes are polynucleotides or peptide nucleic acids comprising partially naturally occurring nucleotide sequences and partially randomized nucleotide sequences.

In another preferred embodiment, the capture probes may comprise more general organic chemical structures, organic/inorganic ligands, organometallic ligands or similar complexes, useful for biosensors of diverse types, see for example Fitzgerald, D. A., *The Scientist* 16, 38 (2002); Cravatt, B. F., and Sorensen E. J. "Chemical strategies for the global analysis of protein function", *Curr. Opin. Chem. Biol.* 4, 663–668, 2000; Hergenrother, P. J., et al., "Small-Molecule Microarrays: Covalent Attachment and Screening of Alcohol-Containing Small Molecules on Glass Slides, *J. Amer. Chem. Soc.* 122(32), 7849–7850 (2000); Korbel, G. A.

et al., "Reaction Microarrays: A Method for Rapidly Determining the Enantiomeric Excess of Thousands of Samples", *J. Amer. Chem. Soc.* 123(2), 361–362 (2001); MacBeath, G. et al., "Printing Small Molecules as Microarrays and Detecting Protein-Ligand Interactions en Masse", *J. Amer. Chem. Soc.* 121(34), 7967–7968 (1999), and the references cited therein. These probe structures may be derived in many ways, including combinatorial chemistry, direct synthesis, extraction from tissues, and others.

In some applications, e.g., assays in complex biological fluids such as urine, cerebrospinal fluid, serum, plasma, and the like (see the section entitled "Assays" below) it is necessary to treat the microparticles to prevent or reduce non-specific binding of sample matrix components. Methods to reduce non-specific binding to a variety of solid supports in heterogeneous assays are well known in the art and include, but are not limited to treatment with proteins such as bovine serum albumin (BSA), casein, and non-fat milk. These treatments are generally done after the attachment of the capture probe to the microparticles, but before the assay to block the potential non-specific binding sites. Additionally, surfaces that resist non-specific binding can be formed by coating the surface with a thin film comprising synthetic polymers, naturally occurring polymers, or self-assembled monolayers that consist of a single component or a mixture of components. The thin film may be modified with adsorption-repelling moieties to further reduce non-specific binding. For example, the thin film may be a hydrophilic polymer such as polyethylene glycol, polyethylene oxide, dextran, or polysaccharides, as well as self-assembled monolayers with end functional groups that are hydrophilic, contain hydrogen-bond acceptors but not hydrogen bond donors, and are overall electrically neutral (Ostuni, E. et al., "A Survey of Structure-Property Relationships of Surfaces that Resist the Adsorption of Protein", *Langmuir*, 17, 5605–5620, (2001)). In this approach, the non-specific binding resistant layer is generally formed on the substrate and then is chemically activated to allow attachment of the capture probe. For example, the method described by Huang in copending U.S. Pat. application Ser. No. 60/451,068, incorporated herein by reference, may be used to reduce nonspecific adsorption to the microparticles of the present invention. In the method described in that disclosure, a thin film of polyethylene glycol alkyl acrylate is grown on the surface of the solid substrate, i.e., the microparticles, using surface initiated atom transfer radical polymerization. This method is described in detail in Example 7 below. In summary, the microparticles are first treated with an initiator molecule to form an initiator-coated microparticle, which is then contacted with at least one polyethylene glycol alkyl acrylate monomer in solution in the presence of a catalyst. The resulting polyethylene glycol alkyl acrylate coating may be further activated and conjugated to the capture probe using various methods known in the art, including, but not limited to the use of trichloro-s-triazine (Abuchowski, A. et al., *J. Bio. Chem.* 252, 3578–3581, and 3582–3586 (1977)), N,N'-carbonyldiimidazole (Bartling, G. J. et al. *Nature* (London), 243, 342–344 (1973)), and organic sulfonyl chloride such as tosyl chloride and tresyl chloride (Nilsson, K. and Mosbach, K. *Methods in Enzymology*, 1984, 104, pp 56–69).

As described previously for protein libraries, the diversity of a nucleic acid or organic molecule library can vary considerably according to the specific application of the end user. In a preferred embodiment, each particle in the library carries a different capture probe, a class of capture probes, or a defined mixture of capture probes. However, a library can be made redundant by having more than one particle in the library carry the same capture probe. This could at times be preferable, since the certainty of measuring the presence of a specific analyte would be statistically greater for moderately redundant libraries (3–5 copies of each probe). The needs for redundancy will vary according to the concentration of the target analyte, the amount of sample available, and other factors.

A commercially useful library may thus consist of pre-manufactured microparticles with known capture probes already attached, or alternatively the microparticles may be treated with a specific surface chemistry to enable the user to custom-synthesize a library of particular interest. The probe may be produced separately and then attached in a separate step using linker chemistry, crosslinker chemistries or other techniques known in the art. Examples of linking groups include, but are not limited to hydroxyl groups, amino groups, carboxyl groups, aldehydes, amides, and sulfur-containing groups such as sulfonates and sulfates. Examples of the crosslinking chemistries include, but are not limited to hydroxy reactive groups include s-triazines and bis-epoxides, sulfhydryl reactive groups including maleimides and haloacetyl derivatives, amine reactive groups such as isothiocyanates, succinimidyl esters and sulfonyl halides and carboxyl reactive groups such as carbodiimides.

In another approach, the capture probe may be directly synthesized on the surface of the particles of the present invention. Probes that may be directly synthesized on the particles include, but are not limited to nucleic acids (DNA or RNA), peptide nucleic acids, polypeptides and molecular hybrids thereof. In the direct synthesis approach, a particle that is derivatized with a reactive residue to be used to chemically or biochemically synthesize the probe directly on the particle is used. The chemical linkage of the reactive residue must not be cleavable from the microparticle during post-synthesis deprotection and cleanup of the final probe-coupled microparticles (Lohrmann et al., *DNA* 3, 1222 (1984); Kadonaga, J. T., *Methods of Enzymology* 208, 10–23 (1991); Larson et al., *Nucleic Acid Research* 120, 3525 (1992); Andreadis et al. *Nucleic Acid Res.* 228, e5 (2000); and Chrisey et al. WO/0146471). This approach allows for mass production and assembly of libraries.

In summary, the means for manufacturing a library will depend on the assay to be performed, the type of library, the diversity of the library, the redundancy, the type of linker chemistry, and other factors. A general requirement for a useful particle library is the correlation between the identities of the particles and the identities of the capture probes. This correlation should be preserved regardless of how the library is synthesized, whether by combinatorial methods, directed automated synthesis, manual synthesis, or other methods; and regardless of how and when the correlation is determined.

In general, each microparticle in the library carries multiple copies of a specific capture probe or a defined mixture of capture probes. The optimal surface density of the capture probes may vary according to the application and reaction conditions. For example, the kinetics of DNA hybridization to immobilized DNA probes has been investigated (Chan, et al., "The biophysics of DNA hybridization with immobilized oligonucleotide probes", *Biophysical Journal* 69, 2243–2255 (1995); Livshits, M. A., Theoretical analysis of the kinetics of DNA hybridization with gel-immobilized oligonucleotides, *Biophysical Journal* 71, 2795–2801 (1996)). Similar studies have been carried out for protein-protein interactions (Stenberg, M. and Nygren, H., "Kinetics of antigen-antibody reactions at solid-liquid interfaces", *Journal of Immunological Methods* 113, 3 (1998). In general, there is poor mixing at the interface of a 2-dimensional surface array and the solution containing the target analytes. For efficient specific binding to take place on a 2-dimensional fixed arrays, generally some nonspecific binding must first take place on the surface, followed by 2-dimensional diffusion along the surface, which then leads to hybridization or binding. The need for 2-dimensional diffusion limits the probe surface density, the rate of binding, and hence the total signal that can be generated in a given time. In contrast, in particle-based assays carried out in a well-mixed environment (for example, a free suspension or in a flow field provided by a microfluidic device), the boundary layer at the interface is continuously replenished and higher probe surface densities are more favorable. This results in higher rates of binding, potentially larger binding signals, higher probe density, increased sensitivity, improved specificity, and reduction of nonspecific binding interferences. In the present invention, higher probe density on the microparticle surface can thus help reduce nonspecific binding without adversely affecting specific binding. A further advantage of particle-based assays, and particularly the system of the present invention, is that the amount of sample required for the assay can in principle be reduced. In fixed array systems, analyte has to be in substantial excess to the probe in order to drive the reaction kinetics and overcome long diffusion lengths. Only a fraction of the analyte molecules will typically be able to interact with its complementary probe in a fixed array. Due to the shorter diffusion length in a well-mixed system, all of the analyte is equally available to all of the probe binding sites. This would increase sensitivity and decrease reaction times and assay turnaround time.

In a preferred embodiment of the present invention, the microparticle library is provided as a multiplicity of identifiable microparticles with no additional surface chemistry or capture probes. Such a library may be used for many purposes, including but not limited to labeling substrates for combinatorial synthesis, and being used as starting materials for custom made screening libraries.

In another preferred embodiment, the microparticle library is provided with derivatized particle surfaces suitable for specific linker chemistry, direct synthesis, or other means for attaching capture probes. The end user may then custom tailor the library with probes according to their specific assay needs.

In still another preferred embodiment, the microparticle library is populated with particles carrying known capture probes that are correlated with a list of particle identities. The end user may then use the entire library as provided, or sort the library into subsets according to their specific assay needs.

In still another preferred embodiment, the microparticle library is populated with particles carrying unknown capture probes, for example created by combinatorial methods. The end user may then screen the library for "hits" against specific targets by resonant light scattering techniques, and characterize the corresponding probes using techniques known in the art.

Assays

Chemical or biological assays carried out with the present invention may make use of the specific interaction of binding pairs, one member of the pair located on the surface of the microparticle (also referred to as the "probe", "binding partner", "receptor", or grammatically similar terms) and the other member of the pair located in the sample (referred to as the "target", "analyte", or grammatically similar terms). Generally the analyte carries at least one so-called "determinant" or "epitopic" site, which is unique to the analyte and has enhanced binding affinity for a complementary probe site.

The nature of assay types possible with this invention varies considerably. Probe/target binding pairs may, for example, be selected from any of the following combinations, in which either member of the pair may be the probe and the other the analyte: antigen and specific antibody; antigen and specific antibody fragment; folic acid and folate binding protein; vitamin B12 and intrinsic factor; Protein A and antibody; Protein G and antibody; polynucleotide and complementary polynucleotide; peptide nucleic acid and complementary polynucleotide; hormone and hormone receptor; polynucleotide and polynucleotide binding protein; hapten and anti-hapten; lectin and specific carbohydrate; enzyme and enzyme enzyme/substrate, enzyme/inhibitor, or; biotin and avidin or streptavidin; and hybrids thereof, and others as known in the art. Binding pairs may also include members that form covalent bonds, such as, sulfhydryl reactive groups including maleimides and haloacetyl derivatives, and amine reactive groups such as isothiocyanates, succinimidyl esters, sulfonyl halides and carbodiimide reactive groups such as carboxyl and amino groups.

Specific examples of binding assays include those for naturally occurring targets, for example antibodies, antigens, enzymes, immunoglobulin (Fab) fragments, lectins, various proteins found on the surface of cells, haptens, whole cells, cellular fragments, organelles, bacteriophage, phage proteins, viral proteins, viral particles and the like. These may include allergens, pollutants, naturally occurring hormones, growth factors, naturally occurring drugs, synthetic drugs, oligonucleotides, amino acids, oligopeptides, chemical intermediates, and the like. Practical applications for such assays include for example monitoring health status, detection of drugs of abuse, pregnancy and pre-natal testing, donor matching for transplantation, therapeutic dosage monitoring, detection of disease, e.g. cancer antigens, pathogens, sensors for biodefense, medical and non-medical diagnostic tests, and similar applications known in the art.

Proteins are of interest in many diagnostic tests, such as blood typing, detecting cell populations, screening for pathogens, screening for immune responses to pathogens, immune complexes, lectins, mono- and polysaccharides, the presence of allergens and haptens in samples such as physiological fluids, air, process streams, water, and the like. Likewise, using nucleic acids or polynucleotides as probes may find many applications in the detection of complementary strands in a sample, detection of mRNA for gene expression, genomic and proteomic microarray applications, detection of PCR products, DNA sequencing, clinical diagnostics, medical screening, polymorphism screening, forensic screening, detection of proteins specifically binding to nucleic acids, and others as known in the art.

Figure 1:
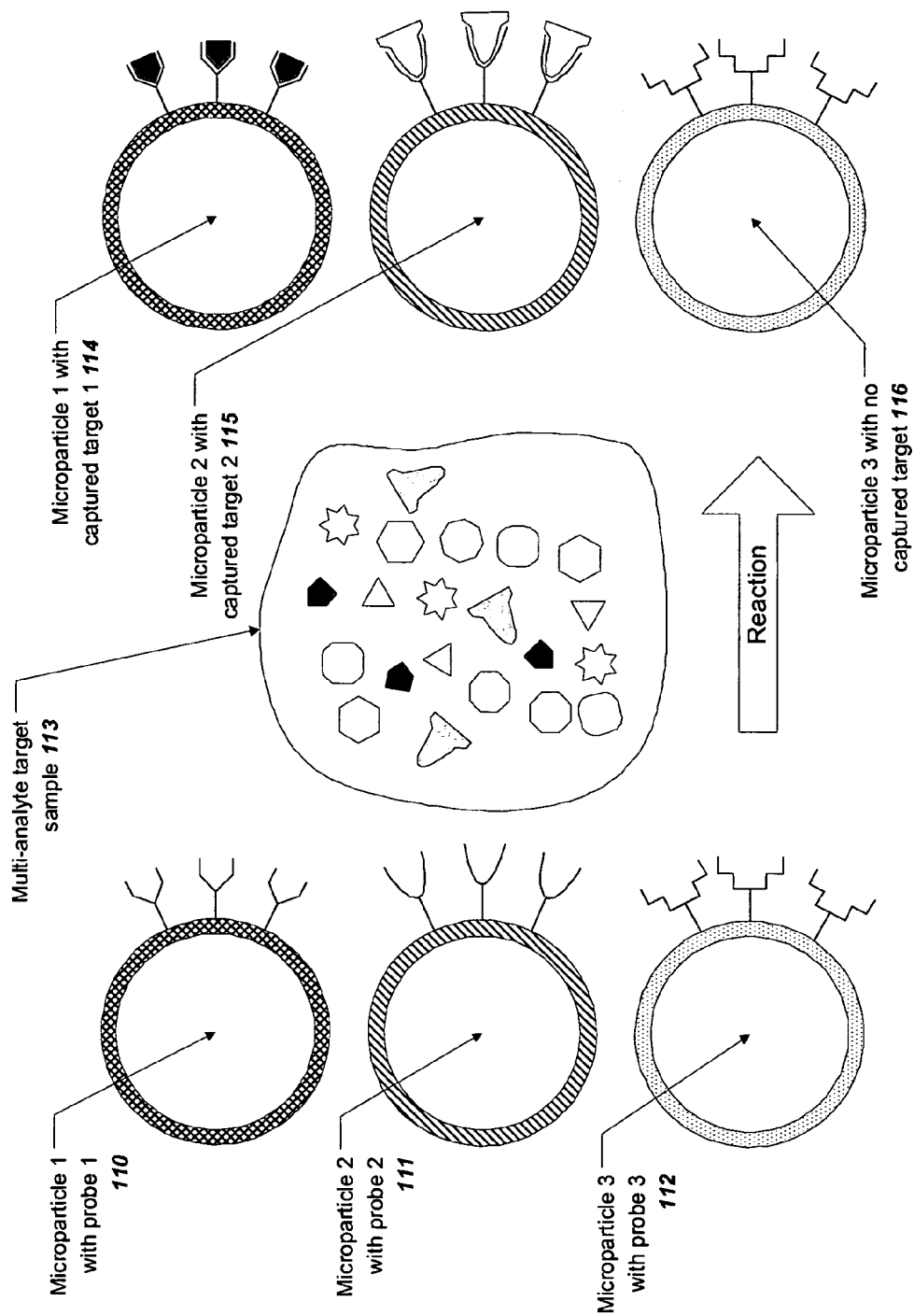

Assays can be done using various specific protocols. A schematic diagram of a typical protocol is shown in FIG. 1. For detection or quantitation of an analyte, a sample 113 is typically combined with a solution containing the microparticles 110, 111, etc. Various additional steps may be carried out, such as incubations, washings, the addition of miscellaneous reagents, etc. as required by the specific assay. If an analyte of interest is present and one or more microparticles exists with a complementary capture probe, that analyte will bind to those microparticles as illustrated by microparticles 114 and 115. Conversely, according to FIG. 1, if an analyte complementary to a specific microparticle is not present, there will be no binding on that particle, for example microparticle 116.

In one embodiment of the present invention, resonant light scattering is used only for particle identification in the assay, as described in the section "Particle identifications methods and systems", infra. Detection is done using conventional detection methods including, but not limited to fluorescence, chemiluminescence, nanoparticle tags, and other techniques known in the art. In this embodiment, a label may be attached to a member of the binding pair to enable detection. Alternatively, a sandwich assay may be used in which the target analyte is captured by the probe attached to the microparticle. Then a second binding partner, which has an attached label, is used to bind to the captured analyte.

In another embodiment, resonant scattering is used only for detection of binding, as described in the section "Particle-based binding measurement, infra. In this embodiment, particle identification is done by other means such as having the particles remain in a fixed position or by the use of fluorescent dyes, as described by Chandler et al., in U.S. Pat. No. 5,981,180, or nanoparticle labels, as described by Chandler et al., in U.S. Pat. No. 6,268,222, attached to the microparticles. Moreover, no particle identification is required if only one type of probe microparticle is used in the assay.

In a preferred embodiment, both particle identification and detection of binding are done using resonant scattering. The detection and identification of bound analyte is described in detail in section "Particle identifications methods and systems" and in section "Particle-based binding measurement" of this disclosure. As explained more fully there, whereas in current practice it is necessary to separate unbound components of the sample from the microparticles, due to potential interference from unbound reporter groups, in the present invention this step is optional.

Assays using particles of the invention can be carried out in a large variety of sample matrices including separated or unfiltered biological fluids such as urine, peritoneal fluid, cerebrospinal fluid, synovial fluid, cell extracts, gastric fluid, stool, blood, serum, plasma, lymph fluid, interstitial fluid, amniotic fluid, tissue homogenate, fluid from ulcers, blisters, and abscesses, saliva, tears, mucus, sweat, milk, semen, vaginal secretions, and extracts of tissues including biopsies of normal, malignant, and suspect tissues, and others known in the art. The sample can also be obtained from an environmental source such as soil, water, or air; or from an industrial source such as taken from a waste stream, a production line, reactors, fermentation apparatus, cell culture medium, or from consumer products, foodstuffs, and others. The test sample can be pre-treated prior to use depending on the details of the assay, techniques for which would be well known by those in the art.

Particle Identification Methods and Systems

According to the present invention, high-resolution features in the resonant light scattering spectrum are useful for providing unique identification patterns for each member of a population of microparticles. The scattered light spectrum carries information content in the form of resonances of specific widths and shapes at specific wavelengths. As is known in the art, the location, width, and relative intensities of the resonance features all vary with particle size and refractive index of the particle. Generally, resonance features can be seen over a reasonably wide range of particle sizes and refractive indices. The resonances useful for this invention, however, are typically formed within specific ranges of these particle properties. Furthermore, the it is contemplated that the addition of layers and/or zones of varying refractive index to a core particle could, within specific parameters of size and refractive index, create additional richness to the resonant light scattering pattern. Additionally it will be readily apparent that in any microparticle production process, there would be natural variations, or, if needed, induced variations, in the key parameters defining the resonant light scattering pattern, namely particle dimensions and refractive indices. This variability in turn enables one to create large populations of microparticles, each of which giving rise to a distinct resonant light scattering pattern that can be used as an identifier for the particle.

Figure 2:
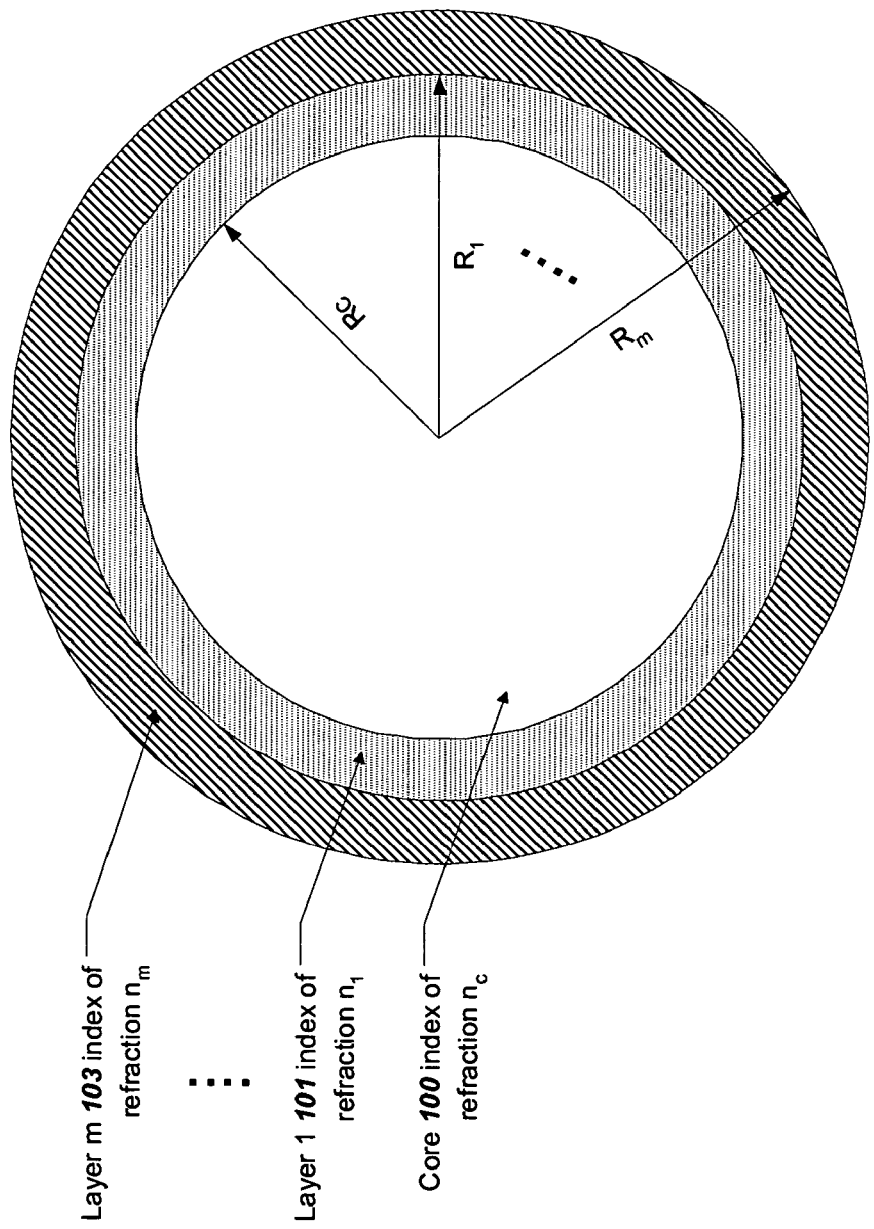

A general microparticle according to the present invention is shown in FIG. 2, which depicts a uniform core 100 of radius r and index of refraction $n_c$. FIG. 2 also depicts an optional number m of layers 101 . . . 103 with outer radii $r_1 \ldots r_m$ and indices of refraction $n_1 \ldots n_m$. The number of layers m may be zero, and if greater than zero, will typically be less than about 5. In this context, the term "layer" or "layers" may include regions containing sharp refractive index boundaries, or zones of variable refractive index without sharp boundaries. In either case, variability of refractive index and layer dimension may provide richness to the resonant light scattering spectrum, which can be used to advantage in particle identification.

Figure 3:
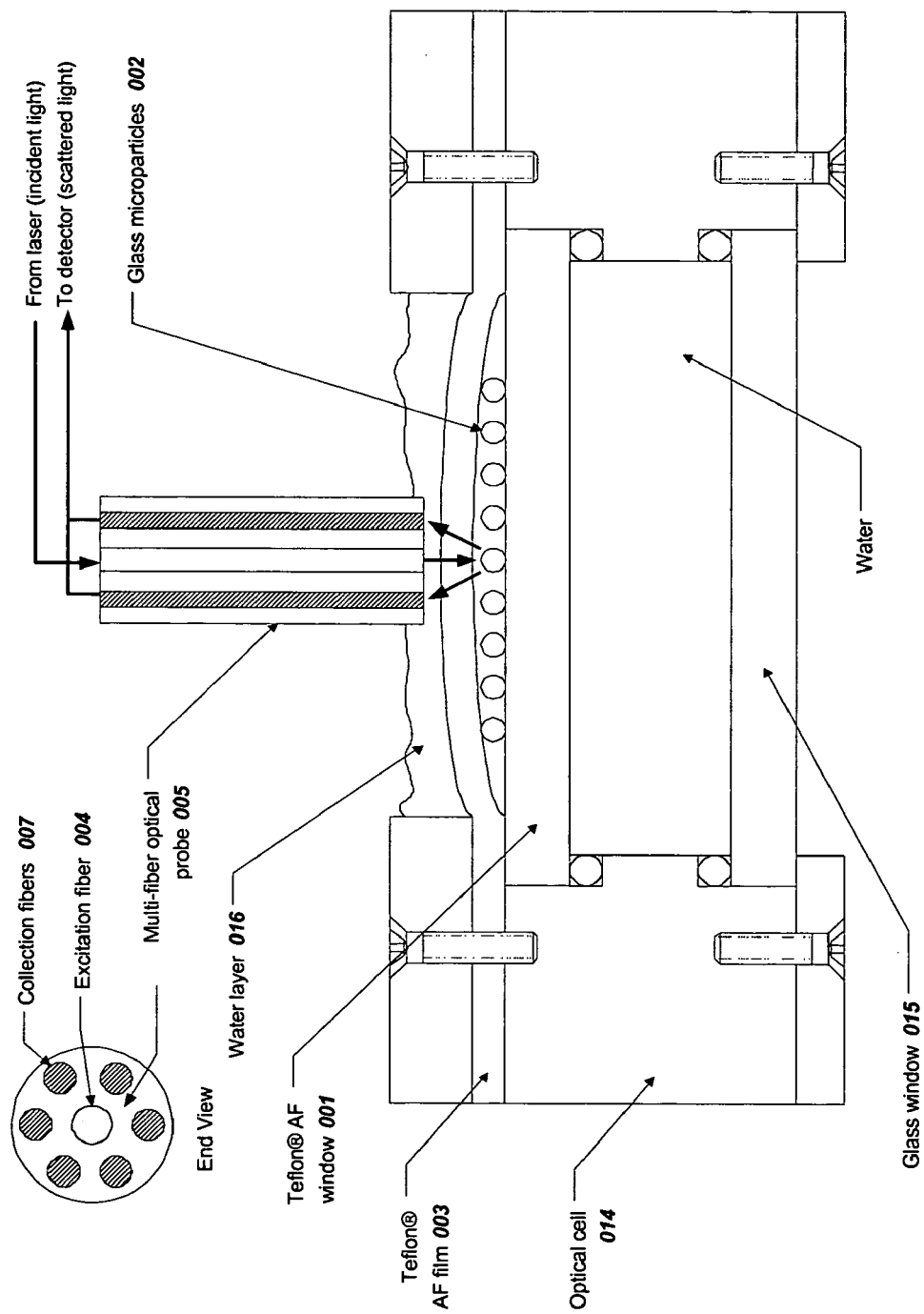
FIG. 3 is a schematic diagram of an optical cell for holding microparticles and an optical probe for illuminating the microparticles and measuring the scattered light intensity.
Figure 4:
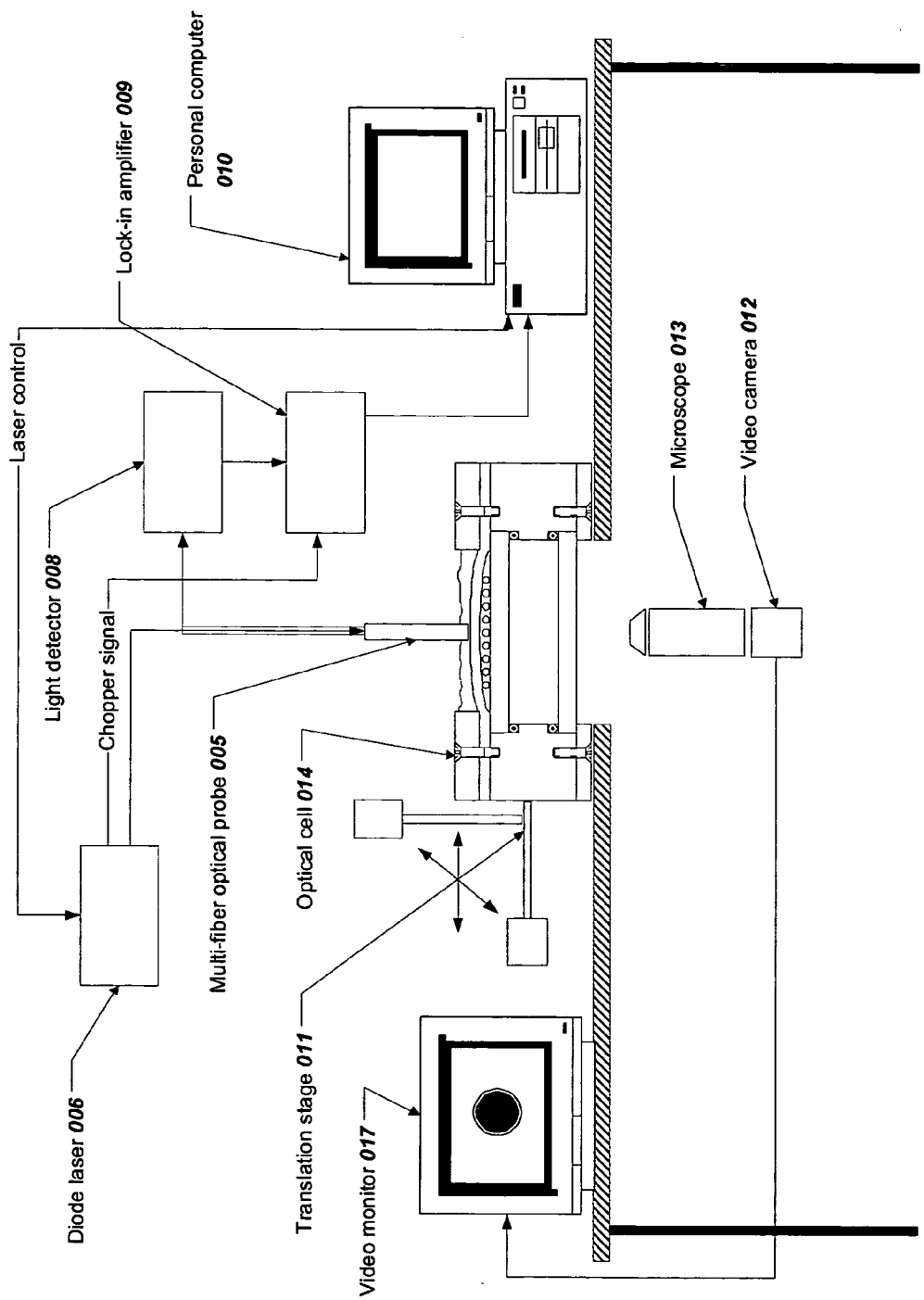
FIG. 4 is a schematic diagram of the optical probe detection system used to measure scattered light from microparticles. The components are not drawn to scale.

When irradiated with light of wavelength $\lambda$, the particle will scatter a portion of that light to a detector with an intensity $I(\lambda)$. As the incident wavelength is scanned, i.e., varied over the analytical wavelength range, a "scattering pattern" or "scattering spectrum" as a function of wavelength results. In order to measure the resonant light scattering spectra from particles according to this invention, a suitable detection cell is required in which the particles are placed during the measurement. FIG. 3 illustrates one embodiment of an optical cell 014 useful for measuring high-resolution resonant light scattering spectra from a microparticle. FIG. 4 depicts one embodiment of the associated experimental apparatus, including the optical cell 014, light detector 008, and associated supporting equipment used to measure the high-resolution resonant light scattering spectrum from a microparticle. Details of such a measurement are given in Example 1 and are summarized here.

The microparticle of Example 1 is about 40 micrometers in diameter and has an index of refraction about 1.9 at a wavelength of about 775 nanometers. As is known in the art, light scattered at the resonant wavelengths emanates from the interior of the particle and must thus be transmitted through the outer optical region of the particle prior to being scattered. Therefore, the outer optical region of the particle (that part of the core outside the caustic surface) must be substantially transparent at the wavelengths of interest. In The following discussion, reference is made to FIGS. 3 and 4. The microparticle is held in aqueous suspension in an optical cell 014 constructed of Delrin® and Teflon® AF 2400. Teflon® AF 2400 is a preferred material because it has refractive index closely matching that of water, thus reducing the optical background and associated noise due to reflection and refraction at the interfaces between water and the cell windows. Teflon® AF 1600 has an index of refraction even closer to water than Teflon® AF 2400, and is another preferred material. Another preferred material is fluoroacrylate, commonly used in photoresist materials, which has a refractive index of about 1.38 at the wavelengths of interest. One practiced in the art would recognize that other optical cell configurations would be possible, provided the design and materials are such that incident light efficiently illuminates the particle or particles, scattered light is minimized, and the cell dimensions are compatible with the intended applications of the invention.

A multi-fiber optical probe 005 comprising one central excitation fiber 004 and surrounded by 6 detection fibers 007 in a hexagonal pattern is located above the particle, its end extending into the water layer. The excitation fiber is connected to the output of a scanning diode laser 006. One practiced in the art would recognize that alternative incident light sources could be used, such as tunable dye lasers, and polychromatic sources such as gas discharge lamps, light-emitting diodes, and incandescent lamps. A polychromatic light source, in order to produce incident light of more selective wavelength, will generally require coupling to one or more wavelength-selecting means such as non-dispersive elements (e.g. fixed wavelength passband filters, tunable wavelength passband filters, holographic filters) or dispersive elements (e.g. monochromators, prisms, gratings) in order to achieve the required spectral resolution.

The light may be coupled into the optical system by different light coupling means, including lenses, mirrors, prisms, fiber optic devices, beam expanders, and others well known in the art.

The detection of scattered light may be done in different ways. As shown in the Examples, a preferred embodiment for detection of scattered light from microparticles is by scanning the incident wavelength and detecting the light with detectors or imaging devices that are not wavelength-selective, i.e. are not suitable for distinguishing light of different wavelengths. One skilled in the art would recognize that it is also, in principle, possible to illuminate the particles with polychromatic light and detect the scattered light with a wavelength-selective detection means such as non-dispersive elements (e.g. fixed wavelength passband filters, tunable wavelength passband filters, holographic filters, wavelength-selective imaging devices such as color digital cameras) or dispersive elements (e.g. monochromators, prisms, gratings).

As the laser is scanned in wavelength, part of the light interacts with the particle and is scattered. Light that does not interact with the particle escapes through a window 015 below the cell. Some light is scattered from the particles in all directions; however, one preferred direction is near 180 degrees from the incident beam, otherwise referred to as "back-scattered" light. The back-scattered light is received by the six detection fibers 007, combined, and sent to a suitable light detection means, for example a silicon photodetector, photomultiplier, or the like. A chopper, in this example located inside the diode laser 006, modulates the incident light. The electrical signal from the detector output is in turn sent to a lock-in amplifier 009 along with the modulation signal. The output of the lock-in amplifier and a "ramp" signal proportional to the incident wavelength are then routed to a data capture board installed in a personal computer 010. Software controls the laser scan and the acquisition and display of the scattered light spectrum. It should be noted that since resonance peak positions are not dependent on detection angle, the use of peak positions to define scattering patterns is equally valid for other detection geometries.

For illustrating the present invention, it is useful to characterize the spectrum of a given particle by the locations and widths of the resonance features in the spectrum. These features comprise a spectral pattern, which may be analyzed and characterized. The spectrum may be analyzed in a number of ways including peak finding, deconvolution, peak fitting, pattern recognition, and others known in the art, and these methods may be automated and computerized.

Figure 5:
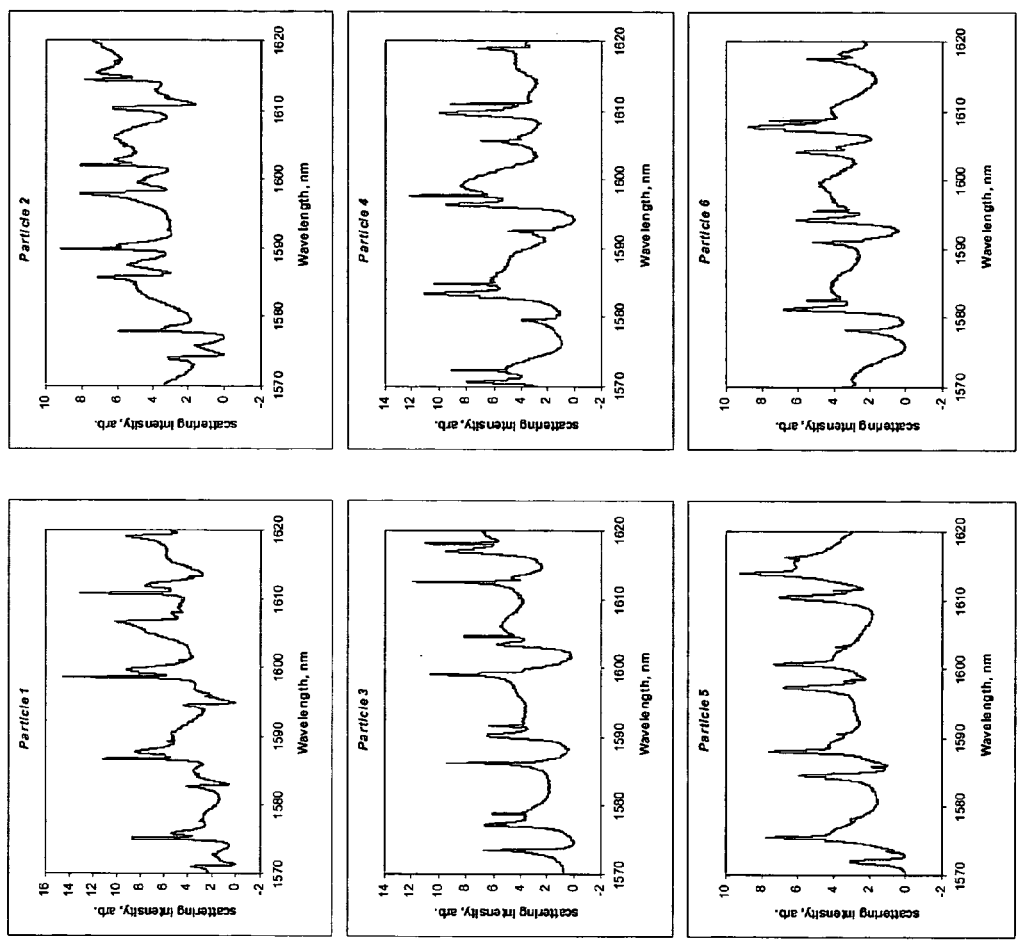
FIG. 5 is a set of scattered light spectra from different microparticles from which unique particle identities can be established according to the invention.

To illustrate the principle behind identifying particles according to the invention, it is useful to consider the scattering spectrum of a group of similar particles from a single lot of microparticles, as for example in FIG. 5. As stated previously, within each lot there will be natural variations in size and refractive index, which can be used profitably to give rise to unique scattered light spectra according to the invention. It can be readily seen that among the six particles from the same lot (chosen at random), uniquely distinct scattered light spectra are obtained, and the ability to identify the particles based on these spectra is readily apparent. It will be apparent to those skilled in the art that automated spectral analysis techniques (e.g., spectral coding, pattern recognition, filtering, and the like) could be applied to scattered light spectra in order to extract spectral features including, but not limited to peak location, peak width, peak order, periods between peaks of different orders, and polarization-dependent spectral properties that are useful for creating a unique identifying "tag" or "key" for each particle in a population of particles.

It should be noted that there is opportunity to add further richness and therefore multiplicity of combinations to the scattered light spectrum through purposeful modifications of the untreated commercial microparticles. For example, additional layers 101 . . . 103 could be employed, each layer having the potential for adding or modifying scattering resonance features, thereby creating additional combinations of identifying codes. Likewise, variations, whether naturally occurring or purposely induced, in refractive index, thickness, or both will give rise to useful variations in the scattering spectrum. It should be noted that by these variations, entirely different spectral patterns are produced, rather than shifting of spectral patterns as is the case with variations in diameter only. The concept of adding layers for the purpose of adding richness to the resonant light scattering spectrum is illustrated in Examples 14–19.

To be useful in identifying microparticles according to this invention, the dimensions and refractive indices of the core and layers must fall within limits imposed by the fundamental Mie theory of light scattering. Simply put, although particles of virtually any size and refractive index will interact with light to some degree, for a given range of wavelengths only specific combinations of these parameters will give rise to spectra useful for identification according to the present invention. In addition, since most assays of interest will be done in aqueous media, the wavelengths chosen for analysis must be such that there is minimal interference from optical absorption by water. Furthermore, the wavelengths chosen should be obtainable by available light sources such as arc lamps, lasers, or diode lasers.

The inventors, through use of computer models and subsequent laboratory measurements, have determined useful ranges for several of the critical parameters. In what follows, distinction is made between (1) layers that give rise to additional optical resonance features or changed features, i.e. positionally changed in their wavelength locations relative to one another (so-called "optically active" layers), and (2) layers that serve only to preserve the integrity of the core or serve as chemically or biologically suitable substrates for the attachment of capture probes or suppression of non-specific binding ("chemically active" or "biologically active" layers). It is also possible that a layer could serve both functions, in which case it would be "optically active" as well as being a suitable chemical or biological substrate. A typical, but non-limiting example of an optically active layer is one in which the layer has thickness of between about 50 and 20,000 nanometers (20 micrometers).

Accordingly, one preferred embodiment of an identifiable microparticle comprises a substantially spherical, transparent glass core of diameter about 100 micrometers or less, preferably about 75 micrometers or less, and more preferably about 50 micrometers or less, and of refractive index between about 1.45 and about 2.1, preferably between about 1.6 and 2.1, at wavelengths between about 600 and 1650 nanometers.

Another preferred embodiment of an identifiable microparticle comprises (1) a substantially spherical, substantially transparent glass core of diameter about 100 micrometers or less, preferably about 75 micrometers or less, and more preferably about 50 micrometers or less, and of refractive index between about 1.45 and about 2.1, preferably between about 1.6 and 2.1 at wavelengths between about 600 and 1650 nanometers; and (2) one substantially transparent, optically active layer, capable of supporting additional resonance light scattering features or changing existing features.

Still another preferred embodiment of an identifiable microparticle comprises (1) a substantially spherical, substantially transparent glass core of diameter about 100 micrometers or less, preferably about 75 micrometers or less, and more preferably about 50 micrometers or less, and of refractive index between about 1.45 and about 2.1, preferably between about 1.6 and 2.1 at wavelengths between about 600 and 1650 nanometers; and (2) one substantially transparent, optically active layer, capable of either or both supporting additional resonance light scattering features or changing existing features, and (3) one or more chemically or biologically active, substantially transparent, layers of thickness between about 1 nanometer to 10 micrometers useful for procedures described in the previous section "Capture probes and particle libraries".

Still another preferred embodiment of the identifiable microparticle comprises (1) a substantially spherical, substantially transparent glass core of diameter about 100 micrometers or less, preferably about 75 micrometers or less, and more preferably about 50 micrometers or less, and of refractive index between about 1.45 and about 2.1, preferably between about 1.6 and 2.1 at wavelengths between about 600 and 1650 nanometers; and (2) two or more substantially transparent, optically active layers, each capable of either or both supporting additional resonance light scattering features or changing existing features, and (3) one or more chemically or biologically active, substantially transparent layers of thickness between about 1 nanometer to 10 micrometers useful for procedures described in the previous section "Capture probes and particle libraries".

Another preferred embodiment of the present invention is a multiplicity or population of identifiable microparticles, such a population being useful for a number of applications including biological or chemical assays and the like. The type of microparticle (i.e. the number and composition of the core and layers) chosen for a specific application will depend on the nature of the sample and the number of analytes to be screened or detected. In many applications, for example high-throughput screening for drug candidates or screening for disease biomarkers, the utility of a population of identifiable microparticles according to the present invention will be directly related to the number of unique microparticles in the population, higher numbers generally being preferred. The number of possible combinations of scattering patterns that can be used for identifying a population of microparticles in the above embodiments can be very large (greater than about $10^6$ should be readily attainable) as the core radii, the layer thicknesses, and their respective refractive indices are allowed to vary within a population, thus producing a very rich set of scattering patterns for use as particle identifiers. In other applications, for example biomarker screening or specific disease diagnostics, a smaller number of unique microparticles may suffice.

The detection system and method described above and depicted in FIGS. 2 and 3 is suitable for measuring the high-resolution scattered light spectrum of one particle at a time. This apparatus, while effective for demonstrating the principles of the invention, requires the alignment of a single particle with the optical probe and is generally manual and somewhat time-consuming.

An improvement to the single-particle detection means would be to form a linear or rectangular array of particles by constraining them, for example in tubes or in a series of channels, indentations, or grooves on a substrate. The particles could then be scanned in a known order by rapidly moving the laser beam from particle to particle or by moving the substrate holding the particles. In this case, identity of the particles and their probes is first established by their spectral scattering patterns (or by any other means), and then the particles are loaded into the tubes, grooves, indentations, or channels in a known order. In the Examples, the particle handling is accomplished by manual pipetting operations. One skilled in the art would recognize that other particle handling means would be suitable, including the use of automated or semi-automated microfluidics devices, and combinations of fluid control devices such as pumps, syringes, control valves, and the like. After the particles are placed in position, the identities of the particles are thereafter maintained by their relative locations within the channels, and optionally confirmed by their scattering patterns. Similarly, in a two-dimensional but otherwise unstructured arrangement of microparticles in which they remain stationary during the assay, the identities of the particles are maintained by their relative positions.

Figure 6:
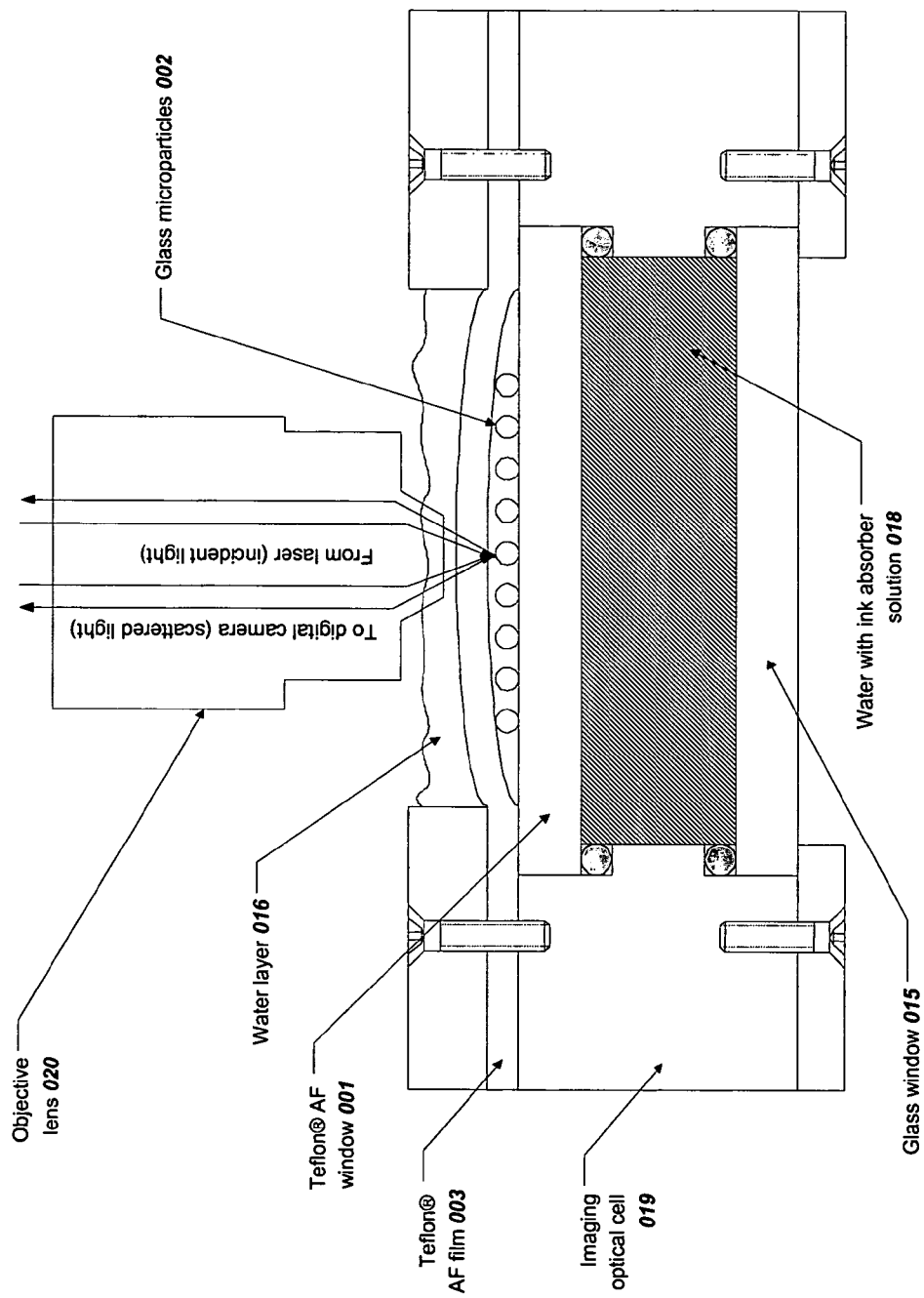
FIG. 6 is a schematic diagram of an optical cell for holding microparticles and a microscope lens for simultaneously imaging the particles and measuring the scattered light intensity.

A still more efficient detection means is based on resonant light scattering imaging. In this method, resonant light scattering spectra are detected simultaneously from a field of multiple particles by imaging means, such as a camera. The camera images the particles repeatedly as the incident wavelength is scanned, typically acquiring one image for each wavelength step in the scan. Each image contains scattering intensity information from every particle in the image, at a specific wavelength. By suitably processing the entire set of images thus obtained, the scattered light spectrum from each particle may be derived. The camera could be any imaging device capable of the speed and sensitivity required for this application. The camera is preferably a digital camera, more preferably based on a two-dimensional CCD (charge coupled device) or equivalent imaging means. Preferably, the camera functions and data acquisition are controlled by a computer operably linked to the camera and to the scanning light source, said computer having software suitable for these purposes. Additionally, the computer may contain data analysis means, i.e., software utilizing various methods including peak finding, deconvolution, peak fitting, pattern recognition, and others known in the art, for identifying the particle, detecting binding and identifying the analyte or groups of analytes. A typical experimental setup is schematically shown in FIGS. 6 and 7. FIG. 6 shows an imaging optical cell 019 useful for spectral imaging according to this invention; FIG. 7 shows the associated components needed to carry out the measurement. Details of the method and system are given in Example 2; a summary is given here. A population of microparticles is isolated in imaging optical cell 019 and imaged with microscope 021, using a scanning diode laser 022 as light source. The particles could be randomly distributed, or distributed in an ordered fashion such as in a tube or in a linear or rectangular array by constraining them in grooves, channels, or indentations on a substrate. The magnification is set to simultaneously image the particles of interest. Back-scattered light from particles in the field is collected and imaged by the objective lens 020 and associated optics on the plane of a digital camera 026. As the laser wavelength is scanned, a digital image is taken at each wavelength step and stored; thus a complete wavelength scan results in a series of digital images of all the particles, one image for each interval. The intensity of scattering from a particle a given wavelength is related to the brightness of that particle's scattering image at that wavelength. Thus, with suitable computerized image processing and spectral analysis, the complete scattering spectra of all particles can be extracted from the set of images obtained during the scan. An example of one typical image taken from such a set of images is shown in FIG. 8. It is seen that the light of interest (scattered light) 106 emanates from a ring or from a segmented ring of light along the particle's edge (see a discussion of this effect for example in Lynch, D. K. and Livingston, W., *Color and Light in Nature*, Cambridge University Press (2001). The incident and scattered light beams used in Example 2 were polarized independently, with the two axes of polarization parallel to each other. This results in sectors of scattered light centered approximately at the 12:00, 3:00, 6:00, and 9:00 positions of the circle as indicated for the center image of FIG. 8 by the numbers 12, 3, 6, and 9 respectively. Theory predicts, and results confirm, that scattered light spectra from the "12" and "6" regions are equivalent and scattered light spectra from the "3" and "9" regions are equivalent. Furthermore, spectra from the two pairs of sectors are different from one another. This results in the ability to identify a particle by a combination of two substantially independent spectra, rather than a single spectrum, increasing the multiplicity of identifiable particles and also the accuracy of identification.

Light from this ring is measured by image processing techniques, for example from measuring the image intensity from a subset of pixels 101, and repeated for each image 102 . . . 105 in the wavelength series (See FIG. 9). The subset of pixels could be selected by a variety of means including average intensity threshold, signal/noise or other spectral property threshold, geometrical features, radial or azimuthal position relative to the center, digital filtering, and the like. The image intensity could be calculated by a variety of means including pixel-averaging, taking the maximum value from a subset of pixels, weighted averaging according to statistical criteria such as signal/noise ratio, etc. as would be known in the art. An example of such scattered light spectra 150 for one of the particles, obtained by applying specific selection rules as explained in Example 2, is shown in FIG. 9. By extension of this Example, it would be possible to measure scattering spectra from a large population of microparticles rapidly and efficiently. This would be especially advantageous over methods reported in the literature in biological or chemical assays, for applications including drug discovery, high-throughput biomedical screening, genomic mapping, and the like.

In order to carry out useful detection of analytes, a suitable means for effectively contacting the particles with reagents and analytes is required. Preferably, the particles may be contacted with reagents and analytes in any order and any number of times throughout an experiment. Thus, the detection cell requires at least one port, preferably two or more ports, enabling the flow of reagents and analytes into the cell, and suitable flow control elements enabling the selection of reagents or analytes and the flow speed. In the Examples of this application, the particles are introduced into the detection cell with a manually operated pipette, and the reagents and analytes are delivered to the detection cell through two ports ("inlet" and "outlet") by peristaltic pumps or syringe pumps connected to the cell with flexible tubing. The pumps and any associated flow control valves, check valves, flow metering devices, and the like may be manually operated or automatically operated by computer control. Those skilled in the art would recognize that many possible arrangements of ports, pumps, tubing, and flow control elements could be employed, provided that the resulting system enables contacting the particles with reagents and analytes in a suitable manner.

Accordingly, a preferred embodiment of the system for identifying microparticles according to the present invention comprises an imaging system containing (1) a scanning diode laser light source; (2) an optical cell suitable for spectroscopic scattered light imaging and stray light rejection; (3) a means for contacting the microparticles with analytes and reagents; (4) a microscope with optical components suitable for imaging the field containing the population of particles of interest; (5) digital camera and monitor; (6) digital image acquisition hardware; (7) a computer operably linked to the components as needed and (8) software suitable for controlling the components, capturing data, and processing the data.

A preferred embodiment of a method for identifying microparticles further comprises (1) placing the population of microparticles in the field of view and focusing the microscope on the particles; (2) initializing the data capture software; (3) scanning the diode laser from a starting wavelength to an ending wavelength while simultaneously (4) capturing a digital image representative of the scattered light from all particles in the field of view for each wavelength step in the scan; (5) processing the digital images so as to produce scattered light spectra for each particle; and (6) applying spectral processing techniques to create a unique identifying marker or code for each particle.

Methods for Identification of Analytes

The identity of an analyte may be determined based upon the detection of binding to a capture probe whose identity is known. The absence of an analyte in a sample may also be determined using the same methods. Various methods are possible for the identification of analytes based upon the measurement of resonant light scattering.

In one preferred embodiment, one or more known capture probes are applied to the particles and then the particles are scanned over a first analytical wavelength range to produce a first reference resonant light scattering signature which is used to identify each particle and to correlate the identity of the capture probe to the identified particle. A number of first reference resonant light scattering signatures may be produced for the particles by repeating the scan at different times. For example, one first reference resonant light scattering signature may be obtained at the time of manufacture of the probe-coupled microparticles and then a second first reference resonant light scattering signature may be obtained immediately before the particles are used in the assay. Any one of the first reference resonant light scattering signatures may be used for the identification of the microparticle and the attached probe. However, it is preferred to use the most recently obtained first reference resonant light scattering signature to serve as the reference signature to detect binding. Alternatively, the particles may be scanned over a first analytical wavelength range to produce an identifying resonant light scattering signature for each particle before applying the capture probe. Then one or more known probes are applied to the particles. The identity of the probe is correlated with the identifying resonant light scattering signature of the particles to which it has been applied. In either case, the particles are contacted with a sample suspected of containing at least one analyte and if the analyte is present, binding occurs between the capture probe and the analyte. The particles are scanned over a second analytical wavelength range to produce a second binding resonant light scattering signature. The second analytical wavelength range used to detect binding may be the same or different from the first analytical wavelength range used to identify the particle. For example, only a portion of the first analytical wavelength range, which corresponds to a particular peak or other spectral feature, may be used as the second analytical range to detect binding. A series of second binding resonant light scattering signatures may be produced by successively scanning the particles to follow the binding in real time. Detection of binding is done by comparing either any one of the second binding resonant light scattering signatures to any one of the first reference resonant light scattering signatures, preferably the one most recently obtained, or any one of the second binding resonant light scattering signatures with a previous second binding resonant light scattering signature in the series. If the analyte is not present in the sample, there will be no difference, within experimental error, between the two compared resonant signatures. The identity of each bound analyte may then be determined on the basis of the correlation to the particle identity, determined as described above, and at least one second binding resonant light scattering signature. If desired, the amount of bound analyte, which is directly related to the amount of analyte in the sample under the appropriate conditions, may be determined by comparing the differences between the two compared resonant light scattering signatures, specifically, the degree of shift of the scattering pattern observed upon binding. The amount of analyte in the sample may then be determined from a calibration curve prepared using known standards, as is well known in the art.

In another preferred embodiment, at least one capture probe is applied to the particles, which are then affixed in a defined spatial array, such as in tubes or in a series of channels, indentations, or grooves on a substrate, wherein each particle has a defined locus. In this case, the identity of the particle and the attached probe is determined by the affixed particle locus. Then, the particles are optionally scanned over the analytical wavelength range one or more times to produce at least one reference resonant light scattering signature, as described above. The particles are contacted with a sample suspected of containing at least one analyte and the particles are scanned one or more times over the analytical wavelength range to produce at least one second binding resonant light scattering signature for each particle. Binding is detected as described above. Each bound analyte is identified on the basis of the affixed particle locus. The amount of analyte present in the sample may be determined by comparing the differences between the two compared resonant light scattering signatures, as described above.

In another preferred embodiment, at least one capture probe is applied to the particles and the particles are scanned over the analytical wavelength range to produce at least one first reference resonant light scattering signature for each particle, as described above. The capture probes are correlated with each identified particle, as described above. The particles are then contacted with a sample suspected of containing at least one analyte, the analyte comprising a detectable label, such as fluorescent moieties, chemiluminescent moieties, particles, enzymes, radioactive tags, quantum dots, light emitting moieties, light absorbing moieties, and intercalating dyes. Each analyte is identified on the basis of the correlation described above and the detectable label of the analyte using methods known in the art.

Particle-based Binding or Dissociation Measurement

As previously disclosed, it is an object of this invention to provide improved particles, methods, and systems for detecting binding between probe and target in biological and chemical assays. In this respect, the improvements of the present invention over current methods relating to particle-based assays have as a basis the phenomenon that resonant scattering patterns are sensitive to changes in the index of refraction at or near the surface of the particle. As is known in the art (see for example Hightower, R. L. and Richardson, C. B., "Resonant Mie scattering from a layered sphere", *Appl. Optics* 27, 4850–4855 (1988) and the references therein), a change of refractive index at the surface of a microparticle changes the conditions (specifically the wavelengths) at which resonances occur, and potentially the shapes and intensities of the resonances, which are measurable phenomena. Binding of target analytes to the surface of a microparticle in aqueous suspension can be viewed as displacing water molecules with chemical species that have, in general, indices of refraction different from water. The bound molecule or structure will in general have index of refraction greater than that of water. Theoretical models developed by the inventors show that for a typical microparticle of about 40 micrometers in diameter, binding of a protein or nucleic acid layer shifts the entire scattered light pattern in wavelength relative to the reference or unbound state, and the amount of shift is proportional to the thickness of the bound layer up to thicknesses of about 50 nanometers. As noted above, thicker layers, i.e., up to about 10 micrometers, may be used, but layers with a thickness greater than about 50 nanometers will alter the original resonances and in some cases result in the production of additional light scattering resonances in addition to the shift. It should be noted that this phenomenon does not require the use of reporter groups, a substantial improvement over existing particle-based assay technology. It should also be noted that other changes near the particle surface that may occur during binding, for example conformational changes in the probe or target, could result in shifts due to relative movement of chemical or physical groups and thus changes in mass distribution near the surface. Since, as is known in the art, the scattered light spectrum is affected by the interaction of the evanescent light wave with the mass distribution near the surface, changes in the mass distribution potentially lead to changes the spectrum. The net mass distribution change relative to the evanescent light wave upon binding a target moiety could be either away from or towards the particle surface, depending on the specific nature of the probe, target, surface charge, ionic environment, and other factors. Resulting resonant light scattering spectral shifts may thus be either "positive" (toward longer wavelengths) or "negative" (toward shorter wavelengths) depending on the assay being performed.

In general, when determining binding of an analyte by resonant light scattering methods, two measurements are made, one before exposing the particles to the analyte to establish a baseline, and one after exposing the particles to the analyte, as described above. The determination of binding is done by comparing the two signatures and is thus typically a "differential" measurement. Specifically, to detect binding of an analyte to a capture probe, at least one capture probe is applied to the particles of the present invention. The particles are optionally scanned one or more times over the analytical wavelength range to produce at least one first reference resonant scattering signature for each particle, as described above. The particles are then contacted with a sample suspected of containing an analyte. The particles are then scanned one or more times to produce at least one second binding resonant light scattering signature for each particle. Detection of analyte binding is done by comparing either any one of the second binding resonant light scattering signatures to any one of the first reference resonant light scattering signatures, preferably the one most recently obtained, or any one of the second binding resonant light scattering signatures with a previous second binding resonant light scattering signature in the series. The amount of analyte in the sample may be determined as described above.

It is also possible to detect the dissociation of an analyte from the capture probe by similar differential measurement. To detect dissociation, the probe-coupled microparticles are contacted with at least one analyte to allow binding of the analyte to the probe, and then the particles are scanned one or more times over the analytical wavelength range to obtain at least one first reference resonant light scattering signature for each particle. Then, the analyte is dissociated from the capture probe of the particle using any means known in the art. The means used to dissociate the analyte from the probe will depend on the nature of the analyte and capture probe. For example, for nucleic acid or peptide nucleic acid binding pairs, dissociation may be effected by increasing the temperature to melt the duplex or by treatment with base. For antibody-antigen binding pairs, the analyte may be dissociated by treatment with acid or base or a chaotropic agent such as urea, guanidine hydrochloride or sodium thiocyanate. After dissociation, the particles are scanned one or more times over the analytical wavelength range to produce at least one second dissociation resonant light scattering signature for each particle. Dissociation is detected by comparing either any one of the second binding resonant light scattering signatures to any one of the first reference resonant light scattering signatures or anyone of the second binding resonant light scattering signatures with a previous second binding resonant light scattering signature in the series.

Ideally, any shifts that occur will be due to the binding or dissociation of target analyte molecules. Since the optical effects used in this invention may be sensitive to variations in the environment of the microparticles (e.g. temperature, ionic strength, refractive index of the medium, etc.), undesired variations in these parameters represent "noise" insofar as they can contribute to changes in the scattered light pattern. Accordingly, it will be useful in this invention to provide a means of referencing to compensate for such effects, leaving only the shifts due to actual binding of analyte remain as "signal". This could be accomplished, for example by using some particles as reference particles on which no probes are attached and which have been treated if necessary to minimize non-specific binding. Any shifts measured in these reference particles would be caused primarily by environmental changes and could be used to compensate shifts measured from the particles containing capture probes.

Additionally, when measuring resonant light scattering spectral shifts, it is imperative that the wavelength component of the acquired scattering spectra be known with high precision. Timing uncertainty between the startup of the laser scan and the start of computer data acquisition can result in apparent spectral shifts in the data when no true shift has occurred. The spectral data must therefore be corrected to remove any spurious "timing" shifts. To determine how large a wavelength correction is needed, it is necessary to record a reference spectrum with known and stable features for wavelength registration. To accomplish wavelength correction/registration with sufficient precision, it is further important that the spectral features in the reference spectra be fairly sharp. This correction may be done using etalons (a device used in spectroscopy to measure wavelengths by interference effects produced by multiple reflections between parallel half-silvered glass or quartz plates) to produce wavelength reference signals which can be aligned very accurately, as described in detail in Example 3 below.

FIGS. 10–16 illustrate the detection of protein layers on a 40-micrometer diameter microparticle, using etalon correction, according to the present invention. Details are given in Examples 3–6.

A significant advantage of the present invention is the potential elimination of binding-related reporter groups in a particle-based assay. Some non-labeled binding methods have been developed for fixed arrays and on other fixed surfaces (for example using surface plasmon resonance in a planar biosensor according to Larsson, A. and Persson, B., "Method for nucleic acid analysis", U.S. Pat. No. 6,207,381 and Lyon, L. A. et al., "An improved surface plasmon resonance imaging apparatus", *Rev. Scientific Instruments* 70, 2076–2081 (1999); Thiel, A. J. et al., "In situ surface plasmon resonance imaging detection of DNA hybridization to oligonucleotide arrays on gold surfaces", *Anal. Chem.* 69, 4948–4956 (1997)). However, no such label-free methods exist for particle-based assays. Methods described in the literature relating to particle-based assays, fluorophores, chromophores, nanoparticles, or other reporter groups are either bound to the target or associated in some way with the binding event. A typical measurement is thus the amount of reporter bound to the particle by its association with the target. Before the measurement is made, the excess unbound reporter must be washed away to eliminate high background readings. This takes time and eliminates the opportunity for dynamic measurements, since essentially only an end point is detected.

In the present invention, since only bound material is detected by means of wavelength shifts in the scattered light spectrum, the presence of unbound targets does not interfere with the measurement in any way. A reporter group is not required for this invention; however, a species associated with the target could still be used to increase assay sensitivity by enhancing the perturbation of refractive index near the particle surface upon binding. Such a signal amplification means would preferably be a small, dielectric particle attached to the analyte, for example a titanium dioxide or silica nanoparticle. The particle should be small enough not to interfere with binding between probe and target and also small enough not to interfere with the detection of scattered light resonances. Typically such a particle would be several nanometers to tens of nanometers in size.

Another approach toward signal amplification would be to employ a chemical reaction, such as an enzymatic reaction, antibody/antigen reactions, or in situ nucleic acid amplification methods such as rolling circle amplification. Such a method would be specifically triggered to add mass to the particle surface only when binding of a specific target occurs. Whether or not a signal amplifying species is used, the washing step required in literature methods is made optional and, most importantly, the measurement of binding can still be made in real time during the course of the experiment. This feature of the invention enables an entirely new class of particle-based assay measurements, namely the rapid, massively parallel determination of time-dependent binding on a large population of identifiable microparticles, each carrying on its surface a known capture probe. Those skilled in the art would appreciate the large opportunity for applications of this technology in such diverse areas as drug target screening, proteomics, gene or protein expression analysis, and the like.

An additional advantage of the invention is that a unified detection method and system may be employed for determining both the particle identity and the degree of binding of an analyte. It should be noted that the identity of a particle is contained in the relative pattern of spectral features and not in the absolute locations of the features. When a target is bound, the relative pattern (i.e. the particle identity) is preserved while the pattern shift is indicative of the degree of analyte binding. The use of a unified detection method results in a simpler overall system with fewer reagents, less hardware, and simplified protocols compared to current methods, resulting in a faster, less costly, and more automatable system.

The final step to determining the presence and optionally the concentration of a given analyte is the association of a specific probe or capture probe with the microparticle whose scattering spectrum has shifted. As explained previously, in a preferred embodiment of the present invention, this association may be provided by the unique identity of the microparticle as reflected in the pattern of resonant light scattering spectral features. By this method, the binding properties of a complex sample can be determined in a single experiment, including not only which specific targets have bound but also the kinetics of binding under defined conditions. Alternatively, the probe and analyte identity may be determined by other techniques already known in the art, while the presence and optionally the concentration of a given analyte is determined by resonant light scattering, as illustrated in the following Examples.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience, New York, N.Y. (1987).

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "Å" means angstrom(s), "mM" means millimole, "M" means molar, "mmol" means millimole(s), "µmol" means micromole(s), "pmol" means picomole(s), "nmol" means nanomole(s), "g" means gram(s), "µg" means microgram(s), "mg" means milligram(s), "V" means volts, "dc" means direct current, "g" means the gravitation constant, "W" means watt(s), "mW" means milliwatt(s), "PBS" means phosphate-buffered saline, "rpm" means revolutions per minute, and "PEGM" means poly(ethylene glycol) methacrylate.

The resonant light scattering spectral shifts reported in the following Examples are given as the mean±the standard deviation.

Example 1

Identification of Individual Glass Microparticles by Resonant Light Scattering

The purpose of this Example was to demonstrate the identification of individual glass microparticles using resonant light scattering spectra using an optical probe system.

Spherical glass microparticles of refractive index approximately 1.9 and diameter approximately 35–40 µm (MO-Sci Corp., Rolla, Mo., Product number GL-0175, Lot 7289552-S1) were used without further treatment. Approximately 0.5 g of particles was placed in approximately 10 mL of distilled water and a suspension was created using a magnetic stir bar. A sample of approximately 0.1 mL of this suspension was placed on the top Teflon® AF 2400 (DuPont Co., Wilmington, Del.) window of thickness about 2 mm 001 as shown in FIG. 3. The suspension was optionally covered with a Teflon® AF 2400 cover film (about 0.05 to 0.13 mm thickness) 003 and the glass microparticles 002 were allowed to settle to the upper surface of the top window 001. The cell was then sealed with screws. The cell was placed on a translation stage in the detection apparatus of FIG. 4. The center excitation fiber 004 of a multi-fiber optical probe 005 (RoMack, Inc., Williamsburg, Va.) was connected to a tunable diode laser light source 006 (Model AQ4321, Ando Electric Co. Ltd., Germantown, Md.). A chopper internal to the laser controller was used to modulate the laser light. The outer six collection fibers 007 were optically combined and the combination connected to a light detector 008 (Model 2011, New Focus Inc., San Jose, Calif.). The signal output was in turn routed to a lock-in amplifier 009 (Model 5301A, EG&G Princeton Applied Research, Oak Ridge, Tenn.) used in synchronous detection mode with the chopper. The output of the lock-in amplifier was routed to a data acquisition board (PCI-6110E, National Instruments, Austin, Tex.) installed in a personal computer 010 (Dell Precision 420 Workstation, Dell Computer Corporation, Round Rock, Tex.). Custom software was written to control the laser scan and to acquire and display the scattered light intensity as a function of wavelength.

To acquire a scattered light spectrum from a single particle, the fiber optic probe 005 was centered above one particle by moving the translation stage 011 containing the optical cell 014 with the aid of a microscope-mounted video camera 012 (model KP-M2RN CCD camera, Hitachi Instruments, San Jose, Calif., coupled to a Wild Makrozoom Type 246634 microscope 013, Leica Microsystems, Bannockburn, Ill.) mounted underneath the cell. The image of field of view of the fiber optic probe was displayed on a video monitor 017. An additional layer of water 016 was used to optically couple the detection probe with the sample microparticles. Once the probe was aligned with a single particle, the diode laser 006 was scanned in wavelength (typically from 1570 to 1620 nm in 20 s). The resulting scattered light spectrum was acquired, displayed, and stored on disk. This process was repeated to acquire spectra from other particles in the sample. A representative set of spectra is shown in FIG. 5. It can be seen that each particle has a unique scattering spectrum. These spectra could be further subjected to automated spectral analysis techniques in order to extract features that uniquely identify each particle.

Example 2

Identification of a Multiplicity of Glass Microparticles by Resonant Light Scattering Imaging The purpose of this Example was to demonstrate the identification of a multiplicity of glass microparticles by resonant light scattering using a spectral imaging system.

The spectral imaging system shown in FIG. 7 was used to acquire and process resonant light scattering spectra from multiple glass microspheres simultaneously. The optical cell of FIG. 3 was modified as shown in FIG. 6 by replacing the water underneath the top Teflon® AF 2400 window with an ink absorber solution 018, which consisted of 1 part ink (Higgins Fountain Pen India Ink, Item 46030-723, Sanford Co., Bellwood, Ill.) to 100 parts distilled water. The ink solution served to absorb any incident light that had not interacted with the microspheres, thereby reducing optical noise from scattering and back reflection. The imaging optical cell 019 was loaded with glass microparticles 002 as in Example 1 and placed in the stage of a commercial optical microscope 021 (Model DMRXE, Leica Microsystems) fitted with objective lens 020. Particles with an index of refraction of approximately 1.9 comprised about 70% of the particles of this Example; particles with an index of refraction of approximately 1.7 comprised about 30%.

The Teflon® AF film 003, used for isolating the particles and their liquid environment from the optical system, was optional and did not affect the results of the analysis. The use of such a film, or its equivalent, was determined by the length of the experiment, the temperature, the rate of evaporation loss from the solution surrounding the particles, the time scale of the experiment, and other factors. When the film 003 was used, an additional layer of water was added between the film and the optical probe in order to provide efficient optical coupling of the signal. The microscope 013 was set up for bright field illumination using a diode laser 022 (Model Velocity 6312, New Focus, Inc.) as the light source. The output of the laser was coupled into a 4 mm diameter plastic fiber 023 and the output of this fiber placed in the illumination optical train of the microscope, replacing the standard light source. The fiber was mechanically vibrated by attaching the shaft of a miniature "buzzer" motor 024 (Marlin P. Jones & Assoc. Inc., Lake Park, Fla., Item #12342-MD), driven by approximately 3 V dc, directly to the fiber. This vibration served to eliminate the laser speckle pattern in the illumination field, which would otherwise interfere with the acquisition and analysis of image data. The standard beam splitter installed by the microscope manufacturer was replaced by a pellicle-type beam splitter 025 (Edmund Industrial Optics, Barrington, N.J., Item #A39-481) in order to further eliminate interference fringes in the image.

To acquire scattering spectra from a multiplicity of particles simultaneously, a set of particles was first placed in the field of view of the microscope and focused with the objective lens 020. Depending on the wavelength of the diode laser, this was accomplished by illuminating the sample, either with the laser itself or with an alternate light source that temporarily replaced the laser, for example a helium-neon laser. Once the particles of interest were in the field of view and focused, the laser was scanned in wavelength, typically from 770 to 780 nm in 20 s. During this scan, the digital camera 026 (Model KP-M2RN, Hitachi Instruments) acquired a complete scattered light image of the field of view at each wavelength. Each image was captured by an image capture board 027 (IMAC PCI-1409, National Instruments) installed in a personal computer 010 (Dell Precision 420 Workstation). Custom software was written to store each image. A wavelength scan resulted in a set of linked images, one for each wavelength in the scan. A typical image is shown in FIG. 8.

To determine the scattering spectra of each particle in the field of view from a set of wavelength-linked images, software was written to identify a representative region or regions of the image corresponding to each particle, for example a portion of the ring-shaped scattered light image 106 surrounding the bright spot of reflected light 107 at each particle center as seen in the image of FIG. 8. In this Example, the incident and scattered light beams were polarized independently, with the two axes of polarization parallel to each other. This results in sectors of scattered light centered approximately at the 12:00, 3:00, 6:00, and 9:00 positions of the circle as indicated for the center image of FIG. 8 by the numbers 12, 3, 6, and 9 respectively. Theory predicts, and results confirm, that scattered light spectra from the "12" and "6" regions are equivalent and scattered light spectra from the "3" and "9" regions are equivalent. Furthermore, spectra from the two pairs of sectors are different from one another. This results in the ability to identify a particle by a combination of two substantially independent spectra, rather than a single spectrum, increasing the multiplicity of identifiable particles and also the accuracy of identification.

The concept of polarization-dependent spectra is illustrated for a single particle in FIG. 9. Regions at "12" and "3" positions were identified as the regions of interest from which pixels were chosen to represent the particle's scattering spectrum. The pixels were chosen as follows. First a region of the image (for example, at 12:00 in FIG. 9) was selected from the larger image. Within the selected area, software calculated the spectra represented by each pixel in the stack of images L1, L2, L3 . . . Ln, where each image is acquired at a single wavelength. Then a selection algorithm was used to choose those pixels for which the corresponding spectra met or exceeded a selection criterion. In this Example, the criterion was to select the 10 to 20 pixels in the selected area for which the quantity (Max−Min)/Min was the highest (if Min=0, the software set Min=1), where Max is the maximum value of the intensity in the spectrum and Min is the minimum value of the intensity in the spectrum.

The spectra for these pixels were then averaged. Examples of such spectra are shown on the right side of FIG. 9. Shown are spectra for the "12" and for the "3" regions. As indicated above, the spectra for these regions are different.

The above pixel selection criterion is illustrated as an example only, and represents one measure of the contrast between spectral peaks and the underlying spectral baseline. Other criteria, or combination of criteria, could also be used to select specific pixels from a larger set.

The use of unique spectra to identify a multiplicity of particles is illustrated by the following example. Pairs of spectra (one from the "12" and one from the "3" region of each particle) were obtained from 87 different particles as explained above. Each spectrum contained 1500 data points from wavelength 770 nm to 780 nm. These spectra were used as "fingerprints" to identify the particles. Each particle's "12" spectrum was compared to the "12" spectra of all the other particles in the set. Quantitatively, the correlation coefficient squared (R-squared) was calculated between each particle's "12" spectrum and all the other particles' "12" spectra. The same correlation calculation was done for each particle's "3" spectrum and all other "3" spectra in the set. The degree of uniqueness of each particle's "fingerprint" was determined by determining if any particle (say Particle n) appeared sufficiently similar to any other particle (say Particle m) in the set according to the following algorithm:

IF R-Squared(Pn, Pm, 12)>T AND R-Squared(Pn, Pm,3)>T
  THEN Particle_match=True
Otherwise: Particle_match=False
  Where:
  R-Squared(Pn, Pm, 12)=the correlation coefficient squared between the scattered light spectra of Particle n and Particle m, taken from the "12" position of the scattered light image
  R-Squared(Pn, Pm, 3)=the correlation coefficient squared between the scattered light spectra of Particle n and Particle m, taken from the "3" position of the scattered light image T=a threshold value Particle_match=True if the particles are considered to have the same identity, False otherwise The purpose of developing pixel selection and particle similarity criteria was to develop an effective means for uniquely identifying all particles in a set. Ideally, if the spectra are sufficiently unique, and the threshold is chosen appropriately, no particle matches should exist by the above algorithm. In this Example, setting T between 0.75 to 1.0 resulted in completely unique spectral signatures for all 87 particles. This means there were no "false positives", i.e., two particles assigned as matched. Reducing T to 0.60 resulted in 10 false positives out of 4950 combinations (accuracy reduced from 100% to 99.8%), since the stringency of match is reduced and particles that are somewhat similar are now accepted as identical. Thus, in this Example, a threshold of 0.75 was appropriate to prevent false positives.

It was also necessary to test for "false negatives", i.e., when two scans of the same particle, taken at different times, under different environmental conditions, or with slight variations in the pixel selection criterion, fail to match by the algorithm chosen. The ability to faithfully identify the particles in spite of such variabilities was tested in the following way. For 4 of the particles, different, independent spectral scans of the same particle, taken at different times or by using small variations on the pixel selection criterion, were used as image data sources. A total of 13 different variations of these particles were used. Again, setting T=0.75 resulted in perfect matches with no false negatives. Increasing T to 0.90 resulted in 7 false negatives out of 4950 combinations (accuracy reduced from 100% to 99.9%), and at T=0.95 the accuracy was reduced from 100% to 99.7% (14 false negatives out of 4950 combinations). This reflects the fact that when using very high stringency requirements, small variations in spectra from the same particle under slightly different conditions can lead to a failure to match. However, this Example clearly shows that for a representative set of particles, a pixel selection criterion and a similarity criterion can be defined such that very high accuracy of particle identification can be obtained.

The Example shown here is for illustration only, and could readily be extended and automated to identify and track larger numbers of particles. For example, advanced pixel selection criteria, pattern recognition techniques, and spectral coding methods could be developed by one skilled in the art to locate and identify each particle in a field of many particles.

Example 3

Detection of Binding of Avidin on Biotinylated Microparticles Using Resonant Light Scattering The purpose of this Example was to demonstrate detection of avidin binding to biotinylated glass microparticles using resonant light scattering. Amine groups were introduced on the surface of glass microparticles using silane chemistry. Then, the microparticles were biotinylated by reaction with Sulfo-NHS-SS Biotin. Avidin binding to the biotinylated microparticles was detected using resonant light scattering. Reversibility of the binding signal upon cleaving the avidin from the particle was also demonstrated.

A. Surface Preparation of Microparticles:

High-refractive index glass microparticles (Mo-Sci Corp., Rolla, Mo., Product number GL-0175, Lot 7289552-S1, refractive index approximately 1.9) were first cleaned by leaching with 0.5 M $HNO_3$ at room temperature for 5 min. The glass particles were then treated with the following series of steps: a deionized water rinse, treatment with 5–10% NaOH at room temperature for 30 min, a water rinse, and drying at 110° C. in a vacuum oven overnight.

The cleaned glass microparticles were silanized with 3-aminopropyl triethoxysilane (Aldrich, Milwaukee, Wis., product number 440140, lot number 20515DA) by refluxing in anhydrous toluene for 24 h to introduce amine groups on the surface of the particles. The reaction mixture was filtered to isolate the silanized microparticles. The silanized microparticles were then rinsed with toluene and acetone in sequence, followed by drying in air for 0.5–1 h and cured at 110–120° C. in an oven for a period ranging from 4 h to overnight.

The surface coverage of amine groups on the silanized microparticles was determined by titration. Before the titration, 0.3 g of silanized microparticles was dispersed in 50 mL of distilled water that contained 1 mL of a 1% acetic acid solution. The acetic acid was used to soften the glass microparticles to allow the titrant access to all amine groups. The microparticle dispersion was stirred and heated to 40° C. for 4 h, then allowed to cool to room temperature prior to titration. The surface amine groups on the microparticles were then titrated using diluted perchloric acid (0.0259 N) as titrant. The surface amine coverage was found to be 0.045 mmol per gram of microparticles. The silanized microparticles were also analyzed using ESCA (Electron Spectroscopy for Chemical Analysis). The ESCA results indicated that about 5% of the silanized microparticle surface elements were nitrogen atoms from the amine groups.

B. Microparticle Surface Biotinylation:

Biotinylation was carried out by incubating the silanized microparticles in 2-fold molar excess of sulfosuccinimidyl-2-(biotinamido) ethyl-1,3-dithiopropionate (Sulfo-NHS-SS-Biotin) (Pierce Biotechnology Inc., Rockford, Ill.; product number 21331, lot number DD53927), dissolved in pH 7.4, 0.1 M phosphate buffered saline (PBS) at a concentration of 25 mg/mL. The microparticles were incubated in this solution for 0.5–1 h at room temperature. The surface amine groups react with N-hydroxysulfosuccinimide (NHS) at neutral pH values and above, resulting in covalent binding of biotin to the microparticle surface. The unreacted Sulfo-NHS-SS-Biotin was removed with a buffer wash using a microconcentrator (Centriplus® Centrifugal Filter, Model YM-100, Millipore Corporation, Bedford, Mass.). The biotinylated microparticles were then dried in vacuum at room temperature overnight.

C. Biotin-avidin Binding:

A procedure based on Example 2 was used to measure the scattered light spectrum of the microparticles. The biotinylated microparticles prepared by the procedure of part B were dispersed in pH 7.4, 0.4 M (0.1 M sodium phosphate, 0.3 M NaCl) PBS buffer. An aliquot of this suspension was placed in an optical cell. For this experiment, the cell 019 shown in FIG. 6 was modified for use as a flow cell by removing the upper Teflon® AF film 003 and incorporating fluid inlet and outlet ports on the side of the cell. A field of view was selected that contained a number of microparticles. The diode laser light source 022 was then scanned between 770 and 780 nm in 50 s. At each wavelength interval, a digital image of the scattered light from all particles in the field of view was acquired by the image capture board 027 and the data was stored and analyzed by software installed in the personal computer 010. Several microparticles in the field of view were selected for subsequent detailed spectral analysis, for example as shown in FIG. 10A. FIG. 10A is one of the 1500 individual scattered light images taken during a wavelength scan, one for each wavelength step. By analyzing the full set of wavelength-dependent scattered light images as described in Example 2, a scattered light spectrum from this particle was obtained. The scattered light spectrum from the upper left microparticle of FIG. 10A is shown in FIG. 10B.

To bind avidin to the biotinylated surface, a solution consisting of 56 µg/mL of fluorescein isothiocyanate-labeled avid in (FITC-avidin) (Sigma Chemical Co., St. Louis, Mich., product number A2050, Lot 091K4842, FITC/protein molar ratio=3.9) in pH 7.4, 0.4 M PBS buffer was flowed through the biotinylated microparticles for 15 min at a flow rate of about 1.45 mL/min. The sample cell was then flushed with pure PBS buffer, so that the resonant light scattering was measured in the same medium as that used before binding. The binding was confirmed independently by fluorescence detection of the fluorescein label.

To accurately measure the absolute wavelength shift between scattered light spectra, it is necessary to account for variations in laser scan trigger timing. This was done by using two etalons to produce wavelength reference signals which can be aligned very accurately, thus correcting for any scan timing variability. The etalon referencing technique is explained in more detail in Section E, infra. One example of wavelength-aligned spectral comparison before and after avidin binding is shown in FIG. 10C. The shift was quantified by calculating the cross-correlation coefficient squared (R-squared) between the spectra before and after binding of FITC-avidin, as a function of an induced wavelength shift between the spectra. One of the two spectra was artificially shifted in wavelength relative to the other, and the R-squared value between them was calculated. The spectrum was then shifted again; the R-squared value was recalculated, and so on, generating a relationship between the shift and the correlation. The R-squared value would be expected to maximize at the wavelength shift corresponding to the natural shift induced by addition of the FITC-avidin to the microparticle. The results of this analysis are shown in FIG. 11 in which the shift is expressed as the difference between the maximum of etalon correlation and the maximum of the scattering spectra correlation. After spectral alignment, the wavelength shift induced by avidin binding was $0.034\pm0.007$ nm for a data set consisting of 54 independent laser scan comparisons over four independent particles and also over two different days.

A comparable data set from another experimental run on a different date, using the same protocol as above, yielded a wavelength shift of $0.038\pm0.010$ ($N=36$ measurements, one particle) upon specific binding of avidin, showing good day-to-day reproducibility of the spectral shift measurements.

The binding of avidin on biotinylated microparticles was also quantified using the Bradford method for protein determination (Bradford, *Anal. Biochem.* 72, 248–254 (1976)). As the biotinylation reagent Sulfo-NHS-SS-Biotin adds a disulfide bond in the biotin-microparticle linkage, the entire avidin-biotin conjugate can be cleaved from the microparticle by reducing agents such as 2-mercaptoethanol or dithiothreitol (DTT). After a 40 min incubation of the avidin-bound microparticles in 50 mM DTT (Sigma Chemical Co., product number D-9779, lot number 072K0916) in pH 7.4, 0.4 M PBS, the Bradford method was used to determine how much avidin was released in the incubation supernatant. The result was 2.28 nmol of avidin per gram of microparticles, corresponding to approximately a monolayer coverage of avidin on the microparticles.

D. DTT Cleavage:

Reversibility of the resonant light scattering spectrum shift resulting from avidin binding was tested by removing the biotin/avidin complex from the microparticles by DTT treatment. DTT reduced the disulfide bonds of the biotin linkage to the microparticles obtained in step B. About 40 mL of 50 mM DTT in pH 7.4, 0.4 M PBS was passed through the optical cell and over the microparticles, followed by a 15 min incubation. The sample cell was then flushed with pH 7.4, 0.4 M PBS, and resonant light scattering spectra were taken. The scattering spectra before and after DTT treatment are given in FIG. 12 and the relative shift, as measured by autocorrelation function, as explained above, is shown in FIG. 13. The reverse shift induced by DTT treatment was confirmed by multiple runs and different microparticles, and the average was $-0.034\pm0.007$ nm, indicating the removal of the biotin/avidin complex from the microparticles.

These results demonstrate that it is possible to detect protein binding and release on a multiplicity of microparticles using resonant light scattering.

E. Wavelength Alignment Using Etalons:

When measuring resonant light scattering spectral shifts, it is imperative that the wavelength component of the acquired scattering spectra be known with high precision. Timing uncertainty between the startup of the laser scan and the start of computer data acquisition can result in apparent spectral shifts in the data when no true shift has occurred.

The spectral data must therefore be corrected to remove any spurious "timing" shifts. To determine how large a wavelength correction is needed, it is necessary to record a reference spectrum with known and stable features for wavelength registration. To accomplish wavelength correction/registration with sufficient precision, it is further important that the spectral features in the reference spectra be fairly sharp.

We chose to use planar etalon spectra as the reference spectra. An etalon is a device used in spectroscopy to measure wavelengths by interference effects produced by multiple reflections between parallel half-silvered glass or quartz plates. We used two glass plates with different thickness (specifically, 1 mm and 0.15 mm thick borosilicate glass) to give us a high and low frequency component in the interference pattern. The equation for the transmission of an ideal etalon, an Airy Function, is $$T = \left[1 + \frac{4R}{(1-R^2)}\sin^2\left(\frac{\phi}{2}\right)\right]^{-1}$$

where:
T=transmission
R=reflectivity of the mirrors
φ=the roundtrip phase change of the light ray If any phase change at the mirror surfaces is ignored then $$\phi = \frac{2\pi}{\lambda} 2nd \cos\theta$$

where:
λ=the wavelength of the light
n=the index of refraction of the material between the mirrors
d=the distance between the mirrors
θ=the angle of the incoming light beam The two etalons of different thicknesses, and thus giving rise to different spectral frequencies (or relatively "broad" and "narrow" interference fringes), were used in series to eliminate the possibility of misaligning the data if a false "timing" shift was more than a single narrow interference fringe. Each time a laser scan was taken, an etalon spectrum was acquired simultaneously with a resonant light scattering spectrum. The reference etalon spectra for two laser scans to be compared were analyzed by an autocorrelation algorithm to determine the magnitude of any false spectral shift, which was then used to correct the resonant light scattering data. The two spectra were shifted incrementally in wavelength relative to one another, and the autocorrelation coefficient between them was computed at each wavelength increment. The maximum of the autocorrelation coefficient occurred when the spectra were best aligned, and the wavelength shift corresponding to the maximum correlation of the reference etalon spectra was used to correct the apparent shift in the corresponding resonant light scattering spectra.

An example of two scattered light spectra to be compared for spectral shift is shown in FIG. 14A. As shown, these spectra have not been wavelength-aligned so the true spectral shift is unknown. During each wavelength scan, a portion of the incident light is routed to the etalons simultaneously, thus producing an interference pattern that accurately reflects the wavelength scale for that scan. An example of two etalon spectra associated with the two scattered light spectra to be compared are shown in FIG. 14B. A correlation analysis was then performed between the original pair of spectra (FIG. 14A) and between the pair of etalon traces (FIG. 14B). An example of such an analysis is shown in FIG. 14C, which shows the original spectra to be shifted 0.185 nm and the etalon spectra to be shifted 0.145 nm. Therefore, the net shift of the scattered light spectra due to binding is the difference between these two shifts or 0.040 nm. The wavelength-corrected spectra are shown in FIG. 14D.

Example 4

Detection of Multiple Protein Layer Binding in a Biotin-Avidin-Based Sandwich Assay Using Resonant Light Scattering The purpose of this Example was to demonstate the measurement of multiple protein layer binding, based on biotin-avidin interaction, on glass microparticles using resonant light scattering. Biotinylated glass microparticles were reacted in sequence with avidin, biotinylated anti-bovine IgG, and bovine IgG. The binding after each step was detected using resonant light scattering.

A. Surface Preparation and Microparticle Surface Biotinylation:

The same high refractive index glass microparticles and the same microparticle surface biotinylation protocol as described in Example 3 (steps A and B) were used.

B. Biotin-avidin Binding:

For in situ binding detection using resonant light scattering, the same procedure as described in Example 3 was used. Before avidin binding, resonant light scattering spectra were taken on biotinylated microparticles in pH 7.4, 0.15 M (0.01M sodium phosphate, 0.14 M NaCl) PBS. Then 20 mL of a solution consisting of 75 μg/mL avidin (from egg white, Sigma Chemical Co., product number A9275, lot number 22K7017) in pH 7.4, 0.4 M (0.1 M sodium phosphate, 0.3 M NaCl) PBS buffer was passed through the sample cell containing the biotinylated microparticles at a flow rate of about 1.5 mL/min. The cell was then flushed with pure pH 7.4, 0.15 M PBS, so that the resonant light scattering was measured in the same medium as that used before binding.

C. Avidin-biotinylated Antibody Binding:

After step B, 20 mL of a solution consisting of 50 μg/mL of biotinylated anti-bovine immunoglobulin G (IgG) [H+L] [Goat] (Rockland Inc., Gilbertsville, Pa., product number 601–1602, lot number 1040, biotinylation sites were randomly distributed over the whole IgG molecule, about 10–20 biotinylated sites per IgG molecule) in pH 7.4, 0.15 M PBS was passed through the sample cell at a flow rate of about 1.5 mumin. The microparticles were then incubated in the biotinylated anti-bovine IgG solution for 1 h. Afterwards, the sample cell was flushed with the same PBS, and multiple resonant light scattering spectra were taken.

D. Antibody-antigen Binding:

After Step C, 20 mL of a solution consisting of 50 μg/mL of bovine IgG (Sigma Chemical Co., product number I-5506, lot number 042K9023) in pH 7.4, 0.15 M PBS was passed through the sample cell at a flow rate of about 1.5 mL/min. The microparticles were then incubated in the bovine IgG solution for 1 h. Afterwards, the sample cell was flushed with the same PBS, and multiple resonant light scattering spectra were taken.

Examples of the spectra from steps B–D are shown in FIG. 15. All spectra were aligned with etalon correction, as described in Example 3. The spectrum shifts of steps B, C and D compared to the reference (unbound) state were, respectively 0.031±0.005 nm, 0.069±0.007 nm and 0.077±0.008 nm, determined by the autocorrelation method (all averages with N=18 measurements). These results show clearly that the sequential binding of avidin, anti-IgG, and IgG were individually measurable. The shift increase induced by bovine IgG binding was small compared to that induced by avidin binding and biotinylated anti-bovine IgG binding. It is most likely that the biotinylated anti-bovine IgG molecules bound to avidin in a random orientation, and their antigen binding ends were not optimally aligned and exposed for the binding of bovine IgG molecules.

E. DTT Cleavage

The same DTT treatment as described in Example 3 was performed to cleave the biotin/avidin/anti-IgG/IgG complex from the microparticles. The reverse spectral shifts were observed for all different runs and microparticles, and the average shift relative to the starting condition was 0.026±0.008 nm (N=18 measurements). These results indicate that most bound protein layers were released from the microparticles upon DTT treatment, and only a part of the first biotin/avidin layer was left on the surface.

Example 5

Detection of Multiple Protein Layer Binding in a Protein G-Based Sandwich Assay Using Resonant Light Scattering The purpose of this Example was to demonstrate the measurement of multiple protein layer binding with controlled orientation on glass microparticles using resonant light scattering. Protein G' was coupled to amine-derivatized microparticles with a bifunctional crosslinking agent. The binding of mouse IgG and then, anti-mouse IgG to the Protein G' microparticles was detected using resonant light scattering.

A. Surface Preparation and Derivatization of Protein G' on the Microparticle Surface:

The same high refractive index glass microparticles (RI=1.9, Mo-Sci GL-0175) and the same amino silanization protocol as described in Example 3 (step A) were used to introduce amine groups on the microparticle surface. Such microparticles are herein referred to as amine microparticles. Protein G is a bacterial membrane protein prepared from a group G *Streptococcal* strain. It can specifically bind the constant region (Fc) of mammalian IgG molecules. Therefore, protein G can be used to control the orientation of the IgG molecules. Protein G' is a truncated protein which lacks the albumin, Fab, and membrane binding sites while retaining the Fc binding site; therefore it is more specific for IgG than the native form. Protein G' was coupled to the amine microparticles with the bifunctional linker dimethylpimelimidate•2HCL (DMP). Protein G' (Sigma Chemical Co. product P-4689, Lot 042K15451) was lyophilized from Tris-HCl buffer, and needed to be buffer exchanged to the crosslinking buffer (pH 8.0, 0.1 M PBS). Protein G' (1 mg) was dissolved in 0.5 mL of deionized water, and the buffer salts were removed using a Centriplus® YM-10 microconcentrator (Millipore Corp., Billerica, Mass.). This process was repeated three times, and Protein G' was reconstituted with 0.5 mL of pH 8.0 PBS. At the same time, about 10 mg of DMP (Pierce Biotechnology Inc., Rockford, Ill.; product number 20666, Lot DH55682) was dissolved in 1 mL of pH 8.0, 0.1 M PBS and then 0.6 g of amine microparticles was added to the DMP solution. This mixture was vortexed and then incubated at room temperature for about 0.5 h. After this time, the excess DMP was washed away with PBS buffer using the microconcentrator, and the DMP-reacted microparticles were transferred to the protein G' solution. The microparticle suspension was vortexed, and then incubated for about 1.5 h while mounted on a rotator. Then, the supernatant was removed and pH 8.5, 0.2 M Tris buffer was added to quench the reaction and the solution was incubated for 1 h. The microparticles were then washed thee times with PBS buffer, using a centrifuge with a swinging-bucket rotor to collect the microparticles.

The Protein G' microparticles were tested using a direct ELISA (Enzyme Linked Immunosorbent Assay) to verify that the Protein G' was successfully coupled to the microparticles and to determine the probe density. In the ELISA test, a series of accurately weighted Protein G' microparticles and control microparticles, which did not contain Protein G', were incubated in Rabbit anti-Chicken IgY, (H+L), peroxidase conjugate (Pierce, Cat. No. 31401, a Rabbit IgG peroxidase conjugate) at different concentrations. Then, the microparticles were washed seven times. OPD substrate (Pierce, Cat. No. 34006) solution was added to each protein G' microparticle sample and control microparticle sample and the samples were incubated for 15 min. After this incubation, stopping solution (1 M sulfuric acid) was added to each sample. The peroxidase conjugate standards were treated in the same manner. The supernatant from each microparticle sample and the standard solution of equal volume were transferred to a 96 well microtiter plate to measure the absorbance. There was very little absorbance from the control microparticle samples. The saturated absorbance obtained at high enzyme conjugate concentration for protein G' microparticles was used to calculate the protein G' surface density. The calculated protein G' surface density was 0.44 pmol per gram of microparticles with the assumption that each Protein G' molecule binds two IgG molecules (Akerstrom, B. and Bjorck L. *J. Biol. Chem.*, 261, 10240–10247 (1986)). Compared to the activity of the free enzyme in solution, the activity of an immobilized enzyme might be reduced. Therefore, the ELISA result was not accurate based on a standard curve acquired from the free enzyme and an enzyme activity-reducing factor was determined and used for activity correction. Binding experiments were carried out with incubation of excess Protein G' microparticles in very dilute solutions of rabbit anti-chicken IgY, (H+L), peroxidase conjugate. The enzyme activity taken up by the particles was determined from the difference in enzyme activity in the peroxidase conjugate solution before and after binding to the Protein G' microparticles. The enzyme activity on the particles was then measured. The enzyme activity-reducing factor was calculated as the ratio of enzyme activity taken up by the Protein G' particles to the enzyme activity measured on the particles. The enzyme activity-reducing factor was determined to be 26, 19 and 18 in three tests. The median activity-reducing factor of 19 was used to correct the Protein G' surface density, resulting in a corrected Protein G' surface density of 8.36 pmol per gram of microparticles.

A second approach was also used to determine the probe surface density. Protein G, Alexa Fluor488 conjugate (Molecular Probes, catalog number P-11065) was coupled to the amine microparticles with a cleavable bifunctional linker 3,3'-dithiobis(sulfosuccinimidylpropionate) (DTSSP, Pierce, Catalog number 21578), in the same way that Protein G' was coupled to the amine microparticles with DMP. The Protein G, Alexa Fluor488 conjugate was then cleaved with 50 mM DTT at 37° C. overnight to ensure complete cleavage. The supernatant from the cleavage was examined with a spectrophotometer, and the absorbance at 494 nm was used to calculate the concentration of the Alexa Fluor488 dye using the manufacturers suggested extinction coefficient of 71,000 $cm^{-1}$ $M^{-1}$. The Protein G concentration was then calculated from the ratio of 2.3 moles of dye per mole of protein which was determined by the manufacturer. The results indicated that the Protein G density was 1.3 nmol per gram of microparticles, about 150 times larger than the corrected ELISA result. This result suggested that the enzyme activity-reducing factor may not be sufficient to correct the ELISA results for the Protein G probe density determination on the microparticles. However, the ELISA test can be applied to microparticles prepared from all linking chemistries, and was used for probe density measurements on most of the derivatized microparticles in this disclosure. The ELISA results are valid to compare probe derivation efficiency from batch to batch, but may not be suitable to determine an absolute number for the probe density.

B. Mouse IgG Binding:

The same procedure as described in Example 3 was used for in situ binding detection with resonant light scattering. Before the mouse IgG binding, resonant light scattering spectra were taken on Protein G' microparticles in pH 7.2, 25 mM (10 mM sodium phosphate, 15 mM NaCl) PBS buffer as the reference spectra. Then, 15 mL of a solution consisting of 50 μg/mL mouse IgG (Sigma Chemical Co., product number 15381, lot number 042K9027) in the same pH 7.2 PBS buffer was passed through the sample cell containing the Protein G' microparticles with circulation at a flow rate of about 1.5 mL/min for 0.5 h. The sample cell was then flushed with pure pH 7.2 PBS buffer, so resonant light scattering was measured in the same medium as that used before binding.

C. Anti Mouse IgG Binding:

After step B, 15 mL of a solution consisting of 40 μg/mL Fab specific goat anti-mouse IgG (Sigma Chemical Co. product M 6898, Lot 012K4811) in pH 7.2, 25 mM PBS was passed through the sample cell with circulation at a flow rate of about 1.5 mL/min for 0.5 h. Afterwards, the sample cell was flushed with the same PBS, and multiple runs of resonant light scattering spectra were taken.

The correlation results indicated that the resonance shift after step B (mouse IgG binding on Protein G' microparticles) was 0.054±0.007 nm compared to the reference (unbound) state, and the shift after step C (anti mouse IgG binding to mouse IgG) was 0.111±0.016 nm compared to the reference (unbound) state. Therefore, with control of the IgG molecule orientation, the shift was proportional to the size of the binding molecules.

Example 6

Real Time Binding Detection Using Resonant Light Scattering

The purpose of this Example was to demonstrate real time detection of protein binding on glass microparticles using resonant light scattering. The binding of mouse IgG to Protein G' microparticles was measured as a function of time.

A. Surface Preparation and Derivatization of Protein G' on Glass Microparticles:

The same high refractive index glass microparticles (RI=1.9, Mo-Sci GL-0175) and the same Protein G' derivation protocol as described in Example 5 (step A) were used to make Protein G' microparticles.

B. Real Time Detection on Mouse IgG Binding:

For in situ binding detection with resonant light scattering, the same procedure as described in Example 3 was used. Before mouse IgG binding, resonant light scattering spectra were taken on Protein G' microparticles in pH 7.2, 25 mM (10 mM sodium phosphate, 15 mM NaCl) PBS buffer as the reference spectra. Then, 15 mL of mouse IgG (Sigma Chemical Co., product number I5381, lot number 042K9027) in the same pH 7.2 PBS buffer was passed through the sample cell containing the Protein G' microparticles with circulation at a flow rate of about 1.5 mL/min for about 30–60 min. Every 5 min, the circulation was stopped, resonant light scattering spectra were taken, and the circulation was restarted again. Therefore, binding dynamics could be followed in real time. At the end of the incubation, the sample cell was flushed with pure pH 7.2 PBS buffer, and resonant light scattering was measured in the same medium as that used before binding. These real time binding detection experiments were carried out with mouse IgG concentrations of 10 μg/mL, 50 μg/mL and 500 μg/mL. Autocorrelation analysis was used to obtain the resonance wavelength shift.

The results of this study, which show the change of resonance shift over time at the tested mouse IgG concentrations, are summarized in Table 1, and shown in FIG. 16. Each data point is the average over 3–4 different microparticles, and the error bars represent the standard deviation of the measurements. As can be seen from the data, the higher the mouse IgG concentration tested, the faster the resonance shift increased with time, indicating a higher rate of binding. The data also show that the resonance shift, and therefore the binding, reached a maximum when the mouse IgG concentration was over 50 μg/mL, while at the 10 μg/mL concentration, only about 70% of the saturation binding level was observed. Therefore, the resonant light scattering detection is sensitive enough to detect submonolayer binding.

TABLE 1

Mouse IgG Binding Dynamics

| Time (min) | Wavelength shift at 10 μg/mL mouse IgG (nm) | Wavelength shift at 50 μg/mL mouse IgG (nm) | Wavelength shift at 500 μg/mL mouse IgG |
|---|---|---|---|
| 0 | 0 | 0 | 0 |
| 5 | 0.010 ± 0.008 | 0.032 ± 0.006 | 0.037 ± 0.005 |
| 11 | 0.022 ± 0.007 | 0.037 ± 0.004 | 0.049 ± 0.010 |
| 16 | 0.026 ± 0.006 | — | 0.050 ± 0.005 |
| 20 | 0.030 ± 0.008 | 0.051 ± 0.012 | 0.053 ± 0.008 |
| 25 | 0.041 ± 0.010 | — | 0.052 ± 0.008 |
| 30 | 0.036 ± 0.009 | 0.058 ± 0.006 | 0.054 ± 0.009 |
| 35 | 0.036 ± 0.010 | 0.060 ± 0.008 | 0.054 ± 0.008 |
| 40 | 0.041 ± 0.010 | — | — |
| 50 | 0.043 ± 0.007 | — | — |
| 60 | 0.043 ± 0.007 | — | — |

Because there was no mixing involved in the process, the binding dynamics shown in FIG. 16 only reflect the diffusion limited binding rate. The real biological binding kinetics can be measured in real time with the use of a microfluidic mixing device to enhance the rate of mass transfer.

The resonance shifts measured after the buffer flush were the same as those obtained at the end of the incubation, but before the buffer flush. This result indicates that a low concentration of protein molecules in the buffered saline had almost no effect on the spectra from the medium in which the spectra were taken. Therefore, we could use the spectra taken in the pure buffer as the starting point and zero shift reference for the dynamic data taken in the mouse IgG solution. For real biological samples such as sera or cellular extracts, which have high concentration of proteins and nucleic acids, the resonant light scattering spectra will shift simply because of the medium change. For those cases, the starting point in the biological sample would be used as the reference point of zero shift for real time detection.

Example 7

Protein Binding Assay in a Serum Background Using Resonant Light Scattering Detection The purpose of this Example was to demonstrate specific binding detection in a serum background using resonant light scattering. The microparticles were coated with poly(ethylene glycol) methacrylate (PEGM) to reduce nonspecific binding and then a fluorescent dye, Alexa Fluor® 488, was coupled to the hydroxyl groups of the PEGM coating. Anti Alexa Fluor® 488 antibody binding to the fluorescent dye-coupled particles was detected in diluted rabbit serum using resonant light scattering.

A. Formation of a Nonspecific Binding Resistant Layer on the Microparticles Using Surface Initiated ATRP (Atom Transfer Radical Polymerization):

Real biological samples, such as sera and cellular extracts, normally contain analytes in a high concentration protein background. Nonspecific binding of background proteins to the microparticles leads to false diagnostic results and therefore, has to be prevented. We used a layer of poly(ethylene glycol) methacrylate (PEGM) coating, formed by surface initiated ATRP, to reduce nonspecific binding to the microparticles.

The synthesis procedure described by Husseman et al. (*Macromolecules* 32, 1424–1431 (1999)) was used to prepare the initiator 5-trichlorosilyl pentyl 2-bromo-2-methyl propionate. Then the initiator was reacted with the cleaned glass microparticles, as described below. The same high refractive index glass microparticles (RI=1.9, Mo-Sci GL-0175) and the same cleaning procedure as described in Example 3 (step A) were used, and the microparticles were dried at 110° C. in a vacuum oven overnight before use. All glassware was cleaned and dried at 110° C. in an oven for a period of 2 h up to overnight. One hundred milliliters of dry toluene (EM Science, product number TX0732-6) was added to a 250 mL round bottom flask, and 45 μL of pyridine (Aldrich, product number P57506, batch number 03012LA, dried with 4 Å molecular sieves overnight before use) was added. Then, 8 g of dried, clean microparticles and 250 μL of 5-trichlorosilyl pentyl 2-bromo-2-methyl propionate initiator were added. The flask was sealed with a glass stopper and the reaction proceeded at room temperature with vigorous stirring for 4 h. The microparticles were isolated by filtration and were rinsed with 100 mL of toluene and 100 mL of acetone in sequence. Then, the microparticles were collected, dried and cured at 110° C. in an oven for a period of 2 h up to overnight.

The initiator-loaded microparticles were then ready for polymerization. ATRP was conducted in aqueous solution at room temperature. The composition was optimized on the basis of the disclosure by Huang, in copending U.S. patent application Ser. No. 60/451,068, which is incorporated herein by reference. Forty six grams of poly(ethylene glycol) methacrylate (PEGM monomer, Aldrich, product P409537, batch 15304CB, average Mn=360) and 120 mL of deionized water were added to a 250 mL round bottom flask. The solution was stirred under nitrogen for 0.5 h. Then, 0.46 g of bipyridyl (Aldrich, product D216305, batch 08015CO) and 28 mg of $CuCl_2$ (Aldrich, product 203149, Lot 04907EA) were added, and the colorless solution turned light blue. Then, 140 mg of CuCl (Aldrich 224332, Lot 08319 JA) was added, and the solution turned dark brown. The nitrogen purge was continued for another 15 min, and then, 2 g of initiator-loaded microparticles was added. The reaction was sealed under a nitrogen atmosphere and allowed to proceed for 4 h. After this time, the microparticles were isolated by filtration and rinsed with abundant amounts of deionized water until the color was rinsed away. The microparticles were then collected and dried overnight in vacuum at room temperature.

The presence of the PEGM coating on the microparticles was confirmed using ESCA (Electron Spectroscopy for Chemical Analysis) and ToF-SIMS (Time of Flight Secondary Ion Mass Spectroscopy) imaging. With ESCA, the element composition in the top 100 Å of sample surface can be obtained. The elemental percentage for the surface of the PEGM coated microparticles and that of the bare glass microparticles, as determined by ESCA, is given in Table 2. As can be seen from the data in the table, most bulk elements present in the bare glass microparticles, such as Ba, Ti, B, Ca and Si, were not detected or were found to be present at significantly lower levels on the surface of PEGM coated microparticles, on which C was the major element found. This result indicates that there was good coverage of the PEGM coating on the surface of the microparticles. ToF-SIMS imaging can give spatial distribution of chemical species on the surface, and can be used to check the uniformity of the PEGM coating on individual microparticles. The results of the ToF-SIMS imaging revealed that, except for a few small spots of bulk metal ions on their surface, the majority of the microparticles' surface was covered with the PEGM coating.

The nonspecific adsorption of protein onto the PEGM coated microparticles was tested by exposing the particles to a solution consisting of 50 μg/mL avidin-FITC conjugate (Sigma Chemical Co., product number A2050, Lot: 091K4842) in pH 7.4, 0.4 M PBS buffer. The bare microparticles were treated in the same manner to act as the control. Fluorescence microscope examination of the microparticles indicated that the PEGM coated microparticles had significantly reduced nonspecific adsorption of avidin compared to the control. The reduction in nonspecific binding was greater after both the PEGM coated microparticles and the control microparticles were treated with a 0.25% BSA blocking step before exposure to the avidin-FITC solution.

TABLE 2

Results of ESCA Analysis of PEGM Coated Glass Microparticles: Elemental Percentages Excluding Hydrogen

| Sample | C | O | Na | N | Si | Ba | Ti | Cl | B | Ca | Sr |
|---|---|---|---|---|---|---|---|---|---|---|---|
| PEGM Coated Glass Microparticles | 69 | 30 | ND[1] | ND | 0.6 | ND | DL[2] | ND | ND | ND | ND |
| Bare Glass Microparticles, | 21 | 53 | 0.2 | | 2.8 | 3.1 | 13 | 0.7 | 4.8 | 1.3 | 0.1 |

[1]ND means Not Detected
[2]DL means at the Detection Limit

B. Activation of PEGM Coated Microparticles and Coupling of Fluorescent Dye Probe thereto:

The PEGM coating can be further activated and conjugated to biological ligands using many different chemical methods, including the use of trichloro-s-triazine (Abuchowski, A. et al., *J. Bio. Chem.* 252, 3578–3581, and 3582–3586 (1977)), N,N'-carbonyldiimidazole (Bartling, G. J. et al. *Nature* (London), 243, 342–344 (1973)), and organic sulfonyl chloride such as tosyl chloride and tresyl chloride (Nilsson, K. and Mosbach, K. *Methods in Enzymology*, 1984, 104, pp 56–69). The process is typically done by reacting with the hydroxyl groups in the PEGM chains to create a reactive electrophilic intermediate that is capable of easily coupling to nucleophilic residues such as the amine or sulfhydryl groups in the protein molecules. Tresyl chloride was chosen because it offers high yields of coupled product at neutral pH, and mild conditions, and results in good stability.

The protocol used for activation of the PEGM coated microparticles and ligand coupling, using Alexa Fluor® 488 as the ligand example, was as follows. Dry PEGM coated glass microparticles (2 g), prepared as described above, were washed successively with 50 mL of each of the following: 30:70 and 70:30 of acetone: water (v/v), twice with acetone, and three times with dried acetone (dried with 4 Å molecular sieves overnight at a ratio of 25 g of the molecular sieves per liter of acetone). The PEGM coated glass microparticles were then transferred to a dried flask containing 7 mL of dry acetone and 350 µL of dry pyridine that was dried with 4 Å molecular sieves overnight before use. This mixture was stirred using a magnetic stirrer and placed in an ice/water bath. Tresyl chloride (360 µL) (Aldrich, product number 324787, batch number 01910AB) was added dropwise to the suspension over a period of about 10 min. Then, the reaction was allowed to continue in the ice/water bath for 1.5 h with stirring. At the end of the reaction, the microparticles were isolated by filtration and washed twice with 50 mL of each of the following: acetone; 30%, 50%, and 70% (v/v) of 5 mM HCl in acetone; and finally, 1 mM HCl. The activated microparticles were briefly dried in vacuum at room temperature and stored in a desiccator at 4° C.

The Alexa Fluor® 488 dye was coupled to the tresylated microparticles in 0.2 M sodium phosphate buffer, pH 8.2 as the coupling buffer using the following procedure. One milligram of Alexa Fluro® 488 hydrazide, sodium salt (Molecular Probes, Inc. Eugene, Oreg.; product number A-10436, lot 34C1) was dissolved in 2 mL of the coupling buffer. The tresylated microparticles (0.5 g) were washed briefly with the cold coupling buffer using the microconcentrator, as described above, and then were transferred to the Alexa Fluro® 488 solution. The coupling reaction was allowed to proceed with stirring on for 36 h at 4° C. The supernatant was then removed with a pipette and the reaction was quenched with 0.1 M mercaptoethanol in 0.1 M Tris-HCl, pH 8.5 buffer for 5 h. The microparticles were washed in sequence with 0.2 M sodium acetate-0.5M NaCl, pH 3.5 buffer; 0.5 M NaCl solution; distilled water; and 0.2 M, pH 7.5 PBS buffer. The microparticles were dried briefly at room temperature and stored in the refrigerator for future use.

The Alexa Fluor® 488 microparticles were tested with a direct ELISA to verify the success of coupling and to determine the probe density using the same procedure described in Example 5, step A. The anti-Alexa Fluor® 488 rabbit IgG peroxidase conjugate was prepared using the EZ-Link™ Plus Activated Peroxidase Kit (Pierce, Cat. No. 31489) and the anti-Alexa Fluor® 488 rabbit IgG from Molecular Probes (Cat No. A-11094). Very low absorbance was observed from the control microparticle samples, and the saturated absorbance obtained at high enzyme conjugate concentration for Alexa Fluor® 488 microparticles was used to calculate the Alexa Fluor® 488 surface density. The calculated surface density was 0.42 pmol per gram of microparticles. No effort was made to determine the enzyme activity-reducing factor to correct the Alexa Fluor® 488 surface density in this case.

C. Antibody Binding Detection in a Serum Background:

Anti-Alexa Fluor® 488 rabbit IgG fraction was obtained from Molecular Probes, Inc. (product number A-11094, lot number 7581), and was diluted to a concentration of 50 µg/mL with 10 mg/mL rabbit serum to test its binding to the Alexa Fluor® 488 dye coupled microparticles, prepared as described in step B. The rabbit serum (Sigma Chemical Co. product R9133, lot 041K9089) containing 50 mg/mL proteins was diluted with pH 7.2, 25 mM (10 mM sodium phosphate, 15 mM NaCl) PBS buffer to give a 10 mg/mL protein concentration. Before the binding detection with resonant light scattering, about 50 mg of the Alexa Fluor® 488 dye coupled microparticles was incubated in 1.5 mL of the 10 mg/mL rabbit serum solution for 1 h to further block nonspecific binding sites. The Alexa Fluor® 488 dye coupled microparticles were washed twice with PBS buffer and then were dispersed in the PBS buffer. These dispersed Alexa Fluor® 488 dye coupled microparticles were loaded into the sample cell for binding experiments. For in situ binding detection with resonant light scattering, the same procedure as described in Example 3 was used. Before rabbit IgG binding, resonant light scattering spectra were taken on Alexa Fluor® 488 dye coupled microparticles in pH 7.2, 25 mM (10 mM sodium phosphate, 15 mM NaCl) PBS buffer as the reference spectra. Then, 12 mL of a solution containing 10 mg/mL rabbit serum proteins in the same pH 7.2 PBS buffer was passed through the sample cell with circulation at a flow rate of about 1.5 mL/min for 0.5 h, in order to test for nonspecific binding. The sample cell was then flushed with pure pH 7.2 PBS, so resonant light scattering was measured in the same medium in which the reference spectra were taken. Afterwards, 10 mL of a solution containing 50 μg/mL of the anti-Alexa Fluor® 488 rabbit IgG in 10 mg/mL rabbit serum was passed through the sample cell with circulation at a flow rate of about 1.5 mL/min for 0.5 h. At the end of the incubation, the sample cell was flushed with pure pH 7.2 PBS, and resonant light scattering was measured in the same medium in which the reference spectra were taken.

Autocorrelation analysis was used to obtain the resonance wavelength shift for the serum background testing step and the anti-Alexa Fluor® 488 rabbit IgG binding step. The average shifts for the background test step and for the rabbit IgG binding step were 0.004±0.004 nm and 0.037±0.006 nm, respectively. These values are averages for 3 different microparticles and 9 different before-and-after laser scan run pairs. The wavelength shift results showed almost no shift in the background test step, implying good resistance against nonspecific binding. The wavelength shift in the rabbit IgG binding step was a bit smaller than that observed with the Protein G'-mouse IgG binding (Example 5), possibly because of a lower binding strength in the different system.

Example 8

Multiple Protein Binding Assay in an *E. coli* Cellular Extract Background Using Resonant Light Scattering Detection The purpose of this Example was to demonstrate multiplex assays using resonant light scattering on a mixture of two kinds of probe microparticles in an *E. coli* cellular extract background. A mixture of Alexa Fluor® 488 and mouse IgG microparticles were used in the multiplex assay and the binding of the particles to their corresponding antibody was detected using resonant light scattering.

A. Preparation of Alexa Fluor® 488 Microparticles and Mouse IgG Microparticles:

Two kinds of probe microparticles with the same PEGM coating but different capture ligands, namely Alexa Fluro®D 488 and mouse IgG, were prepared according to the procedure described in Example 7 (step A and step B). The PEGM coating was used to prevent nonspecific binding in a high protein concentration background. Procedures used for PEGM coating, tresyl chloride activation and the coupling of Alexa Fluro® 488 to the activated microparticles are described in Example 7. Mouse IgG was coupled to the tresyl chloride activated microparticles in the same way. PBS buffer (0.2 M, pH 8.2) was used as the coupling buffer. Ten milligrams of mouse IgG (Sigma Chemical Co. product I 5381) was dissolved in the coupling buffer to make a 1 mg/mL solution. The tresyl chloride activated microparticles (0.5 g) were briefly washed with the cold coupling buffer and transferred to 5 mL of the mouse IgG solution. The microparticle suspension was stirred for about 36 h at 4° C. The supernatant was then removed with a pipette, and the reaction was quenched with 5 mL of a solution consisting of 0.1 M mercaptoethanol (Aldrich Chemical Company, Inc. product M3701) in 0.1 M Tris-HCl, pH 8.5 buffer for 5 h. The microparticles were then washed successively with 0.2 M sodium acetate-0.5 M NaCl, pH 3.5 buffer; 0.5 M NaCl solution; distilled water; and then 0.2M, pH 7.5 PBS buffer. The microparticles were dried briefly at room temperature and stored in the refrigerator before use.

B. Preparation of *E. coli* Cellular Extract:

*E. coli* cellular extract was used as a competing protein background for the multiplex assay demonstration. *E. coli* bacterial cells (0.5 mL, Invitrogen Co. Carlsbad, Calif., DH10B™ cells, Catalog number 18290-015, Lot: 1172474) were inoculated in 250 mL Miller's LB broth (Mediatech Inc. Herndon, Va., Catalog number 46-050CM Lot: 46050009), and the culture was incubated overnight in a shaking incubator at 37° C. and 225 rpm. The cells were harvested using centrifugation at 5,000×g for 15 min. The amount of cell pellet was about 1.0 g. The supernatant was removed from the cell pellet, 15 mL of CelLytic™ B Bacterial Cell Lysis Reagent (Sigma Chemical Co. product B3553, Lot:052k9319) was added, and the suspension was mixed well to completely resuspend the cells. The cell extract suspension was incubated with shaking at room temperature for 15 min to fully extract the cells, and was centrifuged at 25,000×g for 20 min to pellet the insoluble material. The supernatant that contains the soluble proteins was carefully removed. About 90–95% of soluble protein was found in this fraction. The total protein concentration was determined to be 4.4 mg/mL using the Bradford method (Bradford, supra).

C. Antibody Binding Detection in the Background of *E. coli* Cellular Extract:

In order to demonstrate a multiplex assay using resonant light scattering, Alexa Fluor® 488 microparticles and mouse IgG microparticles of equal weight, prepared in step A, were mixed. This microparticle mixture was incubated in 1.5 mL of 1% BSA (Sigma, product B4287) in 10 mM, pH 7.4 PBS buffer for 3 h at room temperature to further block nonspecific binding sites. This incubation was followed by two washes with 1.5 mL of PBS buffer and resuspension in PBS buffer. Then, the suspended microparticles were loaded into the sample cell for binding experiments. To determine which microparticles were labeled with Alexa Fluor® 488, a 488 nm Ar ion laser (25 mW, Omnichrome Corp., Carlsbad, Calif.) was used to excite the fluorescent dye and an excitation cutoff high-pass filter was inserted in the output optical path to examine the fluorescence emission. A field containing both fluorescing microparticles and non-fluorescing microparticles was selected for resonant light scattering experiments. The fluorescing microparticles were Alexa Fluor® 488 labeled microparticles and the non-fluorescing microparticles were assumed to be mouse IgG-labeled microparticles. The fluorescence image and the plain image of this view are shown for comparison in FIG. 17. It should be noted that fluorescence was used in this study to identify the microparticles because the automated pattern recognition software, required to enable resonant light scattering identification, was not available. The microparticles remained in place during the experiments, so their location was used to track them. However, with the required software it would be possible to use resonant light scattering for particle identification and tracking, as demonstrated in Examples 1 and 2, and for the detection of binding.

For in situ binding detection with resonant light scattering, the same procedure as described in Example 3 was used. Resonant light scattering spectra were first taken on the selected microparticles in pH 7.2, 25 mM (10 mM sodium phosphate, 15 mM NaCl) PBS buffer as the reference spectra. Then, three binding step measurements were carried out to check whether there was nonspecific binding from competing background proteins and to test whether there was cross-reactivity between the Alexa Fluor® 488 probe and rabbit anti-mouse IgG, and between the mouse IgG probe and anti Alexa Fluor® 488 rabbit IgG. In step 1, 12 mL of a solution consisting of 2.2 mg/mL E. coli cellular extract proteins in the same PBS buffer was passed through the sample cell with circulation at a flow rate of about 1.5 mL/min for 0.5 h, as a test of the background. In step 2, anti-Alexa 488 rabbit IgG (Molecular Probes, Inc. product number A-11094, lot number 7581) was added to the same cellular extract solution used in step 1 to give a 50 µg/mL working concentration, and the solution was passed through the sample cell with circulation at a flow rate of about 1.5 mL/min for 0.5 h to test the binding of the anti-Alexa 488 rabbit IgG to the microparticles. In step 3, rabbit anti-mouse IgG (H+L) (unconjugated, Pierce, product 31188, lot EE761527) was added in the solution used in step 2 to give a 50 µg/mL working concentration, and the solution was passed through the sample cell with circulation at a flow rate of about 1.5 mL/min for 0.5 h to test the binding of anti-mouse IgG to the microparticles. There was a PBS buffer wash after each step, and spectra were taken after each washing step.

Autocorrelation analysis was used to obtain the resonance wavelength shifts for both Alexa Fluor® 488 microparticles and mouse IgG microparticles after the cellular extract background testing step, the anti-Alexa Fluor® 488 rabbit IgG binding step and the rabbit anti-mouse IgG binding step. The results are summarized in the Table 3 (all shifts are referenced to the spectra taken at the beginning). The values given in the table are the averages over 3 different microparticles and 9 different before-and-after laser scan run pairs.

Example 9

DNA Probe-coupled Microparticles for Detection of a Specific DNA Analyte Using Resonant Light Scattering The purpose of this Example was to demonstrate the use of resonant light scattering to specifically detect nucleic acid analytes using microparticles linked to nucleic acid probes. Fluorescent-labeled analytes were used as assay controls to verify specific binding of the analyte to the DNA probe-microparticles.

A. Microparticle Preparations:

The high refractive index glass microparticles (Cat. No. GL-0175, Mo-Sci Corp., Rolla, Mo.) were prepared as described in Example 3. The cleaned glass microparticles were silanized to produce surface reactive amine groups, as described in Example 3, for coupling to the nucleic acid oligomer probe. The amine-derivatized glass microparticles were further derivatized with maleimide groups by coupling sulfosuccinimidyl (NHS) 4-[N-maleimidomethyl] cyclohexane-1-carboxylate (sulfo-SMCC) to the amine groups. An aliquot of 400 mg of amine-derivatized glass microparticles was added to a reaction mixture consisting of 130 mM carbonate/bicarbonate buffer, pH 9.6, 13.3 mg/mL sulfo-SMCC (Pierce Biotechnology Inc., Rockford, Ill.; product number 22322), and 33.3% dimethylformamide (DMF). This mixture was placed into a 1.5 mL round-bottom tube that was rotated at room temperature for 1 h to allow the surface amines to react with the NHS group on the sulfo-SMCC. The maleimide-derivatized microparticles were washed at room temperature with 500 µL of 100 mM sodium phosphate, 150 mM NaCl buffer, pH 7.2 (PBS). The buffer was removed by centrifuging the suspended microparticles using a microconcentrator (Microcon® 100, Amicon, W. R. Grace Co., Beverley, Mass.) in a Sorvall Microspin microcentrifuge (Kendro Laboratory Products, Newtown, Conn.) at 12,000 rpm and room temperature. The microparticles were washed twice with the PBS buffer using the microconcentrator. The maleimide-derivatized microparticle pellet was transferred to a second 1.5 mL round-bottom reaction tube and stored at 4° C.

A second set of microparticles was produced with a nonspecific-binding resistant layer using a PEGM coating as

TABLE 3

Resonance Wavelength Shifts in the Resonant light Scattering Spectra of Alexa Fluor ® 488 Microparticles and Mouse IgG Microparticles in Three-Step Binding Experiments

| Microparticles | Resonance wavelength shift (nm), step 1: 2.2 mg/mL protein cell extract background | Resonance wavelength shift (nm), step 2: 50 µg/mL anti-Alexa rabbit IgG in step 1 background | Resonance wavelength shift (nm), step 3: 50 ug/mL anti-mouse rabbit IgG in step 2 background |
|---|---|---|---|
| Alexa Fluor ® 488 microparticles | 0.004 ± 0.004 | 0.034 ± 0.006 | 0.030 ± 0.005 |
| Mouse IgG microparticles | −0.005 ± 0.006 | −0.004 ± 0.004 | 0.056 ± 0.007 |

As can be seen from the data in Table 3, the average shifts in the background test step for both types of microparticles were almost zero, indicating no nonspecific binding of background proteins. For Alexa Fluor® 488 microparticles, there was a corresponding resonance wavelength shift of 0.034±0.006 nm upon anti-Alexa Fluor® 488 rabbit IgG binding in the second step, and that shift remained almost unchanged in the third step. For mouse IgG microparticles, there was almost zero shift in the second step and 0.056±0.007 nm shift in the third step. These results clearly indicate that there was no cross-reactivity between the two antibodies and two ligands, but exclusive binding of anti-Alexa Fluor® 488 rabbit IgG to Alexa Fluor® 488 probes and exclusive binding of anti-mouse IgG to mouse IgG probes. These results demonstrate the use of resonant light scattering for detection in multiplex assays.

described in Example 7. The PEGM surface was activated with tresyl chloride for conjugation to thio-activated oligonucleotides, as described in Example 7.

B. The Oligonucleotide Probes and Preparation of the Oligonucleotide Probe-coupled Microparticles:

The oligonucleotide probe sequences were designed to specifically detect the synthetic foot and mouth disease (FMD) target nucleic acid sequence, given as SEQ ID NO:1, disclosed by Ebersole et al. in copending U.S. patent application Ser. No. 60/434,974, which is incorporated herein by reference. The FMD oligonucleotide probe specific sequence (JBP) used in the assay was 5' TCAACCAGATGCAGGAGGACATGTCMCAAAACACGGACCCGACT TAA 3', given as SEQ ID NO:2. This sequence was modified at the 5' and 3' ends as described below, to obtain the modified FMD probe (JBP S2SP3B): $C_6$—S—S(SP)$_2$-TCMCCAGATGCAGGAGGACATGTCAA-CAAAACACGGACC CGACTTAA-B 3', given as SEQ ID NO:3. The "B" is a 3' biotin group added to the sequences during DNA synthesis as a 3' coupling reagent attached to control-pore glass solid supports used in, β-cyanoethyl phosphoramidite synthesis chemistry (Biotin CPG, Glen Research, Sterling, Va.). "Sp" refers to the 18-atom spacer arm phosphoramidite, 18-O-dimethoxytritylhexaethyleneglycol, 1-[(2-cyanoethyl)-(N,N-diisopropyl)]-phosphoramidite (Glen Research, Sterling, Va.). Two of these spacer moieties were coupled to the 5' end between the probe sequence and the probe crosslinking moiety to serve as molecular spacers using β-cyanoethyl chemistry. The "$C_6$—S—S" (1-O-dimethoxytritylhexyl-disulfide, 1-[(2-cyanoethyl)-(N,N-diisopropyl)]-phosphoramidite, Glen Research, Sterling, Va.) is a disulfide moiety used as a crosslinking thiol-modifier.

To prepare the modified JBP S2SP3B probe for coupling to the maleimide-derivatized microparticles, the disulfide modifier was cleaved from 70 nmol of the probe using 400 μL of 100 mM dithiothreitol (DTT) in 0.2 M Tris buffer, pH 8.3, creating a thiol-activated probe. The thiol-activated probe was purified from the C6-thio group and DTT using ethanol precipitation by adding 100 μL of 3 M sodium acetate, pH 5.4 and 1000 μL of 100% ethanol, and mixing well. The DNA precipitate was centrifuged into a pellet by centrifugation in a Sorvall Microspin microcentrifuge at 12,000 rpm and room temperature. The oligonucleotide pellet was washed twice with 70% ethanol and dissolved in 200 μL of double-distilled water.

The maleimide-derivatized microparticles (400 μg), prepared as described in Part A, were transferred to a 1.5 mL round-bottom reaction tube for coupling to the thiol-activated JBP S2SP3B probe. The thiol-activated JBP S2SP3B probe (70 nmol), prepared as described above, was added to the tube. Then, 500 μL of PBS, pH 7.4 was added and the tube was rotated, in order to mix and suspend the microparticles, at room temperature for 2 h to allow the surface maleimide groups to react with the thiol-activated probe. The DNA probe-coupled microparticles were washed at room temperature with 500 μL of PBS. The PBS was removed by centrifuging the suspended microparticles using a Microcon® 100 microconcentrator in a Sorvall Microspin microcentrifuge at 12,000 rpm and room temperature. The microparticles were washed twice with PBS buffer and then the JBP S2SP3B probe-coupled microparticle pellet was transferred to a 1.5 mL micro-tube and stored at 4° C.

An additional probe, N-JBC (5' $NH_2$-TTAAGTCGGGTCCGTGTTTTGTTGACAT-GTCCTCCTGCATCT GGTTGA-B 3'), given as SEQ ID NO:4, was synthesized by MWG Biotech, Inc. (High Point, N.C.). This probe contained a 5' amine group and a 3' biotin group. The probe was coupled to the tresyl activated PEGM microparticles through the 5' amine. Specifically, 100 μL of 100 μM N-JBC DNA was incubated with 40 mg of tresylated PEGM microparticles in 0.2 M PBS buffer, pH 8.2 for 3 days at room temperature. The N-JBC probe-coupled microparticles were then washed two times in 0.1 M PBS, pH 7.2 using a Microcon® 100 microconcentrator. The microparticle pellet was transferred to a 1.5 mL micro-tube. The N-JBC probe-coupled microparticles were designated JBC-PEGM and were stored at 4° C.

C. Detection of Hybridization Capture of a FMD Oligonucleotide Target DNA onto the DNA Probe-coupled Microparticles Using Fluorescence:

A FMD specific DNA oligonucleotide target labeled with a 3' fluorescein tag (JBC-F), specifically, 5' TTAAGTCGGGTCCGTGTTTTGTTGACAT-GTCCTCCTGCATCTGGTT GA-F 3', given as SEQ ID NO:5, that is complementary to the JBP probe sequences (SEQ ID NO:2 and SEQ ID NO:3), was used to test the functionality of the microparticle probe. A second oligonucleotide was designed with no sequence complementary to the JBP S2SP3B probe to act as a fluorescein-labeled, nonspecific target control (Lac2-F), 5' TGAATTTGATTGC-GAGTGAGATATTTATGCCAGCCAGCCAGACGCA GAC-F 3', given as SEQ ID NO:6.

The JBP S2SP3B probe-modified microparticles (2 μL) were mixed with 2 μL of 10 μM JBC-F (SEQ ID NO:5) or Lac2-F (SEQ ID NO:6) in 20 μL of 0.3 M NaCl, PBS buffer and were hybridized for 1 h at room temperature on a rolling mixer. The tubes were centrifuged briefly to pellet the microparticles and the supernatant was removed. The assay microparticles were then washed three times with 200 μL aliquots of 0.3 M NaCl, PBS buffer with brief vortexing and centrifugation. After the final wash, the microparticles were suspended in 50 μL of the 0.3 M NaCl, PBS buffer. One microliter of suspended microparticles from each sample was mounted onto slides in 2 μL of VECTASHIELD® Mounting Medium (Vector Laboratories, Inc., Burlingame, Calif.). Samples were observed under a fluorescence microscope (Zeiss Axioskop 40, Carl Zeiss Microimaging, Inc., Thorwood, N.Y.)) fitted with a Spot RTKE CCD camera (Diagnostic Instruments, Inc. Sterling Heights, Mich.).

The resulting fluorescence micrographs demonstrated that the JBC-F DNA target was captured onto the JBP S2SP3B-coupled microparticles and that the Lac2-F nonspecific control target was not captured. The background autofluorescence of the JBP S2SP3B-coupled microparticles without a target was also tested. Autofluorescence was small compared to the fluorescence attributed to the binding of the fluorescein-labeled JBC-F target. These results indicate that the JBP S2SP3B-coupled microparticles were specific for the JBC-F target sequence.

D. Detection of Hybridization Capture of a FMD Oligonucleotide Target DNA onto DNA Probe-coupled Microparticles Using Resonant Light Scattering:

Next, resonant light scattering was used to detect the binding of the DNA target to the DNA probe-coupled microparticles. The procedure used was similar to that described in Examples 2 and 3. The JBP S2SP3B probe-coupled microparticles, prepared as described in Parts A and B, were dispersed in 0.3 M NaCl, 0.1 M sodium phosphate buffer, pH 7.4 (0.3 M NaCl, PBS buffer). A 2 μL aliquot of this suspension was placed in an optical flow cell, similar to the one described in Example 3 and shown in FIG. 6. A field of view was selected that contained a small number (2–6) of microparticles. A "prescan" measurement was taken to determine the assay background spectra. As described in Example 3, the diode laser light source was then scanned between 770 and 780 nm in 50 s, and 1500 images were captured and stored as a pixel stack file and analyzed by software installed in the system's personal computer. Several microparticles in the field of view were selected for subsequent detailed spectral analysis, similar to that described in Example 3 and shown in FIG. 8. By analyzing the full set of wavelength-dependent scattered light images as described in Example 2, a scattered light spectrum from this particle was obtained. The scattered light spectra acquired from the JBP S2SP3B probe-coupled microparticles were similar to those described in Example 2 and shown in FIG. 9.

The resonant light scattering assay was performed as described below and spectral measurements were taken after each incubation/wash step. Approximately 5 mL of the control Lac2-F target DNA, at a concentration of 1 µM in 0.3 M NaCl, PBS buffer, was flowed continuously across the JBP S2SP3B probe-coupled microparticles at a flow rate of about 1 mL/min, and was collected into waste. The effluent tube was then transferred back into the original sample and the remaining 5 mL of target DNA was recycled in a closed loop system for 1 h. The JBP S2SP3B probe-coupled microparticles were then washed with 10 mL of 0.3 M NaCl, PBS buffer, and the effluent was discarded. A resonant light scattering spectral scan was taken of the JBP S2SP3B probe-coupled microparticles after the wash. Approximately 5 mL of a 1 µM sample of the probe specific JBC-F oligonucleotide target in 0.3 M NaCl, PBS buffer was then added to the flow cell and flowed continuously across the microparticles for 1 h. The microparticles were then washed with 10 mL of 0.3 M NaCl, PBS buffer. Again, a resonant light scattering spectral scan was taken of the JBP S2SP3B probe-coupled microparticles after the wash.

The results are shown Table 4. A negative shift in the resonant light scattering pattern was observed upon nonspecific binding of the Lac2-F target oligonucleotide to the microparticles. A significant negative shift in the resonant light scattering pattern was observed upon binding of the specific JBC-F target oligonucleotide to the JBP S2SP3B probe-coupled microparticles. These results show that the binding of oligonucleotide probe-coupled microparticles to non-specific or specific oligonucleotide targets results in a negative resonance wavelength shift in the resonant light scattering spectra of the particles. These results also demonstrate the use of resonant light scattering to detect binding of oligonucleotide DNA targets to specific DNA oligonucleotide probes coupled to microparticles.

TABLE 4

Resonance Wavelength Shifts in the Resonant Light Scattering Spectra of Oligonucleotide DNA Probe-Coupled Microparticles Upon Binding to Oligonucleotide Targets

| Microparticles | Resonance wavelength shift (nm), step 1-background: 0.3 M NaCl, PBS buffer, pH 7.4 | Resonance wavelength shift (nm), step 2-nonspecific analyte target: Lac2-F oligonucleotide non-specifically bound | Resonance wavelength shift (nm), step 3-specific analyte target specifically bound |
| --- | --- | --- | --- |
| JBP S2SP3B probe-coupled microparticles | 0.0 ± 0.004 | −0.01426 ± 0.007 | −0.02634 ± 0.009 (JBC-F target) |
| JBC-PEGM microparticles | 0.0 ± 0.0007 | −0.00136 ± 0.0006 | −0.01910 ± 0.0011 (JBP-F target) |

E. Detection of Hybridization Capture of a FMD Oligonucleotide Target DNA onto the DNA Probe-coupled, PEGM-Coated Microparticles Using Fluorescence:

An FMD specific DNA oligonucleotide target labeled with a 3' fluorescein tag (JBP-F) (5' TCAACCAGATGCAG-GAGGACATGTCAACAAAACACGGACCCGACT TAA-F 3'), given as SEQ ID NO:7, was used to test the functionality of the microparticle probe. The fluorescein-labeled, nonspecific target (Lac2-F), SEQ ID NO:6, was used as a control.

Two microliters of the N-JBC probe-coupled, PEGM-coated microparticles (JBC-PEGM) were mixed with 2 µL of 10 µM JBP-F or Lac2-F (SEQ ID NO:6) in 20 µL of 0.3 M NaCl, PBS buffer and were hybridized for 1 h at room temperature on a rolling mixer. The microparticles were pelleted briefly by centrifugation and the supernatant was removed. The microparticles were then washed three times with 200 µL of 0.3 M NaCl, PBS buffer with brief vortexing and centrifugation. The microparticles were then suspended in 50 µL of the 0.3 M NaCl, PBS buffer. One microliter of suspended microparticles from each sample was mounted onto slides and observed under a fluorescence microscope as described above.

The resulting fluorescence micrographs demonstrated that the specific JBP-F DNA target was captured onto the microparticles and that the Lac2-F nonspecific control target was not. These results indicate that the N-JBC probe-coupled, PEGM-coated microparticles were specific for the JBP-F target DNA.

F. Detection of Hybridization Capture of a FMD Oligonucleotide Target DNA onto the DNA Probe-coupled, PEGM-coated Microparticles Using Resonant Light Scattering:

Resonant light scattering was used to detect the binding of target DNA to the N-JBC probe-coupled, PEGM-coated microparticles. The procedure used was similar to that described in Examples 2 and 3. The JBC-PEGM microparticles were dispersed in 0.3 M NaCl, 0.1 M sodium phosphate buffer, pH 7.4 (0.3 M NaCl, PBS buffer). A 2 µL aliquot of this suspension was placed in the optical flow cell. A "prescan" measurement was taken to determine the assay background spectra and several microparticles in the field of view were selected for subsequent detailed spectral analysis, similar to that described above and in Example 3 and shown in FIG. 8. The scattered light spectra acquired from the JBC-PEGM microparticles were similar to those described in Example 2 and shown in FIG. 9.

The resonant light scattering assay was performed as described below and spectral measurements were taken after each incubation/wash step. Approximately 5 mL of the control Lac2-F target DNA, at a concentration of 1 µM in 0.3 M NaCl, PBS buffer, was flowed continuously across the JBC-PEGM microparticles at a flow rate of about 1 mL/min, and was collected into waste. The effluent tube was then transferred back into the original sample and the remaining 5 mL of target DNA was recycled in a closed loop system for 1 h. The microparticles were then washed with 10 mL of 0.3 M NaCl, PBS buffer, and the effluent was discarded. A resonant light scattering spectral scan was taken of the microparticles after the wash.

The previous microparticles were removed from the cell and were replaced with fresh JBC-PEGM microparticles. Again, the assay background spectra were determined by a "prescan" measurement. Approximately 5 mL of a 1 µM sample of the probe specific JBP-F oligonucleotide target in 0.3 M NaCl, PBS buffer was then added to the flow cell and flowed continuously across the microparticles. The effluent tube was then transferred back into the original sample and the remaining 5 mL of target DNA was recycled in a closed loop system for 1 h. The microparticles were then washed with 10 mL of 0.3 M NaCl, PBS buffer. Again, a resonant light scattering spectral scan was taken of the microparticles after the wash.

The results are shown Table 4. An insignificant negative shift in the resonant light scattering pattern was observed upon non-specific binding of the Lac2-F target oligonucleotide to the JBC-PEGM microparticles. A significant negative shift in the resonant light scattering pattern was observed for the specific JBP-F target oligonucleotide binding to the JBC-PEGM microparticles. These results show that the DNA probe-coupled, PEGM-coated microparticles behave similarly to the uncoated, DNA probe-coupled microparticles as described above, but they have less background resonance for the nonspecific target (Table 4).

Example 10

Detection of Hybridization Capture of a PCR Product Target onto DNA Probe-coupled Microparticles Using Resonant Light Scattering The purpose of this Example was to demonstrate the use of resonant light scattering for detecting PCR product DNA analytes using microparticles linked to nucleic acid probes.

A. Microparticle Preparation and Oligonucleotide Probe Coupling:

The JBP S2SP3B probe-coupled microparticles were prepared as described in Example 9.

B. Preparation of PCR Targets:

A 206 bp amplified FMD DNA fragment (JB), given as SEQ ID NO:8, and a 511 bp amplified LacIQ fragment (Lac2-511), given as SEQ ID NO:9, were produced using standard PCR protocols as follows. The 206 bp PCR fragment was produced as an asymmetric PCR product from the 516 bp synthetic FMD target (SEQ ID NO:1) insert cloned into pCR4-TOPO plasmid vector (Invitrogen, Carlsbad, Calif.) using 2 pmol of the forward primer, P2FWD, 5' GAGTCCMCCCTGGGCCCTTCTTCTTC 3', given as SEQ ID NO:10, and 20 pmol of the reverse primer, P33-4, 5' ATGAGCTTGTACCAGGGTTTGGC 3', given as SEQ ID NO:11. Five microliters of the product was then reamplified in the presence of 5 pmol of P2FWD and 50 pmol of P33-4.

The 511 bp PCR fragment was produced as an asymmetric PCR product from E. coli LacIQ insert cloned into pCR4-TOPO plasmid vector using 2 pmol of the forward primer, Lac1pst, 5' ATACTGCAGAACGCGT-CAGTGGGCTGATCA 3', given as SEQ ID NO:12, and 20 pmol of the reverse primer, Lac4eco, 5' ACAGAATTCCAT-GAGCTGTCTTCGGTATCGTCGTA 3', given as SEQ ID NO:13. Five microliters of the product was then reamplified in the presence of 5 pmol of Lac1pst and 50 pmol of Lac4eco. The asymmetric PCR reaction mixes contained 200 µM dNTPs and 2.5 units of Pfu Turbo DNA polymerase (Stratagene, La Jolla, Calif.) in a final volume of 50 µL PCR buffer (10×: 100 mM KCl, 100 mM $(NH_4)_2SO_4$, 200 mM Tris-HCl pH 8.75, 20 mM $MgSO_4$, 1% Triton X-100, 1 mg/mL BSA). Amplifications were performed in a Gene-Amp®9600 thermal cycler (Perkin-Elmer Corp., Norwalk, Conn.). The samples were denatured for 2 min at 94° C., followed by 35 cycles with denaturation at 94° C. for 20 s, annealing at 55° C. for 20 s, and extension at 72° C. for 1 min. After completion of the amplification cycles, the final chain extension was at 72° C. for 5 min. Samples were then ramped to 4° C. and maintained at that temperature until sample analysis.

Amplified DNA products were analyzed for their yield of asymmetric amplified product by agarose gel electrophoresis. PCR products were separated on 1.5% SeaKem® LE agarose (FMC BioProducts, Rockland, Me.) in 0.5× TBE buffer (Digene Diagnostics, Inc., Silver Spring, Md.) containing 0.5 µg/mL of ethidium bromide. An aliquot of 4 µL from the amplified samples was mixed with 1 µL of gel loading buffer and loaded onto the agarose gel. Gel electrophoresis was carried out by applying 100 V (or 5.9 V/cm) to the gel for 1 h. The ethidium bromide-stained DNA bands were visualized and digitally recorded using an Eagle Eye II Still Video System (Stratagene, La Jolla, Calif.).

Detection of Hybridization Capture of the FMD PCR Product Target DNA onto DNA Probe-coupled Microparticles Using Resonant Light Scattering:

Resonant light scattering detection was performed as described in Examples 3 and 9, and shown in FIG. 9. Resonant light scattering measurements were taken after each incubation/wash step. As described in Example 9, a small aliquot, 2 to 3 µL, of the JBP S2SP3B probe-coupled microparticle suspension was placed in an optical cell. A field of view similar to that shown in FIG. 8 was selected that contained a small number (2 to 6) of microparticles. A prescan measurement was taken to record the assay background. Approximately 5.0 mL of the nonspecific control PCR target fragment, Lac2-511 DNA (5 pmol of the PCR product in 5 mL of 0.3 M NaCl, PBS buffer) was flowed continuously across the microparticles at a flow rate of about 1 mL/min, and was recycled in a closed loop system for 1 h. The JBP S2SP3B probe-coupled microparticles were then washed with 10 mL of 0.3 M NaCl, PBS buffer, and the effluent was discarded. A resonant light scattering spectral scan was taken of the JBP S2SP3B probe-coupled microparticles after the wash. Approximately 5.0 mL of the specific JB PCR target fragment (5 pmol in 5 mL of 0.3 M NaCl, PBS buffer) was flowed continuously across the microparticles for 1 h followed by a 10 mL wash with 0.3 M NaCl, PBS buffer. Again, a resonant light scattering spectral scan was taken of the JBP S2SP3B probe-coupled microparticles after the wash.

The results are shown in Table 5. A negative shift in the resonant light scattering pattern was observed upon non-specific binding of the Lac2-F PCR fragment to the microparticles. When a specific PCR target, the JB PCR product, was used as the analyte, a significant negative shift in the resonant light scattering pattern was observed upon binding to the JBP S2SP3B probe-coupled microparticles. These results show that oligonucleotide probe-coupled microparticles exhibit a negative resonance wavelength shift in their resonant light scattering spectra upon binding to PCR specific analytes. These results also demonstrate the use of resonant light scattering and DNA oligonucleotide probes coupled to microparticles to detect PCR produced DNA analytes.

TABLE 5

Resonance Wavelength Shifts in the Resonant Light Scattering Spectra of Oligonucleotide DNA Probe-Coupled Microparticles Upon Binding to PCR Produced DNA Analytes

| Microparticles | Resonance wavelength shift (nm), step 1- background: 0.3 M NaCl, PBS buffer, pH 7.4 | Resonance wavelength shift (nm), step 2- nonspecific analyte target: Lac2-511 PCR fragment non-specifically bound | Resonance wavelength shift (nm), step 3- specific analyte target: JB PCR fragment specifically bound |
| --- | --- | --- | --- |
| JBP S2SP3B probe-coupled microparticles | 0.0 ± 0.002 | −0.0026 ± 0.009 | −0.0200 ± 0.006 |

Example 11

Detection of DNA Binding onto PNA Probe-coupled Microparticles by Resonant Light Scattering The purpose of this Example was to demonstrate the use of resonant light scattering to detect binding of nucleic acid analytes to microparticles linked to peptide nucleic acid (PNA) probes. PNA is an analogue of DNA that has a pseudo-peptide backbone, rather than the sugar-phosphate backbone of nucleic acids (DNA and RNA). PNA mimics the behavior of DNA and binds complementary nucleic acid strands. The unique chemical, physical and biological properties of PNA have been exploited to produce powerful biomolecular tools, antisense and antigene agents, molecular probes and biosensors. The neutral peptide-like backbone provides stronger and more specific binding to the target nucleic acid that is independent of salt concentrations. Therefore, we wanted to assess the feasibility of hybridization capture of DNA analytes using PNA probe-coupled microparticles. Fluorescent-labeled oligonucleotide analytes were used as assay controls to verify specific binding of the DNA analyte to the PNA microparticles.

A. Microparticle Preparation

The high refractive index glass microparticles (Cat. No. GL-0175, Mo-Sci Corp., Rolla, Mo.) were prepared as described in Example 3. The cleaned glass microparticles were silanized to produce surface reactive amine groups for coupling to the PNA oligomer probe. The amine-derivatized glass microparticles were further derivatized with maleimide groups, as described in Example 9. The maleimide-derivatized microparticle pellet was transferred to a second 1.5 mL round-bottom reaction tube and stored at 4° C.

B. Coupling the PNA Oligomer Probe to the Microparticles:

The PNA probe base sequence was designed to specifically detect FMD sequences described in Examples 9 and 10 to demonstrate the use of PNA oligomers as resonant light scattering assay probes. The sequence chosen was 5' TCCGTGTTTTGTTGAC 3' (JBP2C), given as SEQ ID NO:14. The modified JBP2C PNA oligomer probe sequence used in this Example, 5' B-OO-TCCGTGTTTTGTTGAC-Cy 3' (JBP2BC), given as SEQ ID NO:15, was synthesized by Applied Biosystems (Foster City, Calif.). The JBP2BC PNA oligomer was modified with a biotin moiety (B) at the 5' end (N-terminal). The "OO" represents the linker between the PNA oligomer and the biotin moiety. A cysteine residue (Cy) amino acid moiety was used to modify the JBP2BC PNA oligomer at the 3' end (C-terminal). The free thiol group on the cysteine was used to couple the PNA oligomer to the maleimide-derivatized microparticles.

To couple the PNA oligomer probe to the microparticles, 20 µL of 100 µM JBP2BC PNA oligomer was added to 40 mg of maleimide-derivatized microparticles in pH 7.4 PBS. The reaction mixture was incubated at room temperature for 2 h on a rolling mixer. The unreacted JBP2BC PNA oligomer and PBS were removed by centrifuging the suspended microparticles using a Microcon®100 microconcentrator in a Sorvall Microspin microcentrifuge at 12,000 rpm and room temperature. The microparticles were washed twice with PBS. The JBP2BC PNA probe-coupled microparticle pellet was transferred to a 1.5 mL micro-tube and stored at 4° C.

C. Detection of Hybridization Capture of a FMD Oligonucleotide Target DNA onto the PNA Probe-coupled Microparticles Using Fluorescence:

A FMD specific DNA oligonucleotide target (JBP-F) labeled with a 3' fluorescein, 5' TCAACCAGATGCAG-GAGGACATGTCAACAAAACACGGACCCGACT TAA-F 3', given as SEQ ID NO:7, which is a complementary sequence to the JBP2BC PNA probe, was used to test the functionality of the PNA probe-coupled microparticles. The fluorescein-labeled Lac2-F oligonucleotide (SEQ ID NO:6), described in Example 9, was used as a nonspecific control, which had no sequence complementarity to the JBP2BC PNA probe.

The JBP2BC PNA probe-coupled microparticles (2 µL) were mixed with 2 µL of 10 µM JBP-F assay target or 10 µM of the Lac2-F control target in 20 µL of 0.3 M NaCl, PBS buffer and were hybridized for 1 h at room temperature on a rolling mixer. The microparticles were pelleted and washed three times with 200 µL portions of 0.3 M NaCl, PBS buffer, as described in Example 9. After the final wash, the microparticles were suspended in 50 µL of the 0.3 M NaCl, PBS buffer. The samples (1 µL) were mounted onto slides in 2 µL of VECTASHIELD® Mounting Medium (Vector Laboratories, Inc., Burlingame, Calif.). The samples were observed under a fluorescence microscope, as described in Example 9.

The fluorescence micrographs demonstrated that the specific JBP-F assay target was captured onto the PNA probe-coupled microparticles and that Lac2-F nonspecific control target was not captured. The background autofluorescence of the PNA probe-coupled microparticles without a target was also tested. Autofluorescence was small compared to the fluorescence attributed to the binding of the fluorescein-labeled JBP-F target. These results indicate that the JBP2BC PNA probe-coupled microparticles were specific for the respective target JBP-F sequence.

D. Resonant Light Scattering Detection Using PNA Probe-coupled Microparticles:

Resonant light scattering was used to detect the binding of the DNA target to the PNA probe-coupled microparticles. The procedure used was similar to that described in Examples 2, 3 and 9. The JBP2BC PNA probe-coupled microparticles, prepared as described in Parts A and B, were dispersed in 0.3 M NaCl, PBS buffer, pH 7.4 and a small aliquot (2 to 3 µL) of the resulting microparticle suspension was placed in an optical cell similar to the one described in Example 3 and shown in FIG. 6. A field of view similar to that shown in FIG. 8 and described in Example 9 was selected that contained a small number (2 to 6) of microparticles. Images were captured and stored as a pixel stack file and analyzed by software installed in the system's personal computer. As described in Example 9, a prescan measurement was taken to record the assay background.

Approximately 5 mL of 1 µM Lac2-F nonspecific target DNA in 0.3 M NaCl, PBS buffer was flowed continuously across the JBP2BC PNA probe-coupled microparticles at a flow rate of about 1 mL/min, and was collected and recycled in a closed loop system for 1 h. The JBP2BC PNA probe-coupled microparticles were then washed with 10 mL of 0.3 M, PBS buffer, and the effluent was discarded. Resonant light scattering measurements were taken after the wash. Approximately 5 mL of 1 µM JBP-F specific target DNA in 0.3 M NaCl, PBS buffer was then added to the flow cell and was flowed continuously across the microparticles for 1 h, followed by a 10 mL wash with 0.3 M NaCl, PBS buffer. Again, a resonant light scattering spectral scan, as described in Example 3, was taken of the JBP2BC PNA probe-coupled microparticles after the wash.

The results are shown in Table 6. A negative shift in the resonant light scattering pattern was observed upon nonspecific binding of the Lac2-F target oligonucleotide to the microparticles. The results also show that a larger negative shift in the resonant light scattering pattern was observed upon binding of the specific JBP-F oligonucleotide DNA target to the JBP2BC PNA probe-coupled microparticles, demonstrating the use of resonant light scattering to detect DNA oligonucleotide binding to PNA oligomer-coupled microparticles. A negative resonance wavelength shift in resonant light scattering spectra was observed when oligonucleotide DNA targets, either as nonspecific or specific analytes, were bound to PNA oligomer-coupled microparticles.

TABLE 6

Resonance Wavelength Shifts in the Resonant Light Scattering Spectra of PNA Probe-Coupled Microparticles upon Binding to Oligonucleotide Targets

| Microparticles | Resonance wavelength shift (nm), step 1-background: 0.3 M NaCl, PBS buffer, pH 7.4 | Resonance wavelength shift (nm), step 2- non-specific analyte target: Lac2-F oligonucleotide non-specifically bound | Resonance wavelength shift (nm), step 3- specific analyte target: JBC-F oligonucleotide specifically bound |
|---|---|---|---|
| JBP2BC PNA probe-coupled microparticles | 0.0 ± 0.003 | −0.0127 ± 0.005 | −0.0222 ± 0.009 |

Example 12

Detection of Hybridization Capture of a PCR Product Target onto PNA Probe-coupled Microparticles Using Resonant Light Scattering The purpose of this Example was to demonstrate the detection of a PCR product analyte using PNA probe-coupled microparticles with resonant light scattering.

A. Microparticle Preparation and Oligonucleotide Probe Coupling:

The JBP2BC PNA probe-coupled microparticles were the same as those used in Example 11.

B. Preparation of PCR Targets:

The nonspecific PCR test target for the JBP2BC PNA probe-coupled microparticles was the same 511 bp amplified Lac2-511 asymmetric PCR product (SEQ ID NO:9) used to test the JBP S2SP3B probe-coupled microparticles in Example 10. The specific test target was the compliment of the 206 bp amplified JB asymmetric PCR product, given as SEQ ID NO:16, amplified as in Example 10 but with the forward primer (P2FWD, SEQ ID NO:10) at 20 pmol and the reverse primer (P33-4, SEQ ID NO:11) at 2 pmol. Five microliters of the product was then reamplified in the presence of 50 pmol of the forward primer and 5 pmol of the reverse primer.

C. Detection of Hybridization Capture of the FMD PCR Product Target DNA onto JBP2BC PNA Probe-coupled Microparticles Using Resonant Light Scattering:

As described in Example 10, a small aliquot, 2 to 3 µL, of the JBP2BC PNA probe-coupled microparticle suspension was placed in an optical cell. A field of view similar to that shown in FIG. 8 and described in Examples 9, 10 and 11 was selected that contained a small number (2 to 6) of microparticles. Resonant light scattering detection was performed as described in Example 10 and spectral measurements were taken after each incubation/wash step. The Lac2-511 PCR fragment and the JB PCR target fragment were used as the control and assay targets, respectively.

The results in Table 7 show that a significant negative shift was observed in the resonant light scattering pattern upon binding of the JB PCR product to the JBP2BC PNA probe-coupled microparticles, demonstrating the use of resonant light scattering to detect specific PCR DNA targets bound to PNA oligomer-coupled microparticles.

TABLE 7

Resonance Wavelength Shifts in the Resonant Light Scattering Spectra of PNA Probe-Coupled Microparticles upon Binding to PCR Produced DNA Analytes

| Microparticles | Resonance wavelength shift (nm), step 1- background: 0.3 M NaCl, PBS buffer, pH 7.4 | Resonance wavelength shift (nm), step 2- nonspecific analyte target: Lac2-511 PCR fragment | Resonance wavelength shift (nm), step 3- specific analyte target: JB PCR fragment |
|---|---|---|---|
| JBP2BC PNA probe-coupled microparticles | 0.0 ± 0.00013 | −0.0029 ± 0.0016 | −0.0158 ± 0.0016 |

Example 13

Detection of Cleavage of DNA Probe Off Microparticles Using Resonant Light Scattering The purpose of this Example was to demonstrate that the negative resonant light scattering spectral shift observed when a DNA target analyte was captured onto a DNA probe-coupled microparticle is due to the binding of the nucleic acid to the DNA-probe. Fluorescent-labeled analytes were used as assay controls to verify specific binding of the analyte to the nucleic acid-coupled microparticles and that the hybridization complex formed was removed when the coupling cross-linker was cleaved.

A. Microparticle Preparation:

The high refractive index glass microparticles were prepared and silanized to produce surface reactive amine groups, as described in Examples 3, 9 and 10. These amine-derivatized glass microparticles were further derivatized with pyridyldithio groups that couple to thiol-modified oligonucleotide probes to form disulfide bonds, as described below. The disulfide bonds are cleavable with DTT, which can be used to remove the oligonucleotide probe or the nucleic acid hybridization complex from the microparticles.

The coupling agent used to modify the microparticles with pyridyldithio groups was sulfosuccinimidyl 6-[3'-(2-pyridyldithio)-propionamido]hexanoate (sulfo-LC-SPDP) (Pierce Biotechnology, Inc, Rockford, Ill.). This coupling agent has a NHS group at one end of the molecule that couples the sulfo-LC-SPDP cross-linker to the amine groups on the surface of the microparticles. An aliquot of 100 µg of amine-derivatized glass microparticles was added to a reaction mixture consisting of 100 mM carbonate/bicarbonate buffer, pH 9.6, 122 mg/mL of sulfo-LC-SPDP, and 25% dimethylformamide (DMF). The mixture was placed into a 1.5 mL round-bottom tube that was rotated at room temperature for 2 h to allow the surface amines to react with the NHS group on sulfo-LC-SPDP. The resulting pyridyldithio-derivatized microparticles were washed at room temperature with 500 µL of PBS, pH 7.4. The buffer and sulfo-LC-SPDP were removed by centrifuging the suspended microparticles using a Microcon®100 microconcentrator in a Sorvall Microspin microcentrifuge at 12,000 rpm and room temperature. The microparticles were washed twice with PBS buffer. The pyridyldithio-derivatized microparticle pellet was transferred to a second 1.5 mL round-bottom tube and stored at 4° C.

B. The Oligonucleotide Probes:

The oligonucleotide probe was JBP S2SP3B, which was described in Example 9 and is given by SEQ ID NO:2. The JBP S2SP3B was coupled to the pyridyldithio-derivatized microparticles as described below. Also coupled to the pyridyldithio-derivatized microparticles was a 3' labeled fluorescein probe (JBP S2SP3F) $C_6$—S—$S(Sp)_2$-TCAAC-CAGATGCAGGAGGACATGTCAACAAAA-CACGGACCCGACTTA A-F 3', given as SEQ ID NO:17. This probe was also modified at the 5' end by a disulfide moiety to react with the pyridyldithio groups on the derivatized microparticles.

To prepare the modified JBP probes, JBP S2SP3F and JBP S2SP3B, for coupling to the pyridyldithio-derivatized microparticles, the disulfide modifier was cleaved on each of the JBP probes in separate reaction mixtures. The reaction mixtures contained 70 nmol of one of the JBP probes in 600 µL of PBS buffer, and 100 mM dithiothreitol (DTT). The thiol-modified oligonucleotides were purified from the C6-thio group and DTT by ethanol precipitation. One hundred microliters of 3 M sodium acetate, pH 5.4, and 1000 µL of 100% ethanol were added to each reaction and the solutions were mixed well. The DNA precipitates were centrifuged into pellets in a Sorvall Microspin microcentrifuge at 12,000 rpm and room temperature. The JBP probe pellets were washed twice with 70% ethanol, and then dissolved in 200 µL of double-distilled water in separate reaction tubes. Both oligonucleotides were coupled to 100 µg of pyridyldithio-derivatized microparticles in 1.5 mL round-bottom tubes by adding 500 µL of PBS, pH 7.4, and rotating at room temperature for 2 h to allow the surface pyridyldithio-groups to react with the thiol-activated JBP probes. Preparations of both types of JBP probe-coupled microparticles were washed at room temperature with 500

µL of PBS. The PBS, DTT, and unreacted JBP probes were removed by centrifuging the suspended microparticles using a Microcon®100 microconcentrator in a Sorvall Microspin microcentrifuge at 12,000 rpm and room temperature. The microparticles were washed twice with PBS. The JBP probe-coupled microparticle pellets were transferred to 1.5 mL micro-tubes, and stored at 4° C.

C. Fluorescence Detection of Hybridization Capture of a JBP Oligonucleotide Target DNA onto the DNA-probe coupled Microparticles:

To demonstrate that the disulfide bonds formed from the cross-linking of the JBP probes to the microparticles using the sulfo-LC-SPDP were cleavable, the disulfide bonds were reduced with DTT. A 50 µL aliquot of the JBP S2SP3F probe-coupled microparticles in PBS buffer pH 7.4 was treated with 50 µL of 0.2 M DTT for 10 min. Then the microparticles were observed under the Zeiss fluorescence microscope, as described in Example 9. The resulting fluorescence micrographs demonstrated that the fluorescent microparticles were no longer fluorescent, indicating that the disulfide bonds produced by the pyridyldithio exchange reaction were cleaved with DTT.

The JBP specific JBC-F (SEQ ID NO:5) target and the nonspecific control Lac2-F (SEQ ID NO:6) were used, as described in Example 9, to test if the JBP probe coupled to the microparticles with the sulfo-LC-SPDP cross-linker, i.e., the JBP S2SP3B probe-coupled micro particles described above, could specifically bind to the JBC-F DNA target.

Micrographs, developed as described in Example 9, showed that the JBC-F DNA targets were captured onto JBP probe-coupled microparticles by forming a fluorescent JBP probe/JBC target hybridization complex. The Lac2-F control targets were not captured. These results indicate that the JBP/disulfide-coupled microparticles are specific for the JBC-F target sequence. The JBP probe/JBC target hybridization complex was then cleaved from the microparticles with 0.2 M DTT as described above. The resulting micrograph showed that the hybridization complex-cleaved microparticles were much less fluorescent, indicating that at least some of the hybridization complexes were cleaved from the JBP-coupled microparticles.

Resonant Light Scattering Detection using JBP Probe-coupled (w/Sulfo-LC-SPDP) Microparticles:

Resonant light scattering was used to detect the binding of JBC-F (SEQ ID NO:5) target DNA to the JBP-coupled microparticles. The procedure was similar to that used in Examples 2, 3, and 9. The JBP-coupled microparticles, prepared as described in Parts A and B above, were dispersed in 0.3 M NaCl, PBS buffer, pH 7.4 and a small aliquot (2–3 µL) of the resulting microparticle suspension was placed in an optical cell, similar to the one described in Example 3 and shown in FIG. 6. A field of view similar to that shown in FIG. 8 was selected that contained a small number (2 to 6) of microparticles. Images were captured and stored as a pixel stack file and analyzed by software installed in the system's personal computer. As in Example 9, a prescan measurement was taken to record the assay background.

Approximately 5 mL of the specific target JBC-F DNA (1 µM in 0.3 M NaCl, PBS, pH 7.4) was flowed continuously across the microparticles at a flow rate of about 1 mL/min and was recycled in a closed loop system for 1 h. The microparticles were then washed with 10 mL of 0.3 M NaCl, PBS, pH 7.4, and the effluent was discarded. Resonant light scattering spectral measurements were taken after the wash. A reducing agent (0.1 M DTT in 0.1 M phosphate buffer pH 8.4) was then added for 30 min, followed by a 10 mL wash with 0.3 M NaCl, PBS, pH 7.4. Again, resonant light scattering spectral measurements were taken after the wash.

The results given in Table 8 show that there was a significant negative shift in the resonant light scattering pattern after the addition of the DNA target and a further negative shift once the probe-target complex was cleaved off the microparticles. The data demonstrates that the shift that appears to be negative is a result of the DNA (nucleic acid) probe coupled to the microparticles through crosslinkers. From the data, it appears that the influence of nucleic acids coupled to microparticles is such that the resonance wavelength shift produced upon binding of the nucleic acid analytes in the resonant light scattering assay is negative.

TABLE 8

Resonance Wavelength Shifts in the Resonant Light Scattering Spectra of Oligonucleotide DNA Probe-Coupled Microparticles Upon Binding to Oligonucleotide Targets

| Microparticles | Resonance wavelength shift (nm), step 1- background: 0.3 M NaCl, PBS buffer, pH 7.4 | Resonance wavelength shift (nm), step 3- specific analyte target: JBC-F oligonucleotide bound | Resonance wavelength shift (nm), step 3- DTT cleavage of probe-target complex from the microparticles |
|---|---|---|---|
| JBP S2SP3B probe-coupled microparticles | 0.0 ± 0.005 | −0.0161 ± 0.004 | −0.0275 ± 0.006 |

Example 14

Predicted Resonant Light Scattering Spectra for Microparticles Having a High Refractive Index Core Plus One Layer, 1 Set of Resonances The purpose of this Example was to use computer simulation to predict the resonant light scattering spectra for microparticles with a homogeneous core of high refractive index plus one other layer. The effect of a 10 nm thick protein layer is also predicted.

The simulations were constructed using computer models of resonant light scattering from multilayer spherical microparticles. The models that were used extend well-known concepts and formulas from literature references, for example Kaiser, T. and Schweiger, G., *Computers in Physics* 7(6), 682–686 (1993). The models allow up to 10 layers to be specified as to diameter (core) or thickness (layers) and refractive index (RI). The following parameters were used in the simulations:

| Medium refractive index (RI) | 1.33 |
| Starting Wavelength | 770 |
| Ending Wavelength | 780 |
| Scattering angle | 180 degrees |
| Detection full acceptance angle | 21.7 degrees |

The diameter and refractive index of the core and the thickness and refractive index of the layer were varied. The binding of a protein layer was modeled by the addition of a uniform 10 nm thick layer of refractive index 1.45 on the outside of the microparticle.

Particle-by-particle Specifications:

The particle number is listed in Table 9 followed by the parameters used in the simulations: Core diameter ($D_{Core}$ in FIG. 18), Core refractive index ($RI_{core}$ in FIG. 18), Layer 1 thickness (T1 in FIG. 18), and Layer 1 refractive index ($RI_{L1}$ in FIG. 18).

TABLE 9

Particle Parameters Used to Calculate the Predicted Spectra of Example 14

| Particle No. | Core diameter (μm) | Core RI | Layer one thickness (μm) | Layer one RI | Protein layer (μm) | Protein layer RI |
|---|---|---|---|---|---|---|
| 1 (Reference particle) | 40 | 1.8 | 0.5 | 1.65 | — | — |
| 2 | 40.8 | 1.8 | 0.5 | 1.65 | — | — |
| 3 | 40 | 1.78 | 0.5 | 1.65 | — | — |
| 4 | 40 | 1.8 | 0.8 | 1.65 | — | — |
| 5 | 40 | 1.8 | 0.5 | 1.62 | — | — |
| 6 | 39.4 | 1.83 | 0.4 | 1.63 | — | — |
| 7 | 40 | 1.8 | 0.5 | 1.9 | — | — |
| 8 | 40 | 1.8 | 0.5 | 1.65 | 0.01 | 1.45 |

The predicted scattering patterns are shown in FIGS. 18–19. Variations in diameter of the core and layer, and in refractive index (RI) of the core and layer, give rise to variations in the scattering pattern suitable for use as identifying markers for the particle (Particles 1–7). These results illustrate the use of a homogeneous core plus one layer as an identifiable microparticle.

Addition of a 10 nm thick protein layer induces a shift in the overall scattering pattern suitable for detecting the binding of a target protein (Particle 8). The effect of the binding can be seen graphically by comparing the scattering plot of the particle containing the protein layer with that of the reference particle, as shown in FIG. 19. For convenience there are two plots shown comparing the bound vs. unbound particles, one with an expanded wavelength scale to more readily show the pattern shifts that occur upon binding. Although the comparison is shown only for binding to the reference particle, the same effect could be shown for any of the other particles in the Example.

Example 15

Predicted Resonant Light Scattering Spectra for Microparticles Having a Low Refractive Index Core Plus 1 Layer, 1 Set of Resonances The purpose of this Example was to use computer simulation to predict the resonant light scattering spectra for microparticles with a homogeneous core of low refractive index plus one other layer of higher refractive index. The effect of a 10 nm thick protein layer is also predicted.

The simulated spectra were calculated as described in Example 5 using the same values given in that Example for the medium RI, the starting and ending wavelengths, the scattering angle, and the detection full acceptance angle. The diameter and refractive index of the core and the thickness and refractive index of the layer were varied. The binding of a protein layer was modeled by the addition of a uniform 10 nm thick layer of refractive index 1.45 on the outside of the microparticle.

Particle-by-particle Specifications:

The particle number is listed in Table 10 followed by the parameters used in the simulation: Core diameter ($D_{Core}$ in FIG. 20), Core refractive index ($RI_{Core}$ in FIG. 20), Layer 1 thickness (T1 in FIG. 20), and Layer 1 refractive index ($RI_{L1}$ in FIG. 20). In this Example, Particle 1 is a homogeneous core only, given for reference. In the remaining particles, the core and layer thicknesses are such that the total particle size is the same as for Particle 1. The addition of protein is done on Particle 2, so for the purposes of illustrating the detection of protein binding, Particle 2 should be used as a reference particle.

TABLE 10

Particle Parameters Used to Calculate the Predicted Spectra of Example 15

| Particle No. | Core diameter (μm) | Core RI | Layer one thickness (μm) | Layer one RI | Protein layer (μm) | Protein layer RI |
|---|---|---|---|---|---|---|
| 1 | 40 | 1.5 | 0 | — | — | — |
| 2 (Reference particle) | 20 | 1.5 | 10 | 1.7 | — | — |
| 3 | 19.1 | 1.5 | 10 | 1.7 | — | — |
| 4 | 20 | 1.6 | 10 | 1.7 | — | — |
| 5 | 20 | 1.5 | 9 | 1.7 | — | — |
| 6 | 20 | 1.5 | 10 | 1.74 | — | — |
| 7 | 20.3 | 1.57 | 8 | 1.67 | — | — |
| 8 | 20 | 1.5 | 10 | 1.7 | 0.01 | 1.45 |

The predicted scattering patterns are shown in FIGS. 20–21. These results illustrate the use of a homogeneous core of low refractive index, plus one layer of higher refractive index, as an identifiable microparticle. Such a microparticle gives rise to one set of scattering resonances that are produced by the high/low refractive index transition between the layer and the medium. Variations in diameter of the core outside the caustic surface (for a definition of the caustic surface, see for example Roll, G. and Schweiger, G., *J. Opt. Soc. Am. A* 17(7), 1301–1311 (2000)), variations in the thickness of the layer, and also in refractive index (RI) the core and layer, give rise to variations in the scattering pattern suitable for use as identifying markers for the particle (Nos. 1–7). Addition of a 10 nm thick protein layer induces a shift in the overall scattering pattern suitable for detecting the binding of a target protein (No. 8), as shown in FIG. 21.

Example 16

Predicted Resonant Light Scattering Spectra for Microparticles Having a High Refractive Index Core Plus 1 Layer 2 Sets of Resonances The purpose of this Example was to use computer simulation to predict the resonant light scattering spectra for microparticles with a homogeneous core of high refractive index plus one other layer of lower refractive index. The effect of a 10 nm thick protein layer is also predicted.

The simulated spectra were calculated as described in Example 5 using the same values given in that Example for the medium RI, the starting and ending wavelengths, the scattering angle, and the detection full acceptance angle. The diameter and refractive index of the core and the thickness and refractive index of the layer were varied. The binding of a protein layer was modeled by the addition of a uniform 10 nm thick layer of refractive index 1.45 on the outside of the microparticle.

Particle-by-particle Specifications:

The particle number is listed in Table 11 followed by the parameters used in the simulations: Core diameter ($D_{Core}$ in FIG. 22), Core refractive index ($RI_{core}$ in FIG. 22), Layer 1 thickness ($T_1$ in FIG. 22), and Layer 1 refractive index ($RI_{L1}$ in FIG. 22). In this Example, Particle 1 is a homogeneous core only, given for reference. In the remaining particles, the core and layer thicknesses are such that the total particle size is the same as for Particle 1. The addition of protein is done on Particle 2, so for the purposes of illustrating the detection of protein binding, Particle 2 should be used as a reference particle.

TABLE 11

Particle Parameters Used to Calculate the Predicted Spectra of Example 16

| Particle No. | Core diameter (µm) | Core RI | Layer one thickness (µm) | Layer one RI | Protein layer (µm) | Protein layer RI |
|---|---|---|---|---|---|---|
| 1 | 40 | 1.65 | — | — | — | — |
| 2 (Reference particle) | 30 | 1.85 | 10 | 1.65 | — | — |
| 3 | 31.1 | 1.85 | 10 | 1.65 | — | — |
| 4 | 30 | 1.87 | 10 | 1.65 | — | — |
| 5 | 30 | 1.85 | 10.9 | 1.65 | — | — |
| 6 | 30 | 1.85 | 10 | 1.67 | — | — |
| 7 | 29.5 | 1.82 | 9.7 | 1.63 | — | — |
| 8 | 30 | 1.85 | 10 | 1.65 | 0.01 | 1.45 |

The predicted scattering patterns are shown in FIGS. 22–23. These results illustrate the use of a homogeneous core of high refractive index, plus one layer of lower refractive index, as an identifiable microparticle. Such a microparticle gives rise to additional scattering resonances compared to the particles of Example 6. These additional resonances are produced by the high/low refractive index transition between the core and the layer because that transition is sufficient to establish a second set of resonances. Variations in diameter of the core and layer, and in refractive index (RI) of the core and the layer, give rise to variations in the scattering pattern suitable for use as identifying markers for the particle (Nos. 1–7). Addition of a 10 nm thick protein layer induces a shift in the overall scattering pattern suitable for detecting the binding of a target protein (No. 8), as shown in FIG. 23.

Example 17

Predicted Resonant Light Scattering Spectra for Microparticles Having a Low Refractive Index Core Plus 2 Layers, 2 Sets of Resonances The purpose of this Example was to use computer simulation to predict the resonant light scattering spectra for particles with a homogeneous core of low refractive index, plus two layers, one having a higher refractive index than the other. The effect of a 10 nm thick protein layer is also predicted.

The simulated spectra were calculated as described in Example 5 using the same values given in that Example for the medium RI, the starting and ending wavelengths, the scattering angle, and the detection full acceptance angle. The binding of a protein layer was modeled by the addition of a uniform 10 nm thick layer of refractive index 1.45 on the outside of the microparticle.

Particle-by-particle Specifications:

The particle number is listed in 12 followed by the parameters used in the simulations: Core diameter ($D_{core}$ in FIG. 24), Core refractive index ($RI_{Core}$ in FIG. 24), Layer 1 and 2 thicknesses ($T_1$ and $T_2$, respectively in FIG. 24), and Layer 1 and Layer 2 refractive indices ($RI_{L1}$ and $RI_{L2}$, respectively, in FIG. 24. In this Example, Particle 1 is a homogeneous core only, given for reference. In the remaining particles, the core and layer thicknesses are such that the total particle size is the same as for Particle 1. The addition of protein is done on Particle 2, so for the purposes of illustrating the detection of protein binding, Particle 2 should be used as a reference particle.

TABLE 12

Particle Parameters Used to Calculate the Predicted Spectra of Example 17

| Particle No. | Core diameter (µm) | Core RI | Layer one thickness (µm) | Layer one RI | Layer two thickness (µm) | Layer two RI | Protein layer (µm) | Protein layer RI |
|---|---|---|---|---|---|---|---|---|
| 1 | 40 | 1.7 | — | — | — | — | — | — |
| 2 (Reference particle) | 20 | 1.7 | 10 | 1.85 | 10 | 1.7 | — | — |
| 3 | 20 | 1.7 | 10 | 1.85 | 10 | 1.7 | 0.01 | 1.45 |

The predicted scattering patterns are shown in FIG. 24. These results illustrate the use of a homogeneous core of low refractive index, plus two layers, one having higher refractive index than the other, as an identifiable microparticle. Such a microparticle gives rise to multiple scattering resonances, produced by the high/low refractive index transition between the second layer and the medium and also by the high/low refractive index transition between the core and the first layer. Variations in diameter of the core and layers, and in refractive index (RI) of the core and layers, give rise to variations in the scattering pattern suitable for use as identifying markers for the particle. In this Example, only a reference particle is shown. Varying the 5 parameters, singly or more than one at a time, produces unique spectra as in the previous Examples. Addition of a 10 nm thick protein layer induces a shift in the overall scattering pattern suitable for detecting the binding of a target protein. For simplicity, only the base cases are shown. Varying the parameters in any combination results in changes in the scattered light pattern, showing the utility for generating a high multiplicity of identifying markers for a population of particles.

Particle-by-particle Specifications:

The particle number is listed in Table 13 followed by the parameters used in the simulations: Core diameter ($D_{InnerCore}$ in FIG. 25), Outer Core diameter ($D_{OuterCore}$ in FIG. 25), and Outer Core refractive index ($RI_{OuterCore}$ in FIG. 25). In this Example, Particle 1 is a homogeneous core only, given for reference. In the remaining particles, the inner and outer core diameters are such that the total particle size is the same as for Particle 1. The addition of protein is done on Particle 11, so for the purposes of illustrating the detection of protein binding, Particle 11 should be used as a reference particle.

TABLE 13

Particle Parameters Used to Calculate the Predicted Spectra of Example 18

| Particle No. | Core diameter (μm) | Core RI | Black core diameter (μm) | Black Core Real RI | Black Core Imag RI | Layer thickness (μm) | Layer RI | Protein layer (μm) | Protein layer RI |
|---|---|---|---|---|---|---|---|---|---|
| 1 | 40 | 1.8 | — | — | — | — | — | — | — |
| 2–6 | — | — | 5 to 25 increasing by 5 | 1.8 | 0.01 | To make 40 μm overall diameter | 1.8 | — | — |
| 7–18 | — | — | 26 to 37 increasing by 1 | 1.8 | 0.01 | To make 40 μm overall diameter | 1.8 | — | — |
| 19 | — | — | 30 | 1.8 | 0.01 | 10 | 1.8 | 0.01 | 1.45 |

Example 18

Predicted Resonant Light Scattering Spectra for Microparticles Having a Core with a Black Center The purpose of this Example was to use computer simulation to predict the resonant light scattering spectra for particles with a two-part core. The inner part is an optically opaque sphere, and the outer part is an optically transparent shell. The effect of a 10 nm thick protein layer is also predicted.

The simulated spectra were calculated as described in Example 5 using the same values given in that Example for the medium RI, the starting and ending wavelengths, the scattering angle, and the detection full acceptance angle. The binding of a protein layer was modeled by the addition of a uniform 10 nm thick layer of refractive index 1.45 on the outside of the microparticle.

The predicted scattering patterns are shown in FIGS. 25–27. In FIG. 26, it is seen that for core diameters less than about 29 μm, no effect is observed from the presence of the absorbing core. These core diameters are smaller than that of the caustic surface. The disappearance of optical resonances is illustrated as the diameter of absorbing core reaches the diameter of the caustic surface. In this Example, the caustic surface is between 31 and 32 μm in diameter. The effect is quite rapid with increasing core diameter. Some resonance structures are still seen in the 31 μm core particle; when the core reaches 32 μm the resonances are substantially destroyed. As the inner absorbing core grows, it eventually comprises most of the particle. Although some values of the absorbing core diameter give rise to slowly varying ripple structure in the resonance patterns, the sharp resonance structures shown in earlier Examples do not return. FIG. 27 shows the detection of protein binding on the outside of a two-layer core, the core comprising an absorbing sphere. In this Example, the core diameter is less than that of the caustic surface and thus does not interfere with the production of resonance features.

The results of this Example show that structures inside of the caustic surface do not interfere with the production of optical resonances. Thus, for example, the core may consist of a highly light-absorbing inner particle such as a magnetic or colored microsphere, providing the diameter of the inner particle is less than the diameter of the caustic surface. When the diameter of the inner absorbing core reaches that of the caustic surface, the production of resonant scattering features is no longer possible, as shown in particles 13 through 18 of this Example. Physically this may be understood by recognizing that the light rays giving rise to the resonant scattering features travel in orbits just inside the outer surface of the particle, trapped by total internal reflection. The caustic surface lies inside the physical outer surface of the particle, and defines the zone in which the rays travel. When the absorbing core is large enough to encroach into this zone, it absorbs the rays, destroying the ability for resonance to occur.

Binding of a protein layer on the surface of the "black-centered" two-layered microparticle is detected as a shift in the scattering pattern for those particles in which the core is sufficiently small to enable the production of resonances.

in the simulations: Core refractive index ($RI_{Core}$ in FIG. 28), and Layer 1, 2, 3, . . . 9 refractive indices ($RI_{L1}$–$RI_{L9}$, respectively, in FIG. 28). In this Example, Particle 1 is a homogeneous core only, given for reference. In the remaining particles, the core and layer thicknesses are such that the total particle size is the same as for Particle 1. The addition of protein is done on Particle 5, so for the purposes of illustrating the detection of protein binding, Particle 5 should be used as a reference particle. Note that for simplicity, not all layers are shown in the drawing. Particle 1, the reference particle for homogeneous structure, has a core diameter of 40 μm and a core RI of 1.8. For particles 2–8, the core diameter is 8 μm and the layer thicknesses are 2 μm, so as to make the total diameter of particles 2–8 to be 40 μm, the same as Particle 1.

TABLE 14

Particle Parameters Used to Calculate the Predicted Spectra of Example 19

| Particle No. | Core RI | Layer 2 RI | Layer 3 RI | Layer 4 RI | Layer 5 RI | Layer 6 RI | Layer 7 RI | Layer 8 RI | Layer 9 RI | Protein layer (μm), RI |
|---|---|---|---|---|---|---|---|---|---|---|
| 2 (linear variation) | 1.7200 | 1.7300 | 1.7400 | 1.7500 | 1.7600 | 1.7700 | 1.7800 | 1.7900 | 1.800 | — |
| 3 (linear) | 1.7500 | 1.7611 | 1.7667 | 1.7722 | 1.7778 | 1.7833 | 1.7889 | 1.7944 | 1.800 | — |
| 4 (non-linear) | 1.7500 | 1.7512 | 1.7526 | 1.7553 | 1.7595 | 1.7656 | 1.77414 | 1.7853 | 1.800 | — |
| 5 (non-linear) | 1.7500 | 1.7505 | 1.7506 | 1.7510 | 1.7522 | 1.7553 | 1.7620 | 1.7752 | 1.800 | — |
| 6 (flat1 - non-linear) | 1.7620 | 1.7620 | 1.7620 | 1.7620 | 1.7620 | 1.7620 | 1.7620 | 1.7752 | 1.800 | — |
| 7 (flat2 - non-linear) | 1.7752 | 1.7752 | 1.7752 | 1.7752 | 1.7752 | 1.7752 | 1.7752 | 1.7752 | 1.800 | — |
| 8 (non-linear) | 1.7500 | 1.7505 | 1.7506 | 1.7510 | 1.7522 | 1.7553 | 1.7620 | 1.7752 | 1.800 | 0.01, 1.4500 |

Example 19

Predicted Resonant Light Scattering Spectra for Microparticles Having a Radially Varying Refractive Index Core The purpose of this Example was to use computer simulation to predict the resonant light scattering spectra for particles having a core in which the refractive index varies as a function of the distance from the center. The effect of a 10 nm thick protein layer is also predicted.

The simulated spectra were calculated as described in Example 5 using the same values given in that Example for the medium RI, the starting and ending wavelengths, the scattering angle, and the detection full acceptance angle. The refractive index variation was modeled as a core plus 9 layers, the refractive index of the layers changing with their radii. Several types of variation of refractive index with radius were used, including linear and non-linear variations. The binding of a protein layer was modeled by the addition of a uniform 10 nm thick layer of refractive index 1.45 on the outside of the microparticle.

Particle-by-particle Specifications:

Except for Particle 1, the reference particle, the particle number is listed in Table 14 followed by the parameters used The predicted scattering patterns are shown in FIGS. 28–29. These results illustrate the use of a core in which the refractive index varies as a function of the distance from the center. The results of this Example demonstrate the potential for constructing a population of identifiable microparticles by manufacturing the particles in such a way as to induce a radially varying refractive index. Natural variations will occur in any production method for such a population of particles, these variations giving rise to uniquely distinguishable particles by means of their optical scattering patterns. Binding of a protein layer on the surface of the radially varying core is detected as a shift in the scattering pattern.

Example 20

Predicted Effects of the Medium Refractive Index on the Resonant Light Scattering Spectra The purpose of this Example was to use computer simulation to predict the effect of a change in refractive index of the medium in which the microparticle is placed on the resonant light scattering spectra. The Example considers a homogeneous sphere with no additional optically active layers. The effect of varying refractive index of the medium is compared with the effect of binding a layer of protein.

The simulated spectra were calculated as described in Example 5 using the same values given in that Example for the starting and ending wavelengths, the scattering angle, and the detection full acceptance angle. The refractive index of the medium was varied. The binding of a protein layer was modeled by the addition of a uniform 10 nm thick layer of refractive index 1.45 on the outside of the microparticle.

Particle-by-particle Specifications:

The particle number is listed in Table 15 followed by the parameters used in the simulations: Core diameter ($D_{Core}$ in FIG. 30), Core refractive index ($RI_{Core}$ in FIG. 307), and Medium refractive index (RI).

TABLE 15

Particle Parameters Used to Calculate the Predicted Spectra of Example 20

| Particle No. | Core diameter (μm) | Core RI | Medium RI | Protein layer (μm) | Protein layer RI |
|---|---|---|---|---|---|
| 1 (Reference particle) | 40 | 1.8 | 1.33 | — | — |
| 2 | 40 | 1.8 | 1.33665 | — | — |
| 3 (core plus protein, initial RI) | 40 | 1.8 | 1.33 | 0.01 | 1.45 |
| 4 (core plus protein, changed RI) | 40 | 1.8 | 1.33665 | 0.01 | 1.45 |

Example 21

Predicted Effects of Signal Amplification Using Refractive Index 2.5 Material

The purpose of this Example was to use computer simulation to predict the effect of using a high refractive index structure (for example $TiO_2$ nanoparticles), attached to the target molecules, for enhancing the wavelength shift upon binding of the target to the surface of the microparticle.

The simulated spectra were calculated as described in Example 5 using the same values given in that Example for the medium RI, the starting and ending wavelengths, the scattering angle, and the detection full acceptance angle. The amplification effect was modeled by adding a thin layer of high refractive index material, the thickness of which corresponds to a given mass of nanoparticles, to the outside of a two-layer microparticle on which a protein layer has been added. In this Example, the amplifying structure was assigned a refractive index of 2.5.

Particle-by-particle Specifications:

The particle number is listed in Table 16 followed by the parameters used in the simulations: Core diameter ($D_{Core}$ in FIG. 32), Core refractive index ($RI_{core}$ in FIG. 32), Layer 1 thickness ($T_1$ in FIG. 32), Layer 1 refractive index ($RI_{L1}$ in FIG. 32), protein layer thickness ($T_2$ in FIG. 32), protein layer refractive index ($RI_{L2}$ in FIG. 32), amplifying layer thickness ($T_3$ in FIG. 32), and amplifying layer refractive index ($RI_{L3}$ in FIG. 32).

TABLE 16

Particle Parameters Used to Calculate the Predicted Spectra of Example 21

| Particle No. | Core diameter (μm) | Core RI | Layer one thickness (μm) | Layer one RI | Protein layer (μm) | Protein layer RI | Amplifying layer thickness (nm) | Amplifying layer RI |
|---|---|---|---|---|---|---|---|---|
| 1 (Reference particle) | 40 | 1.7 | 0.4 | 1.6 | — | — | — | — |
| 2 | 40 | 1.7 | 0.4 | 1.6 | 0.01 | 1.45 | — | — |
| 3–5 | 40 | 1.7 | 0.4 | 1.6 | 0.01 | 1.45 | 2 to 6 nm increasing by 2 | 2.5 |

The predicted scattering patterns are shown in FIGS. 30–31. As shown in FIG. 31 (top and bottom pairs of spectra), there is a change in the relative peak intensities, as well as a systematic shift in wavelength when the medium refractive index is changed. As shown in FIG. 31 (middle pair of spectra), there is only a shift in the spectrum with no change in relative peak intensities when a protein layer is added to the reference particle.

The effects of increasing the amplifying layer thickness are shown in FIGS. 32–33. As more amplifying material is added, the wavelength shift increases relative to that using no amplifying material. These results illustrate the use of a high refractive index structure (for example $TiO_2$ nanoparticles), attached to the target molecules, for enhancing the wavelength shift upon binding of the target to the surface of the microparticle. This is a general concept for on-microparticle amplification of the binding signal. Note that unbound target molecules with the amplifier structure attached will have no interfering effect on the scattering spectrum since only bound target is measured.

Example 22

Predicted Effects of Signal Amplification Using Refractive Index 2.2 Material The purpose of this Example was to use computer simulation to predict the effect of using a high refractive index structure (for example a metal or metal oxide or other composition of nanoparticles), attached to the target molecules, for enhancing the wavelength shift upon binding of the target to the surface of the microparticle.

The simulated spectra were calculated as described in Example 5 using the same values given in that Example for the medium RI, the starting and ending wavelengths, the scattering angle, and the detection full acceptance angle. The amplification effect was modeled by adding a thin layer of high-index material, the thickness of which corresponds to a given mass of nanoparticles, to the outside of a two-layer microparticle on which a protein layer has been added. In this Example, the amplifying structure was assigned a refractive index of 2.2, slightly less than that of Example 12.

Particle-by-particle Specifications:

The particle number is listed in Table 17, followed by the parameters used in the simulations: Core diameter ($D_{Core}$ in FIG. 34), Core refractive index ($RI_{Core}$ in FIG. 34), Layer 1 thickness ($T_1$ in FIG. 34), Layer 1 refractive index ($RI_{L1}$ in FIG. 34), protein layer thickness ($T_2$ in FIG. 34), protein layer refractive index ($RI_{L2}$ in FIG. 34), amplifying layer thickness ($T_3$ in FIG. 34), and amplifying layer refractive index ($RI_{L3}$ in FIG. 34).

The effects of increasing the amplifying layer thickness are shown in FIGS. 34–37. As more amplifying material is added, the wavelength shift increases relative to that using no amplifying material. It is seen that the amplifying effect is slightly lower for the lower refractive index material of Example 13 than for the higher refractive index material of Example 12.

These results illustrate the use of a high refractive index structure (for example a layer of metal, metal oxide or other composition of nanoparticles), attached to the target molecules, for enhancing the wavelength shift upon binding of the target to the surface of the microparticle. This is a general concept for on-microparticle amplification of the binding signal. Note that unbound target molecules with the amplifier structure attached will have no interfering effect on the scattering spectrum since only bound target is measured.

It should be noted that the shapes and intensities of the narrow resonance peaks in a spectrum may be affected by the wavelength step size used in the calculations. In all the preceding computer simulation Examples, i.e., Examples 5–13, 2000 wavelength steps were used. In some cases, reducing the step size could give rise to additional narrow resonances being displayed; however, this would not substantially alter the results illustrated by these Examples. In real measurements, the resolution of the detection equipment will dictate which resonances will be used to identify the particle and measure binding.

TABLE 17

Particle Parameters Used to Calculate the Predicted Spectra of Example 22

| Particle No. | Core diameter (μm) | Core RI | Layer one thickness (μm) | Layer one RI | Protein layer (μm) | Protein layer RI | Amplifying layer thickness (nm) | Amplifying layer RI |
|---|---|---|---|---|---|---|---|---|
| 1 (Reference particle) | 40 | 1.7 | 0.4 | 1.6 | — | — | — | — |
| 2 | 40 | 1.7 | 0.4 | 1.6 | 0.01 | 1.45 | — | — |
| 3–7 | 40 | 1.7 | 0.4 | 1.6 | 0.01 | 1.45 | 2 to 10 nm increasing by 2 | 2.2 |

What is claimed is:

1. A method for the identification of an analyte comprising:
    (a) providing a light scanning source which produces light over an analytical wavelength range;
    (b) providing at least two substantially spherical identifiable particles, wherein each particle has an outer optical region which is substantially transparent to light over said analytical wavelength range;
    (c) applying at least one capture probe to the particles of (b) which binds to the outer optical region of the particle, the at least one capture probe having affinity for at least one analyte;
    (d) scanning each particle of (c) one or more times over a first analytical wavelength range to produce at least one first structural reference resonant light scattering spectrum for each particle of (c), said first structural reference resonant light scattering spectrum uniquely identifying each particle;
    (e) correlating the at least one capture probe with each identified particle of (d);
    (f) contacting each of the particles of (e) with a sample suspected of containing the at least one analyte where, if the analyte is present in said sample, binding occurs between the at least one capture probe and the at least one analyte;
    (g) scanning the particles of (f), one or more times over a second analytical wavelength range to produce at least one second binding structural resonant light scattering spectrum for each particle of (f), wherein;
        1) the at least one first reference and at least one second binding structural resonant light scattering spectra may be the same or different; and
        2) the at least first and second analytical wavelength ranges may be the same or different;
    (h) detecting binding of the at least one analyte to the at least one capture probe by comparing differences between the structural resonant light scattering spectra selected from the group consisting of; any of the at least one first reference structural resonant light scattering spectrum and any of the at least one second binding structural resonant light scattering spectrum; and spectrum, wherein comparing the differences is made relative to each uniquely identified particle
    (i) detecting the presence of one or more bound analytes based on the correlation made in step (e) and the at least one second binding structural resonant light scattering spectrum.

2. A method according to claim 1 wherein the particle is scanned over the analytical wavelength range prior to applying the capture probe to produce sin identifying resonant light scattering signature.

3. A method according to claim 1 wherein the analytical wavelength range spans a range from about 1 to about 20 nanometers, within optical wavelengths ranging from about 275 to about 1900 nanometers.

4. A method according to any of claim 1, wherein the amount of bound analyte is determined by comparing the differences between the resonant light scattering signatures selected from the group consisting of: the first reference light scattering signature and any of the at least one second light scattering signature.

5. A method according to claim 3 wherein the optical wavelengths range from about 600 to about 1650 nanometers.

6. A method according to claim 3 wherein the optical wavelengths range from about 770 to about 780 nanometers.

7. A method according to claim 1 wherein the particle is about 100 micrometers in diameter or less.

8. A method according to claim 1 wherein the particle is about 75 micrometers in diameter or less.

9. A method according to claim 1 wherein the particle is about 50 micrometers in diameter or less.

10. A method according to claim 1 wherein the particle is substantially transparent to light over the analytical wavelength range.

11. A method according to claim 1 wherein the particle comprises:
    a) a substantially spherical core; and
    b) one or more layers overlaying the core;
wherein the one or more layers is substantially transparent to light over the analytical wavelength range.

12. A method according to claim 11 wherein the one or more layers are optically active.

13. A method according to claim 11 wherein the one or more layers are biologically active.

14. A method according to claim 11 wherein the one or more layers are chemically active.

15. A method according to either of claims 13 or 14 wherein the layers have a thickness ranging from about 1 nanometer to about 10 micrometers.

16. A method according to claim 12 wherein the core is light absorbing.

17. A method according to claim 11 wherein the one or more layers has a thickness of about 1 nanometer to about 20 micrometers.

18. A method according to claim 12 wherein the one or more layers have a thickness of about 50 nanometers to about 20 micrometers.

19. A method according to claim 11 wherein the core is comprised of materials selected from the group consisting of: glasses, silica, polystyrene, polyester, polycarbonate, acrylic polymers, polyacrylamide, polyacrylonitrile, polyamide, fluoropolymers, silicone, celluloses, semiconducting materials, optically absorbing materials, metals, magnetic materials, minerals, nanoparticles, colloidal particles, metal oxides, metal sulfides, metal selenides, and composites thereof.

20. A method according to claim 19 wherein the magnetic material is iron oxide.

21. A method according to claim 11 wherein the core is hollow.

22. A method according to claim 11 wherein the layers are comprised of materials independently selected from the group consisting of: glasses, silica, polystyrene, polyester, polycarbonate, acrylic polymers, polyacrylamide, polyacrylonitrile, polyamide, fluoropolymers, silicone, celluloses, polyelectrolytes, minerals, nanoparticles, colloidal particles, metal oxides, metal sulfides, metal selenides, and composites thereof.

23. A method according to claim 1 wherein the particle is comprised of glass having an index of refraction of about 1.45 to about 2.1 over the analytical wavelength range.

24. A method according to claim 1 wherein the at least one capture probe is selected from the group consisting of proteins, nucleic acids, peptide nucleic acids, one member of a binding pair, antibodies, biological cells, microorganisms, cell membrane fragments, cellular organelles, receptors, viruses, viral fragments, bacteriophage, bacteriophage fragments, organic ligands, and organometallic ligands.

25. A method according to claim 24 wherein the at least one analyte is present in a sample comprising sample matrix components.

26. A method according to claim 1 wherein the at least one analyte is selected from the group consisting of proteins, nucleic acids, peptide nucleic acids, biological cells, microorganisms, cell membrane fragments, cellular organelles, antibodies, receptors, viruses, viral fragments, bacteriophage, bacteriophage fragments, and one member of a binding pair.

27. A method according to claim 24 wherein the one member of a binding pair is selected from the binding pair combinations consisting of: antigen/antibody, antigen/antibody fragment, Protein A/antibody, Protein G/antibody, hapten/anti-hapten, biotin/avidin, biotin/streptavidin, folic acid/folate binding protein; hormone/hormone receptor, lectin/carbohydrate, enzyme/enzyme cofactor, enzyme/substrate, enzyme/inhibitor, peptide nucleic acid/complimentary nucleic acid, polynucleotide/polynucleotide binding protein, vitamin B 12/intrinsic factor; complementary nucleic acid segments; pairs comprising sulfhydryl reactive groups, pairs comprising carbodiimide reactive groups, and pairs comprising amine reactive groups.

28. A method according to claim 26 wherein the one member of a binding pair is selected from the binding pair combinations consisting of: antigen/antibody, antigen/antibody fragment, Protein A/antibody, Protein G/antibody, hapten/anti-hapten, biotin/avidin, biotin/streptavidin, folio acid/folate binding protein; hormone/hormone receptor, lectin/carbohydrate, enzyme/enzyme cofactor, enzyme/substrate, enzyme/inhibitor, peptide nucleic acid/complimentary nucleic acid, polynucleotide/polynucleotide binding protein, vitamin B 12/intrinsic factor; complementary nucleic acid segments; pairs comprising sulfhydryl reactive groups, pairs comprising carbodiimide reactive groups, and pairs comprising amine reactive groups.

29. A method according to claim 1 wherein the capture probe is synthesized on the surface of the particle.

30. A method according to claim 1 wherein the capture probe is isolated from natural sources or synthesized separately prior to being attached to the surface of the particle.

31. A method according to claim 25 wherein after applying the capture probe to the particle, the particle is treated to prevent non-specific binding of sample matrix components.

32. A method according to claim 25 wherein the particles are coated with a thin film comprising synthetic polymers, naturally occurring polymers, or self assembled monolayers that consist of a single component or a mixture of components, which is chemically activated to allow attachment of the capture probe while preventing non-specific binding of components of the sample matrix.

33. A method according to of claim 1 wherein the either the first reference or second binding resonant light scattering signature comprises spectral features selected from the group consisting of; peak wavelength positions, peak widths, wavelength intervals among peaks, peak amplitudes, and polarization-dependent properties.

34. A method according to claim 1 wherein the reference and binding resonant light scattering signatures are compared on the basis of spectral features selected form the group consisting of; peak wavelength positions, peak widths, wavelength intervals among peaks, peak amplitudes, and polarization-dependent properties.

35. A method according to claim 1 wherein the particle comprises one of more optically active layers.

36. A method according to claim 1 wherein the particle comprises one of more biologically active layers.

37. A method according to claim 1 wherein the particle comprises one of more chemically active layers.

* * * * *

SEQUENCE LISTING

<160> NUMBER OF SEQ ID NOS: 17

<210> SEQ ID NO 1
<211> LENGTH: 516
<212> TYPE: DNA
<213> ORGANISM: Artificial sequence
<220> FEATURE:
<223> OTHER INFORMATION: Synthetic FMD target

<400> SEQUENCE: 1
gcggccgcgc ccccggccac ttttggccat tcacccgagc gaagctagac acaaacaaaa 60
gattgtggca ccggtgaaac agcttttgag ctttgacctg ctcaagttgg caggggacgt 120
cgagtccaac cctgggcctt tcttcttctc tgacgttagg tcaaattttt ccaagttggt 180
tgaaaccatc aaccagatgc aggaggacat gtcaacaaaa cacggacccg actttaaccg 240
gttggtgtct gcatttgagg aactggccac cggagtgaag gctatcagga ccggtctcga 300
tgaggccaaa ccctggtaca agctcatcaa gctcttgagc cgcctgtcat gtatggccgc 360
tgtagcagca cggtcaaagg acccagtcct tgtggccatc atgctggctg acaccggcct 420
tgagattctg gacagtacct ttgtcgtgaa gaagatctcc gactcgctct ccagtctctt 480
tcacgtaccg gcccccgtct tcagtttcgg gaattc 516

<210> SEQ ID NO 2
<211> LENGTH: 48
<212> TYPE: DNA
<213> ORGANISM: Artificial Sequence
<220> FEATURE:
<223> OTHER INFORMATION: Oligonucleotide probe JBP

<400> SEQUENCE: 2
tcaaccagat gcaggaggac atgtcaacaa aacacggacc cgacttaa 48

<210> SEQ ID NO 3
<211> LENGTH: 48
<212> TYPE: DNA
<213> ORGANISM: Artificial Sequence
<220> FEATURE:
<223> OTHER INFORMATION: Modified oligonucleotide probe JBP S2SP3B
<220> FEATURE:
<221> NAME/KEY: modified_base
<222> LOCATION: (1)..(1)
<223> OTHER INFORMATION: C6-S-S(Sp)2, where C6-S-S is
1-O-dimethoxytritylhexyl-disulfide,
1-[(2-cyanoethyl)-N,N-diisopropyl)]-phosphoramidite and Sp is the
spacer 18-O-dimethoxytritylhexaethyleneglycol,
1-[(2-cyanoethyl)-(N,N-diisopropyl)]-phosphoramidite
<220> FEATURE:
<221> NAME/KEY: modified_base
<222> LOCATION: (48)..(48)
<223> OTHER INFORMATION: Biotinylated

<400> SEQUENCE: 3
tcaaccagat gcaggaggac atgtcaacaa aacacggacc cgacttaa 48

<210> SEQ ID NO 4
<211> LENGTH: 48
<212> TYPE: DNA
<213> ORGANISM: Artificial Sequence
<220> FEATURE:
<223> OTHER INFORMATION: Oligonucleotide probe N-JBC
<220> FEATURE:
<221> NAME/KEY: modified_base
<222> LOCATION: (1)..(1)
<223> OTHER INFORMATION: amine group

```
<220> FEATURE:
<221> NAME/KEY: modified_base
<222> LOCATION: (48)..(48)
<223> OTHER INFORMATION: biotinylated

<400> SEQUENCE: 4
ttaagtcggg tccgtgtttt gttgacatgt cctcctgcat ctggttga                    48

<210> SEQ ID NO 5
<211> LENGTH: 48
<212> TYPE: DNA
<213> ORGANISM: Artificial Sequence
<220> FEATURE:
<223> OTHER INFORMATION: Fluorescein-labeled oligonucleotide target
      JBC-F
<220> FEATURE:
<221> NAME/KEY: modified_base
<222> LOCATION: (48)..(48)
<223> OTHER INFORMATION: Fluorescein labeled

<400> SEQUENCE: 5
ttaagtcggg tccgtgtttt gttgacatgt cctcctgcat ctggttga                    48

<210> SEQ ID NO 6
<211> LENGTH: 49
<212> TYPE: DNA
<213> ORGANISM: Artificial Sequence
<220> FEATURE:
<223> OTHER INFORMATION: Fluorescein-labeled oligonucleotide target
      control Lac2-F
<220> FEATURE:
<221> NAME/KEY: modified_base
<222> LOCATION: (49)..(49)
<223> OTHER INFORMATION: Fluorescein labeled

<400> SEQUENCE: 6
tgaatttgat tgcgagtgag atatttatgc cagccagcca gacgcagac                   49

<210> SEQ ID NO 7
<211> LENGTH: 48
<212> TYPE: DNA
<213> ORGANISM: Artificial Sequence
<220> FEATURE:
<223> OTHER INFORMATION: Fluorescein-labeled oligonucleotide target
      JBP-F
<220> FEATURE:
<221> NAME/KEY: modified_base
<222> LOCATION: (48)..(48)
<223> OTHER INFORMATION: Fluorescein labeled

<400> SEQUENCE: 7
tcaaccagat gcaggaggac atgtcaacaa aacacggacc cgacttaa                    48

<210> SEQ ID NO 8
<211> LENGTH: 206
<212> TYPE: DNA
<213> ORGANISM: Artificial Sequence
<220> FEATURE:
<223> OTHER INFORMATION: FMD PCR fragment JB

<400> SEQUENCE: 8
gagtccaacc ctgggcccctt cttcttctct gacgttaggt caaattttc caagttggtt      60 gaaaccatca accagatgca ggaggacatg tcaacaaaac acggaccga ctttaaccgg      120 ttggtgtctg catttgagga actggccacc ggagtgaagg ctatcaggac cggtctcgat    180
gaggccaaac cctggtacaa gctcat                                          206
```

<210> SEQ ID NO 9
<211> LENGTH: 511
<212> TYPE: DNA
<213> ORGANISM: Artificial Sequence
<220> FEATURE:
<223> OTHER INFORMATION: Lac2-511 PCR nonspecific target fragment

<400> SEQUENCE: 9

| | | | | | |
|---|---|---|---|---|---|
| atactgcaga | acgcgtcagt | gggctgatca | ttaactatcc | gctggatgac | caggatgcca | 60 |
| ttgctgtgga | agctgcctgc | actaatgttc | cggcgttatt | tcttgatgtc | tctgaccaga | 120 |
| cacccatcaa | cagtattatt | ttctcccatg | aagacggtac | gcgactgggc | gtggagcatc | 180 |
| tggtcgcatt | gggtcaccag | caaatcgcgc | tgttagcggg | cccattaagt | tctgtctcgg | 240 |
| cgcgtctgcg | tctggctggc | tggcataaat | atctcactcg | caatcaaatt | cagccgatag | 300 |
| cggaacggga | aggcgactgg | agtgccatgt | ccggttttca | acaaaccatg | caaatgctga | 360 |
| atgagggcat | cgttcccact | gcgatgctgg | ttgccaacga | tcagatggcg | ctgggcgcaa | 420 |
| tgcgcgccat | taccgagtcc | gggctgcgcg | ttggtgcgga | tatctcggta | gtgggatacg | 480 |
| acgataccga | agacagctca | tggaattctg | t | | | 511 |

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
gagtccaacc ctgggccctt cttcttc                                              27

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
atgagcttgt accagggttt ggc                                                  23

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
atactgcaga acgcgtcagt gggctgatca                                           30

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
acagaattcc atgagctgtc ttcggtatcg tcgta                                     35

<210> SEQ ID NO 14
<211> LENGTH: 16
<212> TYPE: DNA

```
<213> ORGANISM: Artificial Sequence
<220> FEATURE:
<223> OTHER INFORMATION: Peptide nucleic acid probe JBP2C
<220> FEATURE:
<221> NAME/KEY: misc_feature
<222> LOCATION: (1)..(16)
<223> OTHER INFORMATION: Nucleotide bases are joined by peptide bonds
      instead of phosphodiester bonds

<400> SEQUENCE: 14
tccgtgtttt gttgac                                                      16

<210> SEQ ID NO 15
<211> LENGTH: 16
<212> TYPE: DNA
<213> ORGANISM: Artificial Sequence
<220> FEATURE:
<223> OTHER INFORMATION: Modified Peptide Nucleic Acid Probe JBP2BC
<220> FEATURE:
<221> NAME/KEY: modified_base
<222> LOCATION: (1)..(1)
<223> OTHER INFORMATION: Biotinylated
<220> FEATURE:
<221> NAME/KEY: misc_feature
<222> LOCATION: (1)..(16)
<223> OTHER INFORMATION: Nucleotide bases are joined by peptide bonds
      instead of phosphodiester bonds
<220> FEATURE:
<221> NAME/KEY: modified_base
<222> LOCATION: (16)..(16)
<223> OTHER INFORMATION: Cysteine residue

<400> SEQUENCE: 15
tccgtgtttt gttgac                                                      16

<210> SEQ ID NO 16
<211> LENGTH: 206
<212> TYPE: DNA
<213> ORGANISM: Artificial Sequence
<220> FEATURE:
<223> OTHER INFORMATION: Compliment of PCR product JB

<400> SEQUENCE: 16
atgagcttgt accagggttt ggcctcatcg agaccggtcc tgatagcctt cactccggtg      60
gccagttcct caaatgcaga caccaaccgg ttaaagtcgg gtccgtgttt tgttgacatg     120
tcctcctgca tctggttgat ggtttcaacc aacttggaaa aatttgacct aacgtcagag     180
aagaagaagg gcccagggtt ggactc                                          206

<210> SEQ ID NO 17
<211> LENGTH: 48
<212> TYPE: DNA
<213> ORGANISM: Artificial Sequence
<220> FEATURE:
<223> OTHER INFORMATION: Modified fluorescein-labeled oligonucleotide
      probe JBP S2SP3F
<220> FEATURE:
<221> NAME/KEY: modified_base
<222> LOCATION: (1)..(1)
<223> OTHER INFORMATION: C6-S-S-(Sp)2, where C6-S-S is
      1-O-dimethoxytritylhexyl-disulfide,
      1-[(2-cyanoethyl)-(N,N-diisopropyl)]-phosphoramidite, and Sp is
      the spacer 18-O-dimethoxytritylhexaethyleneglycol,
      1-[(2-cyanoethyl)-(N,N-diisopropyl)]-phosphoramidite
```

```
-continued

<220> FEATURE:
<221> NAME/KEY: modified_base
<222> LOCATION: (48)..(48)
<223> OTHER INFORMATION: Fluorescein labeled

<400> SEQUENCE: 17
tcaaccagat gcaggaggac atgtcaacaa aacacggacc cgacttaa                    48
```